(12) United States Patent
Draghia-Akli et al.

(10) Patent No.: US 9,452,285 B2
(45) Date of Patent: Sep. 27, 2016

(54) ELECTROPORATION DEVICES AND METHODS OF USING SAME FOR ELECTROPORATION OF CELLS IN MAMMALS

(75) Inventors: Ruxandra Draghia-Akli, Houston, TX (US); Amir S. Khan, The Woodlands, TX (US)

(73) Assignee: VGX Pharmaceuticals, Inc., Plymouth Meeting, PA (US)

(*) Notice: Subject to any disclaimer, the term of this patent is extended or adjusted under 35 U.S.C. 154(b) by 2142 days.

(21) Appl. No.: 11/874,072

(22) Filed: Oct. 17, 2007

(65) Prior Publication Data

US 2008/0091135 A1 Apr. 17, 2008

Related U.S. Application Data

(60) Provisional application No. 60/852,149, filed on Oct. 17, 2006, provisional application No. 60/978,982, filed on Oct. 10, 2007.

(51) Int. Cl.
*A61N 1/30* (2006.01)
*A61N 1/32* (2006.01)
*A61N 1/04* (2006.01)

(52) U.S. Cl.
CPC .............. *A61N 1/327* (2013.01); *A61N 1/0412* (2013.01); *A61N 1/0476* (2013.01)

(58) Field of Classification Search
CPC ........................................................ A61N 1/30
USPC ........................................................ 435/440
See application file for complete search history.

(56) References Cited

U.S. PATENT DOCUMENTS

| | | |
|---|---|---|
| 5,019,034 A | 5/1991 | Weaver et al. |
| 5,676,646 A | 10/1997 | Hofmann et al. ........... 604/6.11 |
| 5,702,359 A | 12/1997 | Hofmann et al. ............. 604/20 |
| 6,068,650 A | 5/2000 | Hofmann et al. ................ 607/2 |
| 6,096,020 A | 8/2000 | Hofmann ....................... 604/501 |
| 6,120,493 A | 9/2000 | Hofmann ...................... 604/506 |
| 6,150,148 A | 11/2000 | Nanda et al. .............. 435/173.6 |
| 6,181,964 B1 | 1/2001 | Hofmann et al. ............... 604/21 |
| 6,192,270 B1 | 2/2001 | Hofmann et al. .............. 604/20 |
| 6,208,893 B1 | 3/2001 | Hofmann ....................... 604/21 |
| 6,216,034 B1 | 4/2001 | Hofmann et al. .............. 604/21 |
| 6,233,482 B1 | 5/2001 | Hofmann et al. .............. 604/21 |
| 6,241,701 B1 | 6/2001 | Hofmann ....................... 604/21 |
| 6,256,533 B1* | 7/2001 | Yuzhakov et al. .............. 604/21 |

(Continued)

OTHER PUBLICATIONS

Ivorra and Rubinsky, ("In vivo electrical impedance measurements during and after electroporation of rat liver", Bioelectrochemistry, 2007, vol. 70, pp. 287-295).*

(Continued)

*Primary Examiner* — Samuel Woolwine
*Assistant Examiner* — Kaijiang Zhang
(74) *Attorney, Agent, or Firm* — Thomas Kim

(57) ABSTRACT

Aspects of the present invention relate to electroporation devices and methods of using same to effectively facilitate the introduction of a biomolecule into cells of a selected tissue in a body, in particular skin such as intradermic or subcutaneous tissue. In some aspects, the present invention is a skin EP device, which produces a pulse of energy and delivers same to the skin tissue using a skin electrode array and maintains a constant current in the same skin tissue based on user input, including a preset current, and allows the storage and acquisition of current waveform data.

44 Claims, 36 Drawing Sheets

(56) References Cited

U.S. PATENT DOCUMENTS

| | | | |
|---|---|---|---|
| 6,302,874 | B1 | 10/2001 | Zhang et al. .................. 604/522 |
| 6,697,669 | B2 | 2/2004 | Dev et al. |
| 6,972,013 | B1 * | 12/2005 | Zhang et al. .................. 604/501 |
| 7,171,264 | B1 * | 1/2007 | Hofmann et al. .............. 604/20 |
| 7,245,963 | B2 * | 7/2007 | Draghia-Akli et al. ......... 604/20 |
| 8,209,006 | B2 * | 6/2012 | Smith et al. .................... 604/21 |
| 2004/0167458 | A1 | 8/2004 | Draghia-Akli et al. ......... 604/20 |
| 2005/0052630 | A1 | 3/2005 | Smith et al. .................... 355/53 |
| 2005/0070841 | A1 | 3/2005 | Mathiesen et al. ............. 604/20 |
| 2008/0269153 | A1 * | 10/2008 | Draghia-Akli et al. ......... 514/44 |

OTHER PUBLICATIONS

Babiuk, L. A. et al. 2003. Induction of immune responses by DNA vaccines in large animals. Vaccine 21:649-658.

Brown, P. A. et al. 2004. Immune enhancing effects of growth hormone releasing hormone delivered by plasmid injection and electroporation. Molecular Therapy 10:644-651.

Canatella, P. J. et al. 2001. Prediction and optimization of gene transfection and drug delivery by electroporation. Gene Ther. 8:1464-1469.

Chen, J. F. et al. 2005. Protection against influenza virus infection in BALB/c mice immunized with a single dose of neuraminidase-expressing DNAs by electroporation. Vaccine 23:4322-4328.

Cui, Z. L. et al. 2003. Intradermal immunization with novel plasmid DNA-coated nanoparticles via a needle-free injection device. J. Biotechnol. 102:105-115.

Cui, Z. et al. 2006. Non-invasive immunization on the skin using DNA vaccine. Curr. Drug Deliv. 3:29-35.

Davalos, R. V. et al. 2002. A feasibility study for electrical impedance tomography as a means to monitor tissue electroporation for molecular medicine. IEEE Trans. Biomed. Eng 49:400-403.

Dean, D. A. et al. 2003. Electroporation as a method for high-level nonviral gene transfer to the lung. Gene Ther. 10:1608-1615.

Drabick, J. J. et al. 2001. Cutaneous transfection and immune responses to intradermal nucleic acid vaccination are significantly enhanced by in vivo electropermeabilization. Mol. Ther. 3:249-255.

Draghia-Akli, R. et al. 2003. Effects of plasmid-mediated growth hormone releasing hormone supplementation in young healthy Beagle dogs. Journal of Animal Science 81:2301-2310.

Draghia-Akli, R. et al. 2003. High-efficiency growth hormone releasing hormone plasmid vector administration into skeletal muscle mediated by electroporation in pigs. FASEB J 17:526-528.

Draghia-Akli, R. et al. 2004. A new plasmid-mediated approach to supplement somatotropin production in pigs. Journal of Animal Science 82:E264-E269.

Draghia-Akli, R. et al. 1999. Myogenic expression of an injectable protease-resistant growth hormone-releasing hormone augments long-term growth in pigs. Nat. Biotechnol. 17:1179-1183.

Draghia-Akli, R. et al. 2002. Electrical Enhancement of Formulated Plasmid Delivery in Animals. Technology in Cancer Research & Treatment 1:365-371.

Draghia-Akli, R. et al. 2002. Enhanced animal growth via ligand-regulated GHRH myogenic-injectable vectors. FASEB J. 16:426-428.

Draghia-Akli, R. et al. 2003. Electrokinetic Enhancement of Plasmid Delivery In Vivo. p. 245 in Gene Therapy—Therapeutic Mechanisms and Strategies. N. S. Templeton and D. D. Lasic, eds. Marcel Dekker, Inc., New York.

Dujardin, N. et al. 2002. In vivo assessment of skin electroporation using square wave pulses. J. Control Release 79:219-227.

Dujardin, N. et al. 2001. Topical gene transfer into rat skin using electroporation. Pharm. Res. 18:61-66.

Fattori, E. et al. 2002. Electro-gene-transfer: a new approach for muscle gene delivery. Somat. Cell Mol. Genet. 27:75-83.

Fewell, J. G. et al. 2001. Gene therapy for the treatment of hemophilia B using PINC-formulated plasmid delivered to muscle with electroporation. Mol. Ther. 3:574-583.

Frederickson, R. M. et al. 2003. Nonclinical Toxicology in Support of Licensure of Gene Therapies. Mol. Ther. 8:8-10.

Fredriksen, A. B. et al. 2006. DNA vaccines increase immunogenicity of idiotypic tumor antigen by targeting novel fusion proteins to antigen-presenting cells. Mol. Ther. 13:776-785.

Gehl, J. 2003. Electroporation: theory and methods, perspectives for drug delivery, gene therapy and research. Acta Physiol Scand. 177:437-447.

Gehl, J. et al. 1999. In vivo electroporation of skeletal muscle: threshold, efficacy and relation to electric field distribution. Biochim. Biophys. Acta 1428:233-240.

Glasspool-Malone, J. et al. 2000. Efficient nonviral cutaneous transfection. Mol. Ther. 2:140-146.

Golzio, M. et al. 2005. Inhibition of gene expression in mice muscle by in vivo electrically mediated siRNA delivery. Gene Ther. 12:246-251.

Hooper, J. W. et al. 2004. Smallpox DNA vaccine protects nonhuman primates against lethal monkeypox. J. Virol. 78:4433-4443.

Lee, R. C. et al. 2000. Biophysical injury mechanisms in electrical shock trauma. Annu. Rev. Biomed. Eng 2:477-509.:477-509.

Lesbordes, J. C. et al. 2002. In vivo electrotransfer of the cardiotrophin-1 gene into skeletal muscle slows down progression of motor neuron degeneration in pmn mice. Hum. Mol. Genet. 11:1615-1625.

Lucas, M. L. et al. 2001. In vivo electroporation using an exponentially enhanced pulse: a new waveform. DNA Cell Biol. 20:183-188.

Marti, G. et al.2004. Electroporative transfection with KGF-1 DNA improves wound healing in a diabetic mouse model. Gene Ther. 11:1780-1785.

Martin, G. T. et al. 2002. Theoretical analysis of localized heating in human skin subjected to high voltage pulses. Bioelectrochemistry. 57:55-64.

McMahon, J. M. et al. 2001. Optimisation of electrotransfer of plasmid into skeletal muscle by pretreatment with hyaluronidase—increased expression with reduced muscle damage. Gene Ther. 8:1264-1270.

Medi, B. M. et al. 2005 Skin targeted DNA vaccine delivery using electroporation in rabbits. I: efficacy. Int. J Pharm. 294:53-63.

Pilaro, A. M. et al. 1999. Preclinical development strategies for novel gene therapeutic products. Toxicol. Pathol. 27:4-7.

Pliquett, U. F. et al. 2002. Kinetics of the temperature rise within human stratum corneum during electroporation and pulsed high-voltage iontophoresis. Bioelectrochemistry. 57:65-72.

Prud'homme, G. J. et al. 2006. Electroporation-enhanced nonviral gene transfer for the prevention or treatment of immunological, endocrine and neoplastic diseases. Curr. Gene Ther. 6:243-273.

Roth, A. et al. 2005. Vaccination technique, PPD reaction and BCG scarring in a cohort of children born in Guinea-Bissau 2000-2002. Vaccine 23:3991-3998.

Smith, L. C. et al. 2000. Advances in plasmid gene delivery and expression in skeletal muscle. Curr. Opin. Mol. Ther. 2:150-154.

Terada, Y. et al. 2001. Efficient and ligand-dependent regulated erythropoietin production by naked dna injection and in vivo electroporation. Am. J Kidney Dis. 38:S50-S53.

Tjelle, T. E. et al. 2005. A novel electroporation device for gene delivery in large animals and humans. Vaccine.

Tollefsen, S. et al. 2003. DNA injection in combination with electroporation: a novel method for vaccination of farmed ruminants. Scand. J Immunol. 57:229-238.

Tone, C. M. et al. 2004. Long-term effects of plasmid-mediated growth hormone releasing hormone in dogs. Cancer Gene Ther. 11:389-396.

Vilquin, J. T. et al. 2001. Electrotransfer of naked DNA in the skeletal muscles of animal models of muscular dystrophies. Gene Ther. 8:1097-1107.

Watkins, C. et al. 1999. Analysis of reporter gene expression in ovine dermis and afferent lymph dendritic cells in vitro and in vivo. Vet. Immunol. Immunopathol. 72:125-133.

Wells, D. J. 2004. Gene therapy progress and prospects: electroporation and other physical methods. Gene Ther. 11:1363-1369.

Wong, T. W. et al. 2005. Pilot study of topical delivery of methotrexate by electroporation. Br. J Dermatol. 152:524-530.

Yasui, A. et al. 2001. Elevated gastrin secretion by in vivo gene electroporation in skeletal muscle. Int. J Mol. Med. 8:489-494.

Zhang, L. et al. 2002. Enhanced delivery of naked DNA to the skin by non-invasive in vivo electroporation. Biochim. Biophys. Acta 1572:1-9.

* cited by examiner 2.1 Filename: 0032210_06_06_28_15_26_43.csv 2.2 Animal Number: 32210

2.3 
- Pulse In Sequence: 1, 2
- Prewait (s): 4, 1
- Pluse Width (ms): 52, 52
- Pulse Current (A): 0.1, 0.1

2.4 
- Electrode 1: POS, OFF
- Electrode 2: NEG, POS
- Electrode 3: NEG, NEG 2.5

| Voltage (V) | Current (A) | Voltage (V) | Current (A) | Z1 (Ohms) | Z2 (Ohms) |
|---|---|---|---|---|---|
| 4.54 | 0 | 3.37 | 0 | | |
| 4.49 | 0 | 3.42 | 0 | | |
| 4.59 | 0 | 3.42 | 0 | | |
| 154.08 | 0.1 | 143.53 | 0.1 | 1540.6459 | 1435.1565 |
| 157.6 | 0.1 | 172.35 | 0.1 | 1575.8424 | 1723.3277 |
| 159.84 | 0.1 | 192.23 | 0.09 | 1598.2402 | 2135.6516 |
| 161.06 | 0.1 | 197.36 | 0.1 | 1610.439 | 1973.4027 |
| 161.65 | 0.09 | 197.7 | 0.1 | 1795.9116 | 1976.8023 |
| 160.82 | 0.1 | 197.51 | 0.09 | 1608.0392 | 2194.3117 |
| 159.99 | 0.09 | 197.61 | 0.09 | 1777.4692 | 2195.4227 |
| 159.01 | 0.1 | 197.36 | 0.1 | 1589.941 | 1973.4027 |
| 157.69 | 0.1 | 197.61 | 0.09 | 1576.7423 | 2195.4227 |
| 156.86 | 0.1 | 196.09 | 0.1 | 1568.4432 | 1960.7039 |
| 156.23 | 0.1 | 194.43 | 0.1 | 1562.1438 | 1944.1056 |
| 155.01 | 0.09 | 191.45 | 0.1 | 1722.142 | 1914.3086 |
| 154.57 | 0.1 | 187.35 | 0.1 | 1545.5454 | 1873.3127 |

FIG. 2C

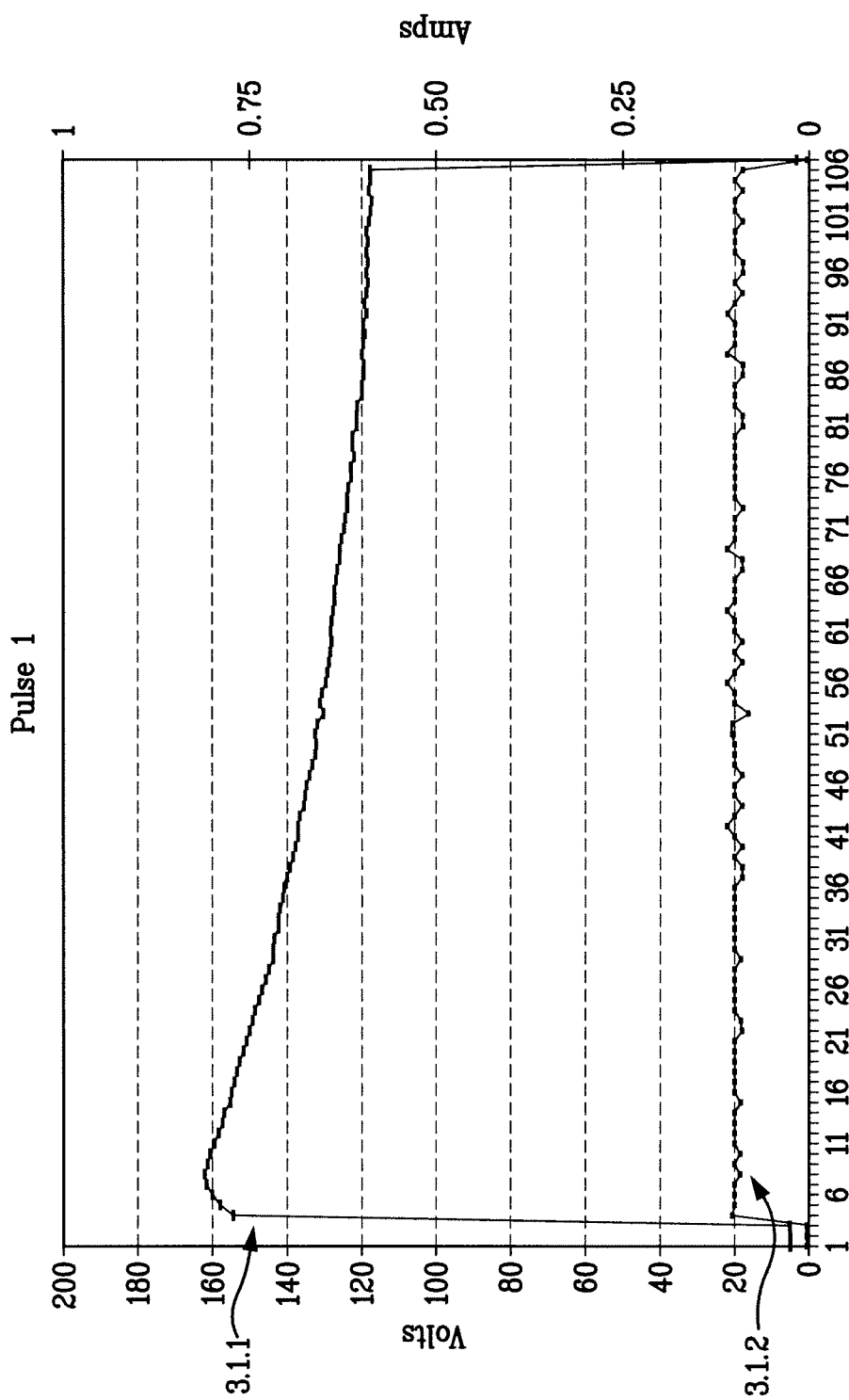
FIG. 3.1

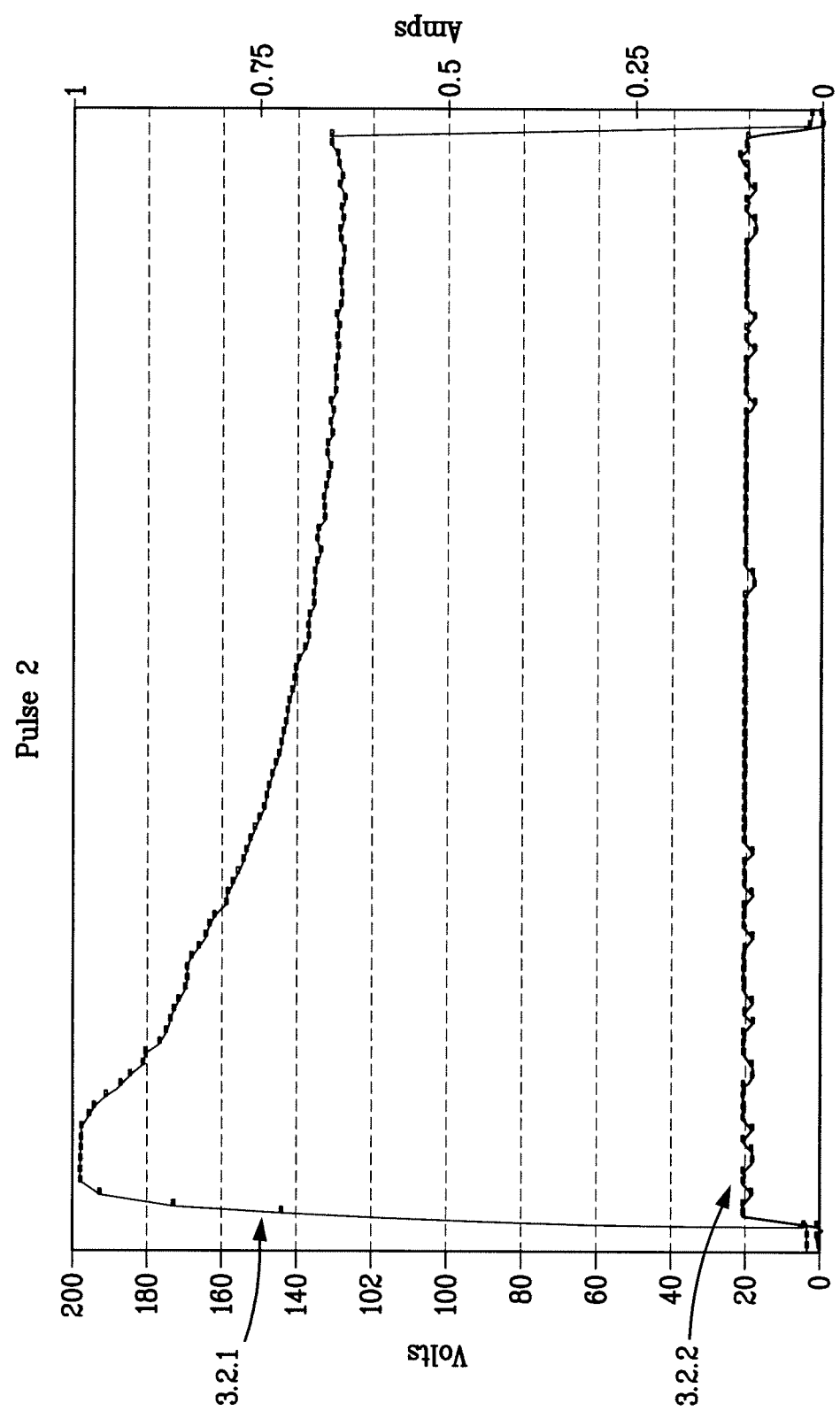
FIG. 3.2

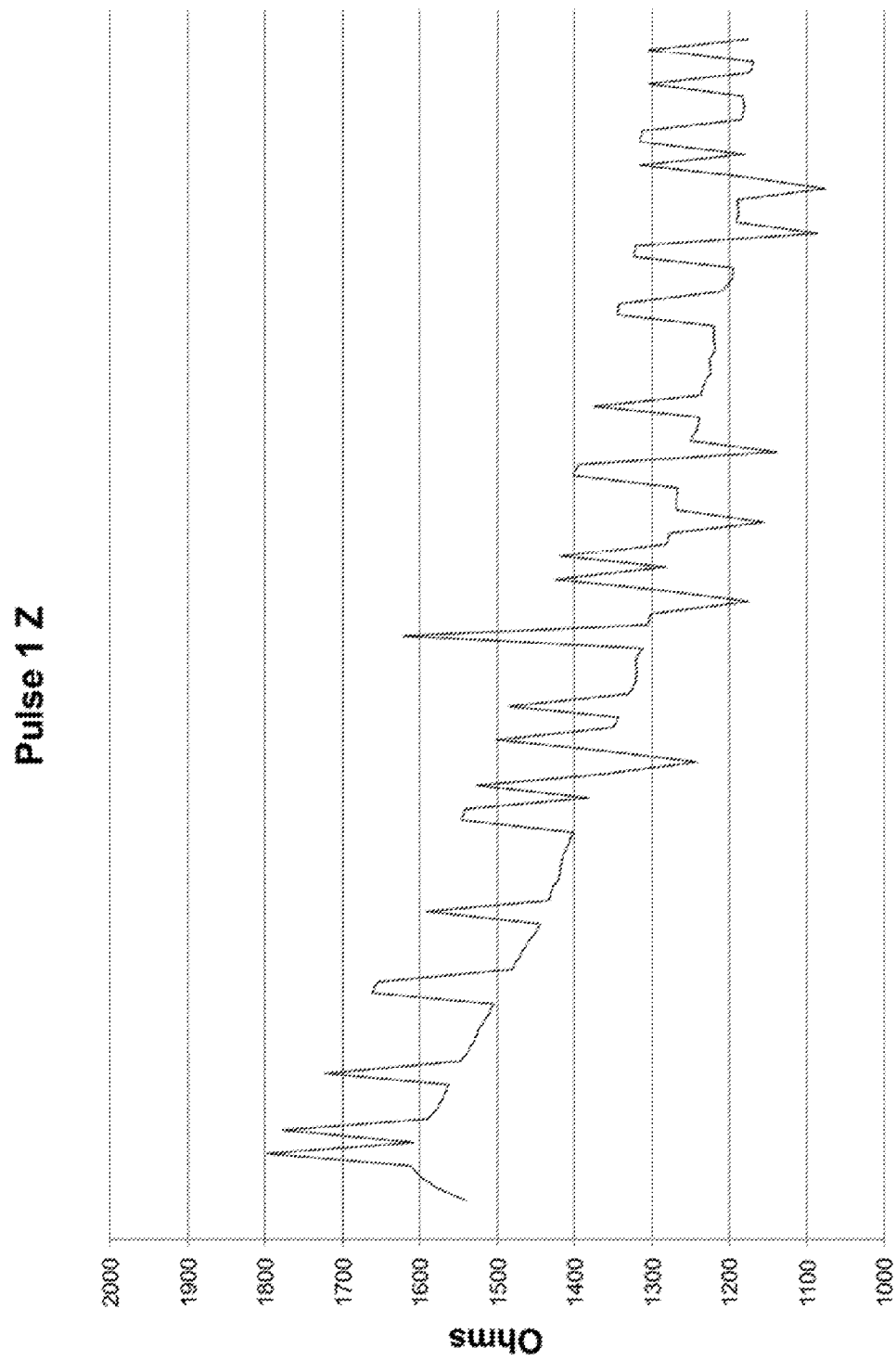
FIG 3.3

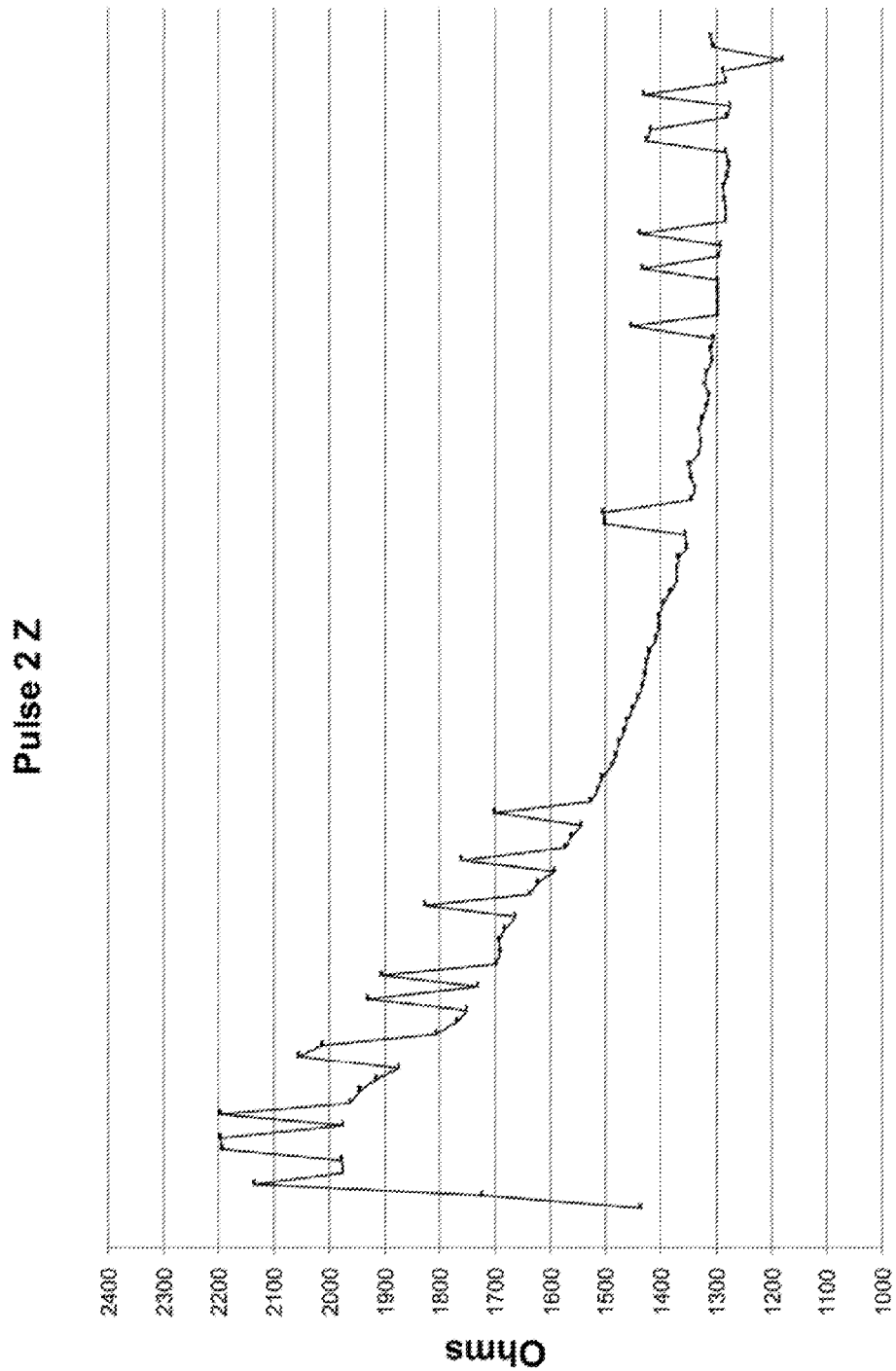
FIG. 3.4

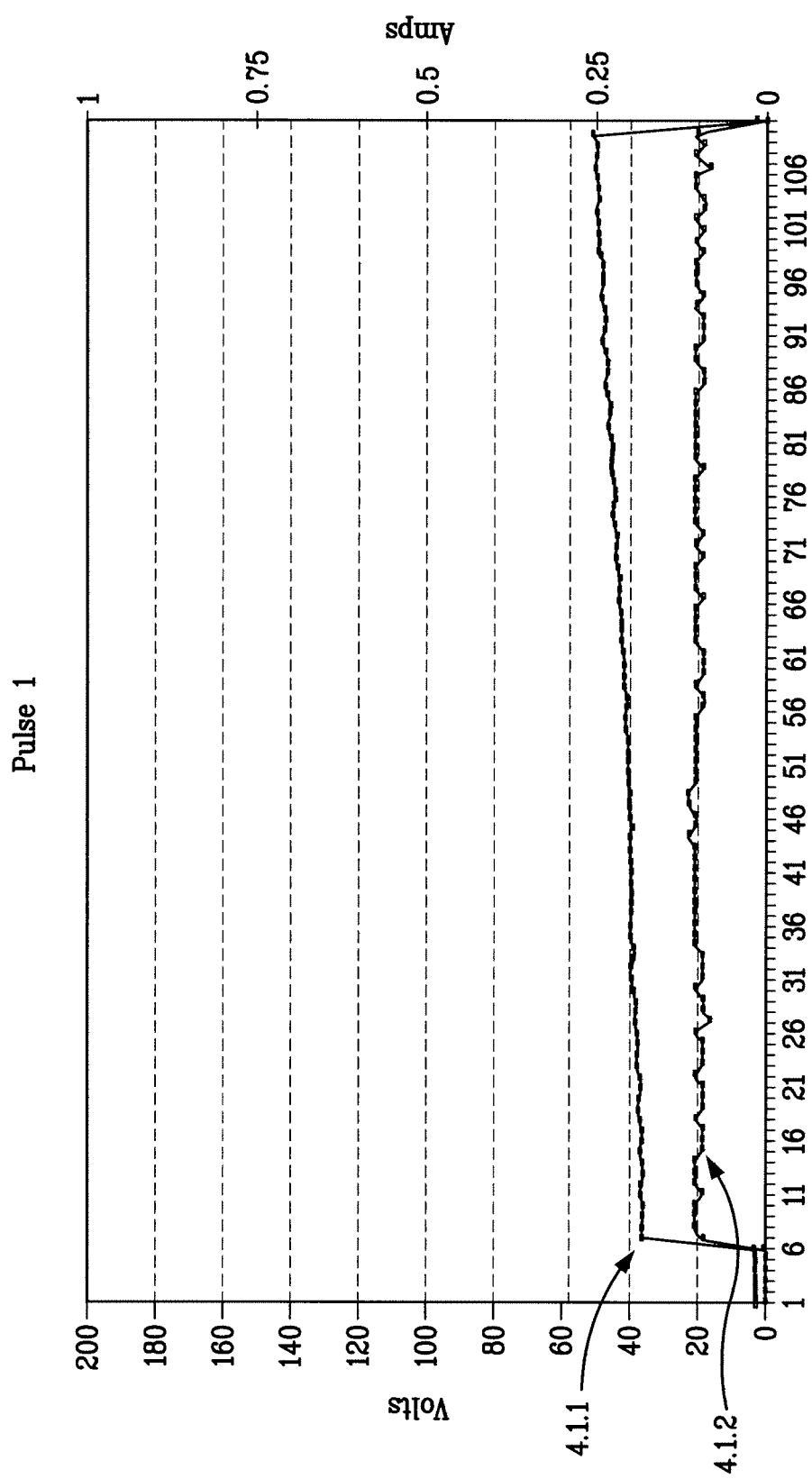
FIG. 4.1

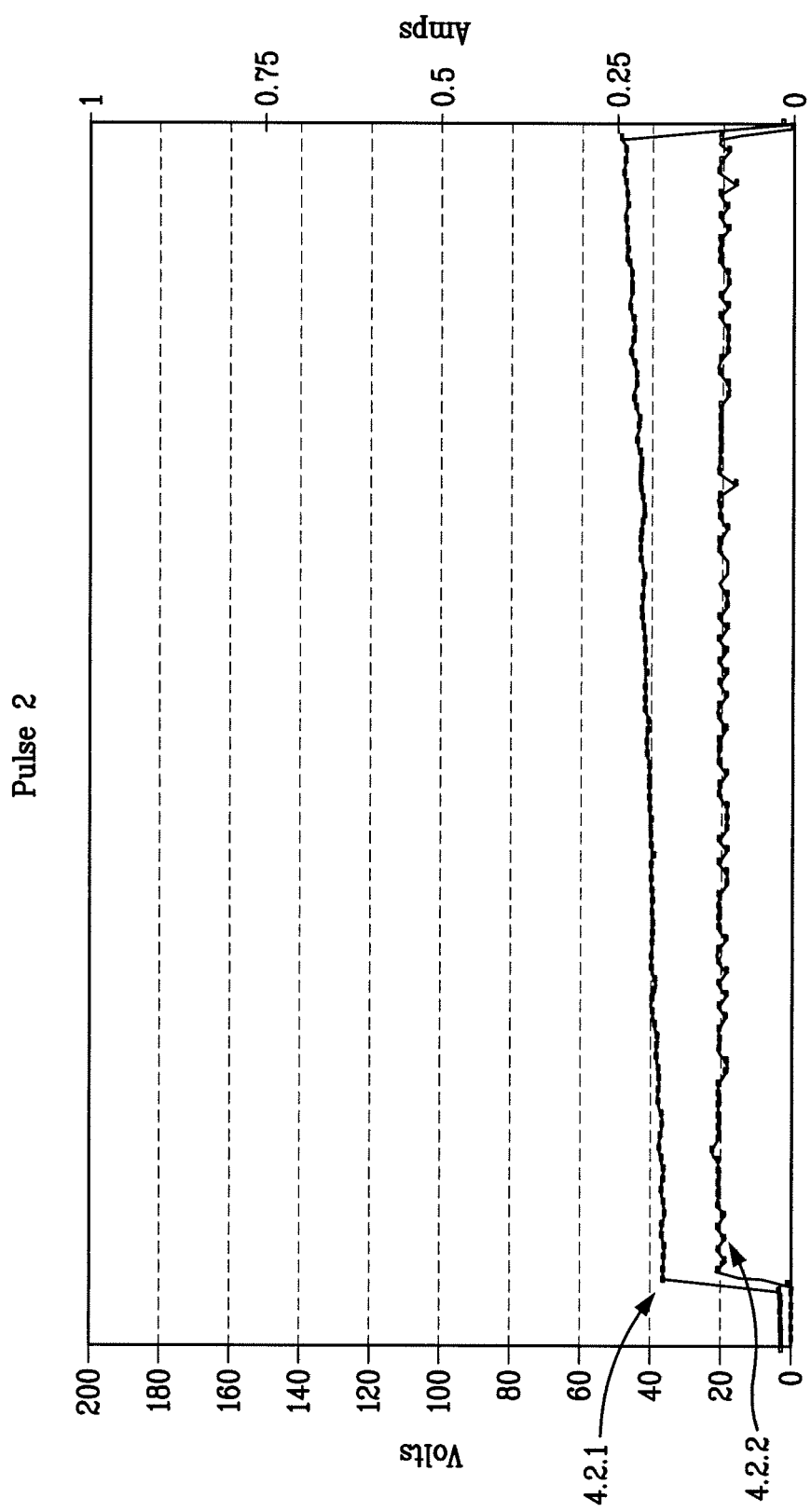
FIG. 4.2

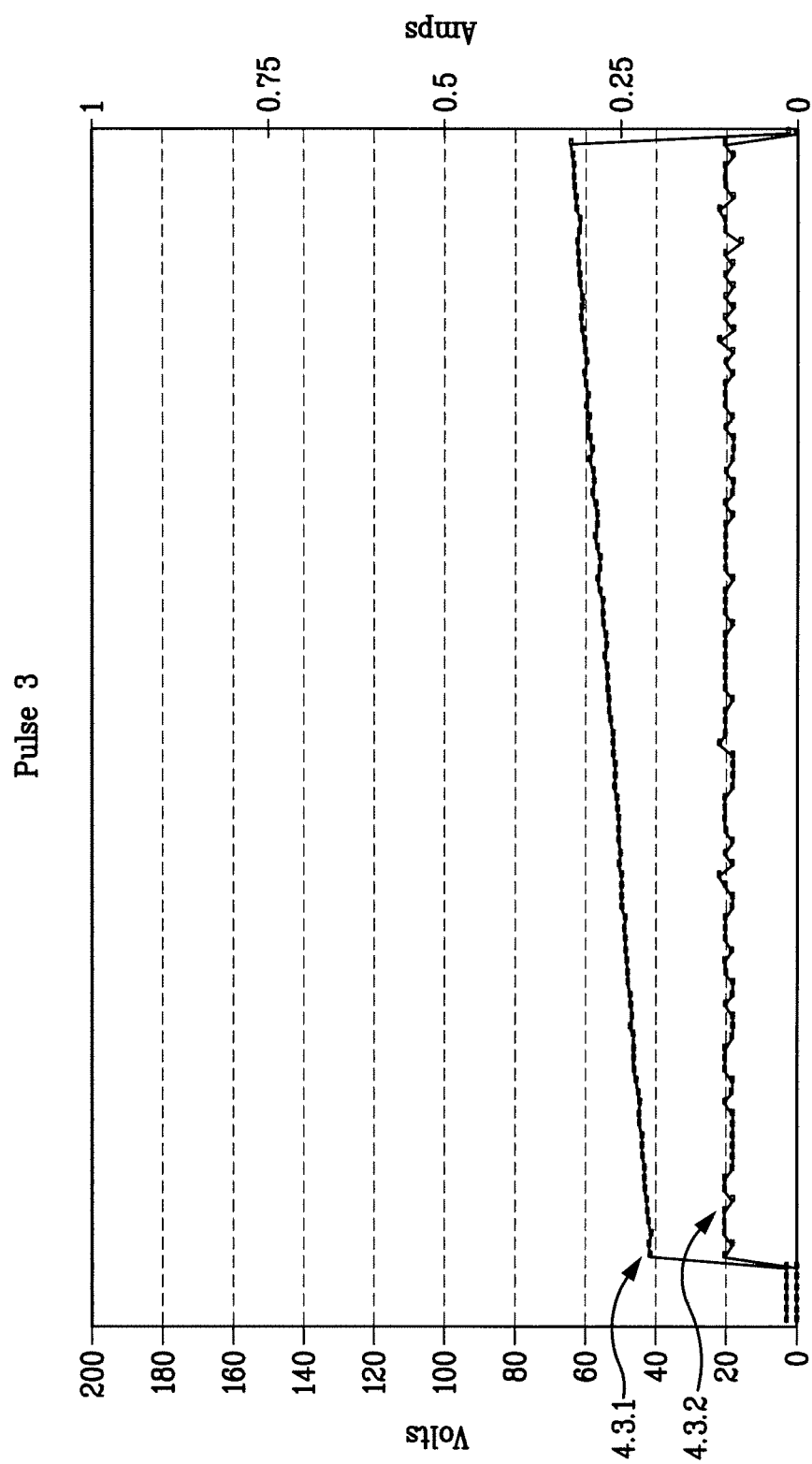
FIG. 4.3

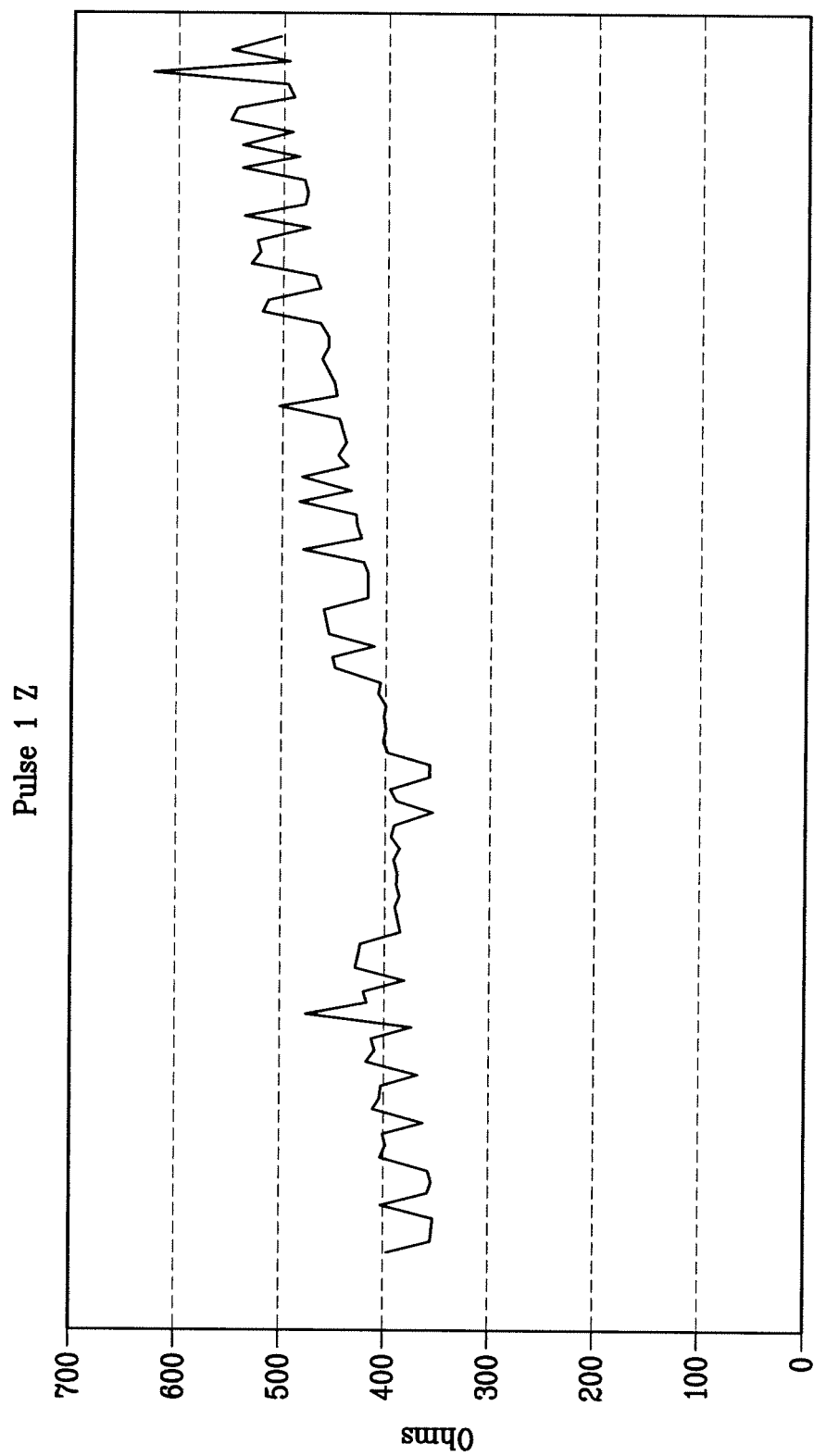
FIG. 4.4

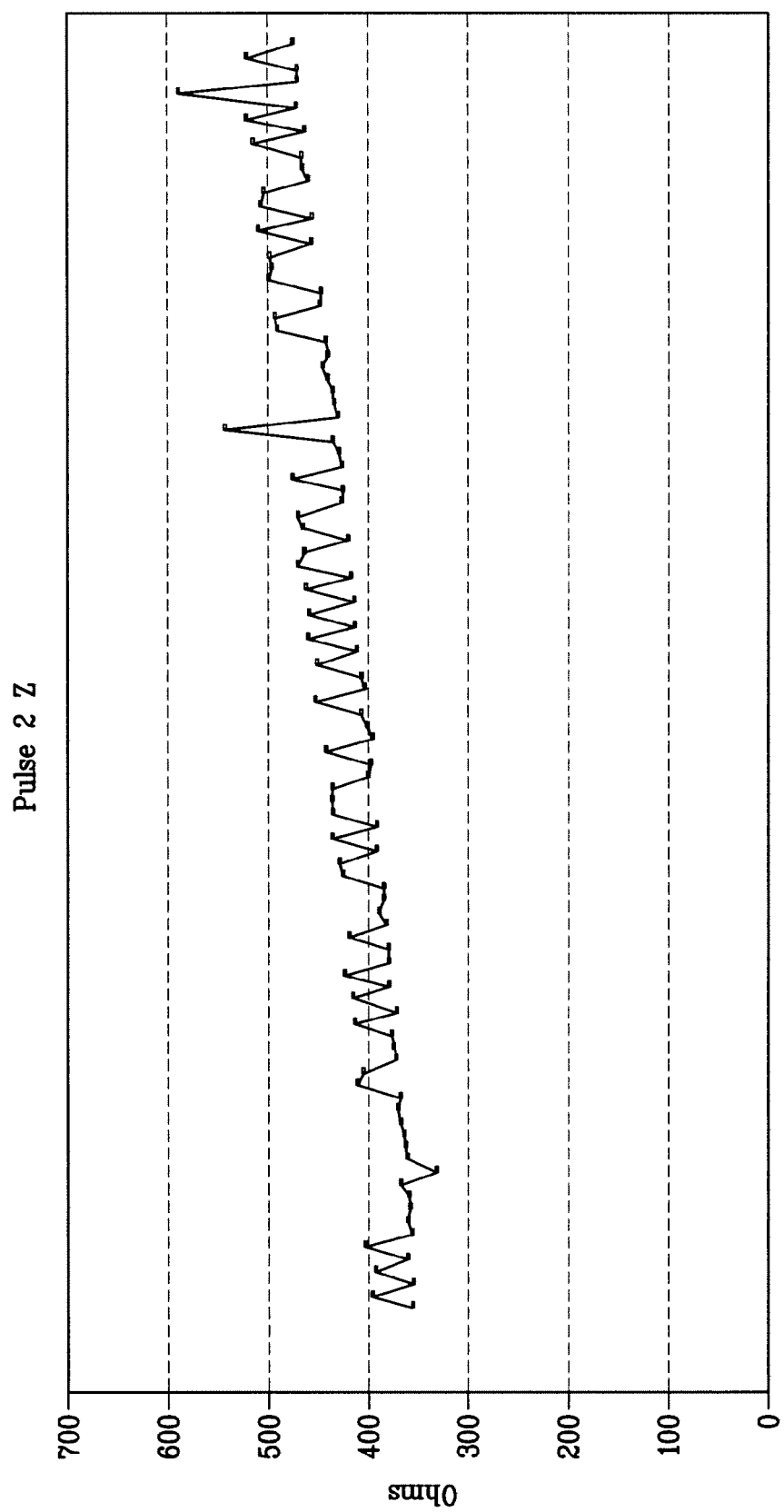
FIG. 4.5

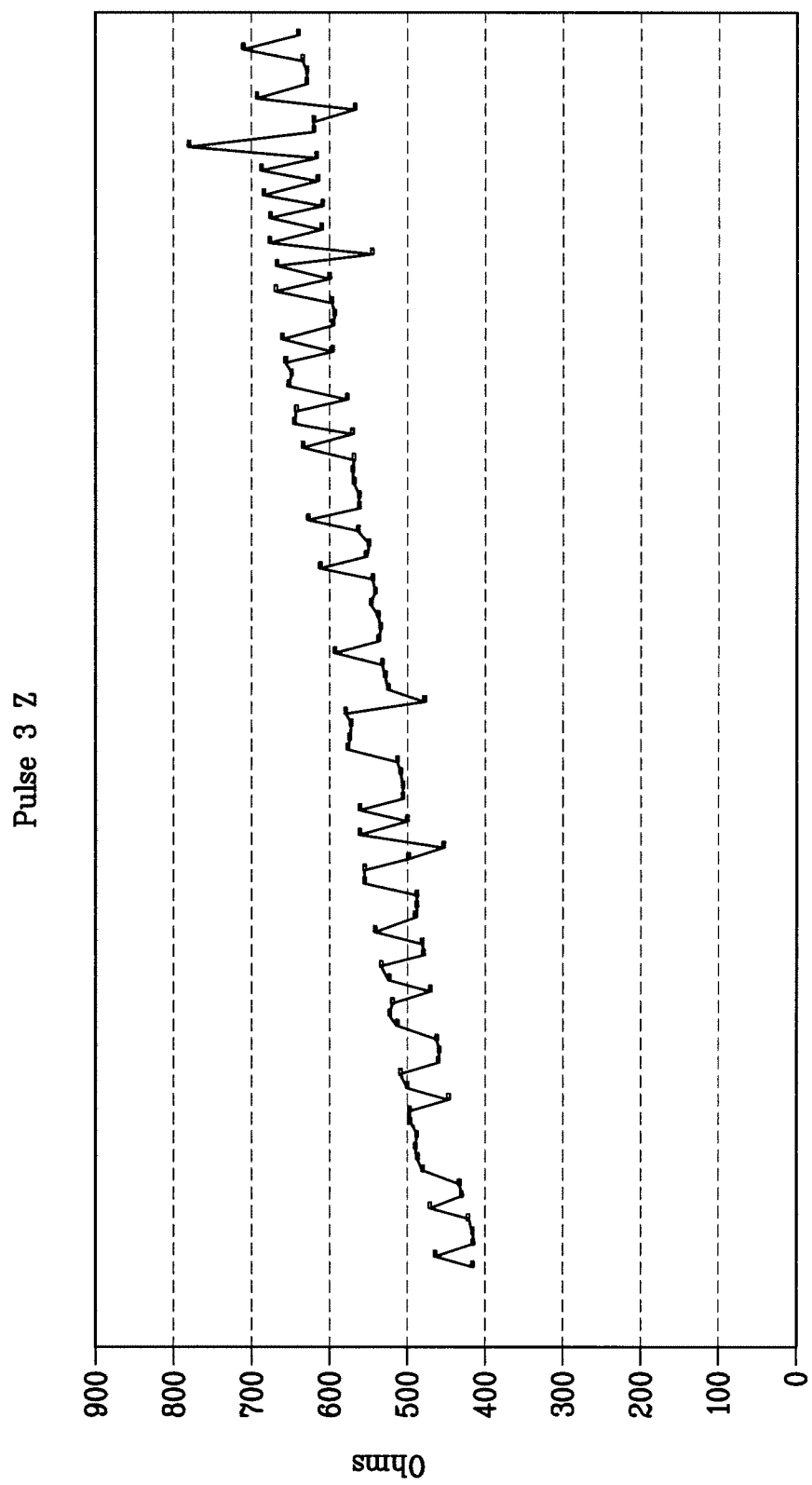
FIG. 4.6

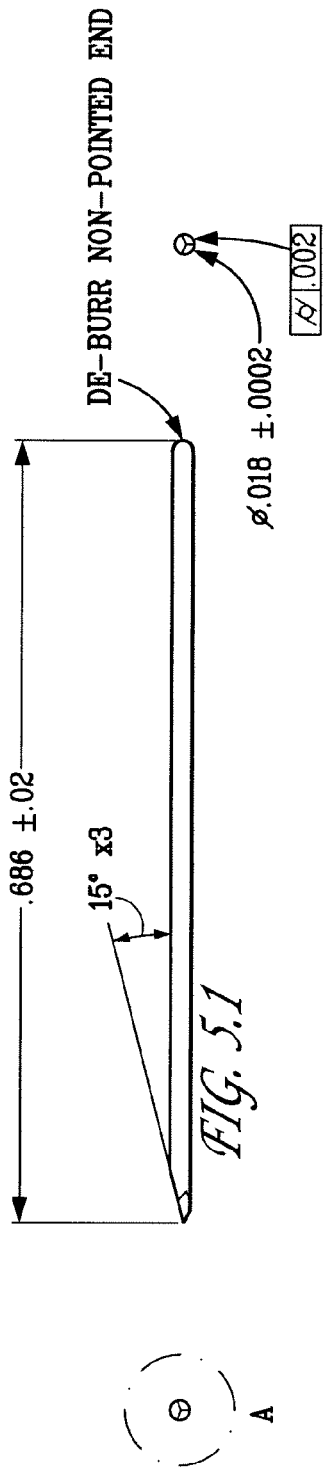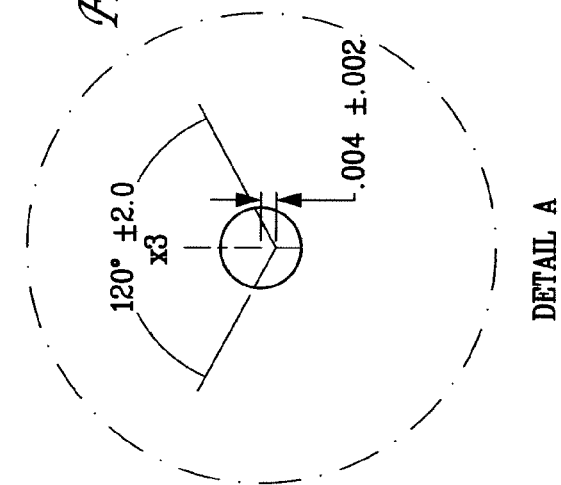
FIG. 5.1
FIG. 5.2
FIG. 5.3
DETAIL A
NOTES:
1. MATERIAL 304 SS, SPRING TEMPER, 26 GA SOLID
2. ULTRASONICALLY CLEAN FINISHED PARTS

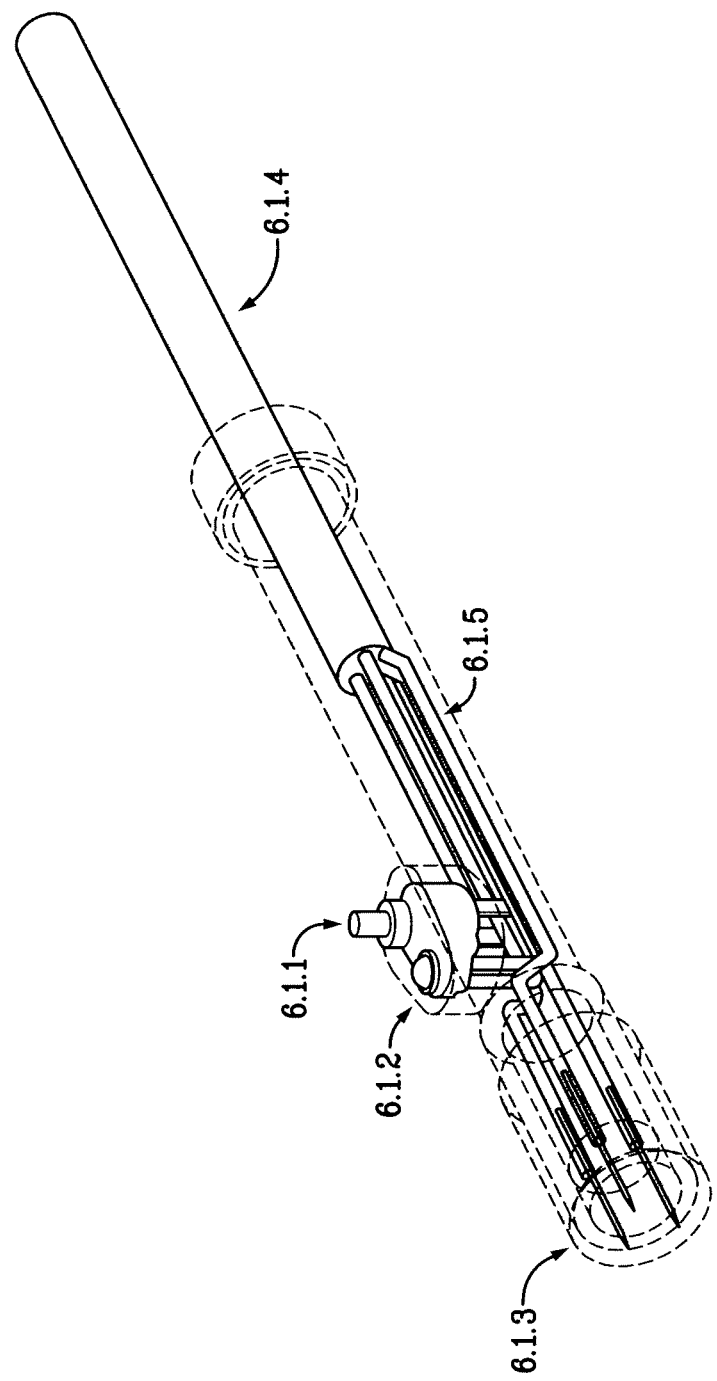
FIG. 6.1

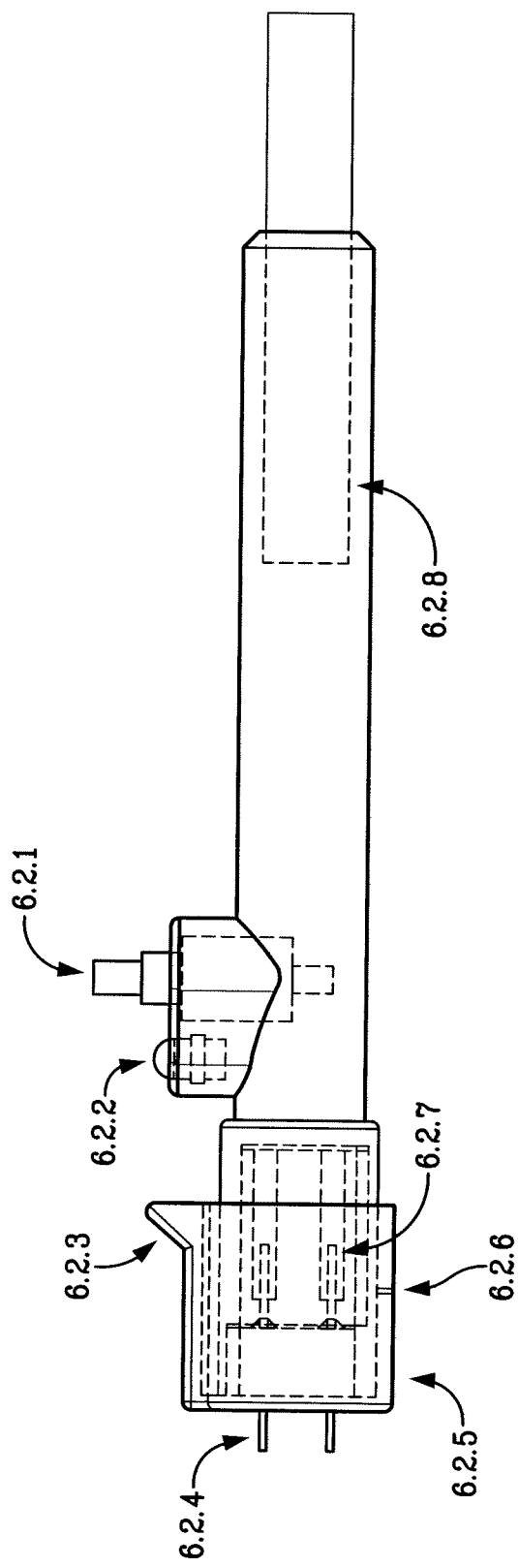
FIG. 6.2

| Dose (μg) | Volume (μL) | Current | Lag | Handle | Pulse | Score | SE Mean |
|---|---|---|---|---|---|---|---|
| 50 | 50 | 0.2A | 4 | MA | 20ms | 5.00 | 0.00 |
| 100 | 100 | 0.2A | 80 | LA | 20ms | 5.00 | 0.00 |
| 100 | 100 | 0.2A | 4 | LA | 20ms | 4.33 | 0.24 |
| 200 | 100 | 0.1A | 4 | LA | 52ms | 4.17 | 0.17 |
| 100 | 100 | 0.1A | 4 | LA | 20ms | 4.00 | 0.00 |
| 200 | 100 | 0.4A | 80 | LA | 52ms | 3.67 | 0.33 |
| 100 | 50 | 0.2A | 4 | LA | 52ms | 3.33 | 0.33 |
| 50 | 50 | 0.2A | 4 | MA | 52ms | 3.00 | 0.00 |
| 100 | 100 | 0.1A | 80 | LA | 52ms | 2.83 | 0.17 |
| 200 | 100 | 0.4A | 80 | MA | 20ms | 2.83 | 0.17 |
| 50 | 50 | 0.2A | 80 | LA | 20ms | 2.67 | 0.17 |
| 100 | 200 | 0.1A | 80 | MA | 20ms | 2.33 | 0.33 |
| 200 | 100 | 0.6A | 80 | LA | 52ms | 2.17 | 0.17 |
| 100 | 50 | 0.1A | 80 | MA | 52ms | 2.00 | 0.00 |
| 50 | 50 | 0.6A | 80 | MA | 52ms | 2.00 | 0.00 |
| 50 | 50 | 0.2A | 4 | MA | 20ms | 2.00 | 0.00 |
| 100 | 200 | 0.2A | 4 | LA | 20ms | 2.00 | 0.00 |
| 100 | 100 | 0.1A | 4 | LA | 20ms | 2.00 | 0.00 |
| 200 | 100 | 0.1A | 4 | LA | 52ms | 2.00 | 0.00 |
| 200 | 100 | 0.2A | — | LA | 52ms | 2.00 | 0.00 |

FIG. 10

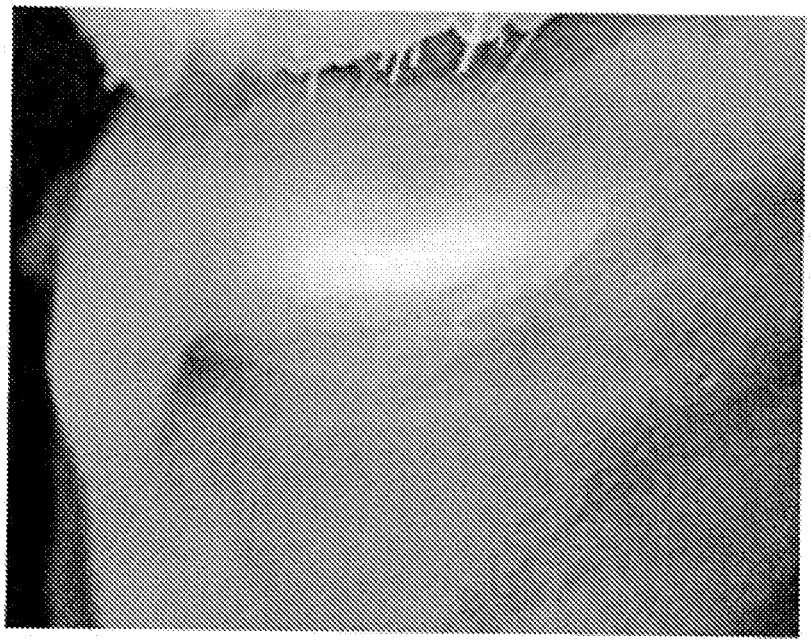
FIG. 15
50μg/50μL, skin EP
100μg/100μL, IM EP

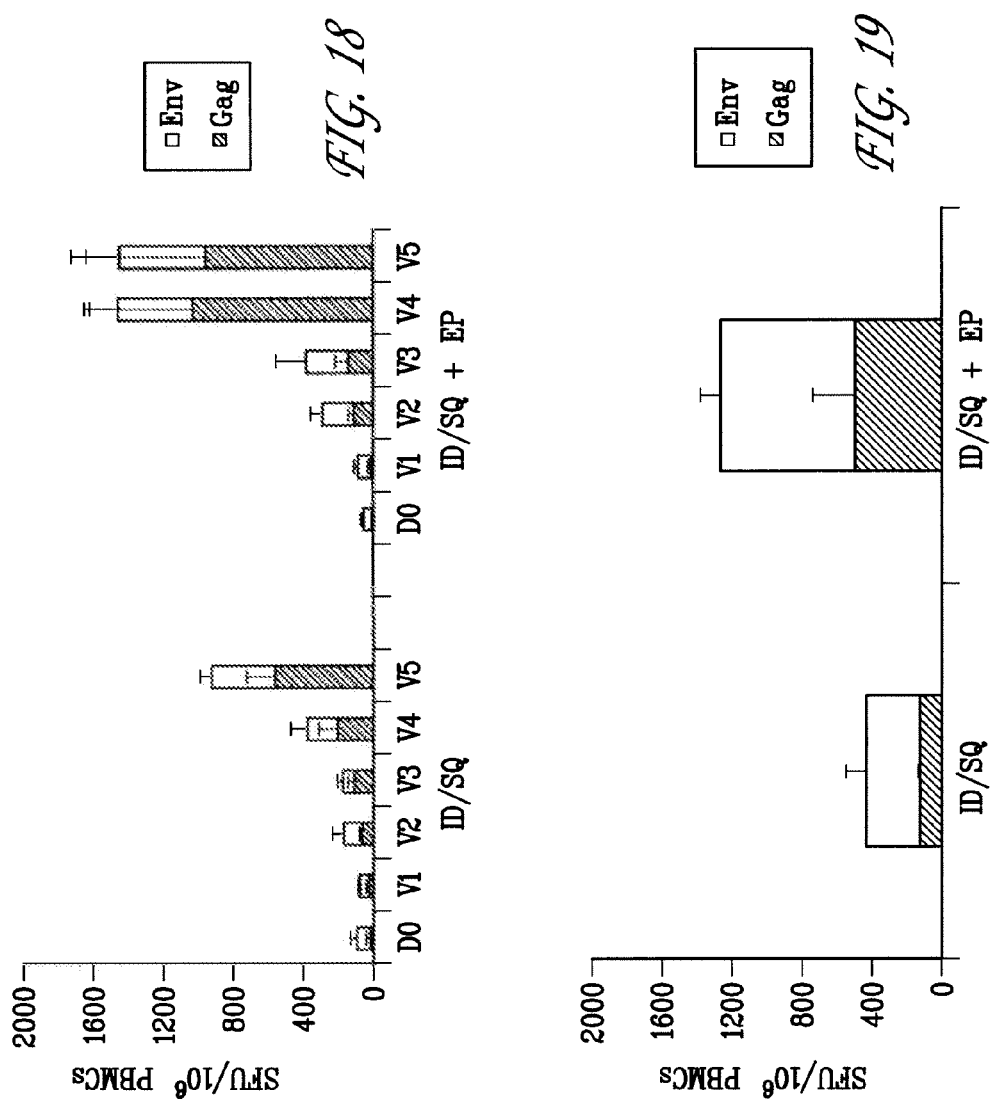

ELECTROPORATION DEVICES AND METHODS OF USING SAME FOR ELECTROPORATION OF CELLS IN MAMMALS

PRIORITY CLAIM

The present application claims priority to provisional applications U.S. Ser. No. 60/852,149, filed Oct. 17, 2006 and U.S. Ser. No. 60/978,982 filed Oct. 10, 2007.

FIELD OF THE INVENTION

The present invention relates to, among other things, electroporation devices and their use for facilitating the introduction of biomolecules into cells of a selected tissue in a mammal, preferably skin.

BACKGROUND OF THE INVENTION

Mammalian skin or skin tissue is characterized by layers of cells, divided into specific regions (see FIG. 1). The most superficial region is the epidermis (1.1), which in turn can be divided into 5 sub-layers: stratum corneum (1.1.1), stratum spinosum (1.1.2), stratum lucidium (1.1.3), stratum granulosum (1.1.4), and stratum basale (1.1.5). The dermis (1.2) is situated just under the epidermis, and is a very well vascularized region; hair roots and sweat glands are located in this layer. The subcutaneous layer is situated just underneath the dermis.

Skin has evolved to protect not only by acting as a physical barrier, but also by its role in the immune system. As a frontline of the host's defense against pathogens, skin is well equipped for immune surveillance. For example, compared to many other tissues, the epidermis of the skin contains a high population of Langerhans cells, which are very potent immature dendritic cells ("DC"). Thus, targeting antigens to the skin epidermis should be able to efficiently induce strong immune responses. However, the barrier posed by the stratum corneum layer (1.1.1) of the epidermis (1.1) (see FIG. 1) tends to prevent effective entrance of antigens into the epidermis. Dendritic cells are the main antigen-presenting cells in the skin. A high population of DC in the skin makes intradermic ("ID") immunization an attractive route.

In vivo plasmid transfer technology, particularly as it relates to the transfer of plasmids to intradermic ("ID") or subcutaneous ("SQ") tissue or cells, has traditionally been limited in scope because in vivo expression levels resulting from the naked DNA (plasmid) transfer have been low, with only fractions of those achieved by viral gene transfer. The doses of plasmid that can be delivered in a volume adapted for the ID or SQ is small compared to doses that can be used in intramuscular injections ("IM"). Numerous investigators have outlined the safety and toxicological concerns with injecting viruses as DNA vectors into animals and humans (Frederickson, et al., *Mol. Ther.* 8:8-10 (2003)). Consequently, direct injection of plasmid DNA has become a desired delivery technique, however, efficient delivery into cells and protein expression levels have been a challenge. Skeletal muscle cells have provided a main target for direct plasmid transfer for DNA vaccines and other applications (Prud'homme, et al., Curr. Gene Ther. 6:243-273 (2006)).

A recent advance for plasmid delivery in vivo has been that of electroporation ("EP"). EP is used for delivery of a large variety of molecules: from ions to drugs, dyes, tracers, antibodies, and oligonucleotides, to RNA and DNA (Gehl, Acta Physiol Scand. 177:437-447 (2003)). This process exposes the target tissue to a brief electric field pulse that induces temporary and reversible pores in the cell membrane. During the period of membrane destabilization, molecules such as plasmids may gain intracellular access. Previously, reports have shown that improvements in the EP process increases the efficacy of transfer and lowers the amount of plasmid needed to generate targeted levels of antigens in vivo by using a constant-current device (Draghia-Akli and Smith, Page 245 in *Gene Therapy—Therapeutic Mechanisms and Strategies*, N. S. Templeton and D. D. Lasic, eds. Marcel Dekker, Inc., New York. (2003)). Enhancement of plasmid delivery using EP allows the injected tissue to be used as a bioreactor for the high production and secretion of proteins into the blood stream, and/or antigen presentation. The expression levels are increased by as much as two to three orders of magnitude over plasmid injection alone, to levels comparable to those of adenoviral-mediated gene delivery and may in some cases reach physiological ranges.

Electroporation has become a useful tool for basic research, with application in the area of gene transfer and DNA vaccination. Electroporation has been used successfully to transfect tumor cells after injection of plasmid or to deliver the anti-tumor drug bleomycin to cutaneous and subcutaneous tumors in humans. Electroporation has been used in mice, rats, dogs, and pigs to deliver therapeutic genes that encode for a variety of hormones, cytokines, enzymes, or antigens. The numerous tissues and organs that have been targeted include liver, eye, testis, cardiac muscle, smooth muscle, tumors at different locations, and skeletal muscle.

One of the challenges of skin EP in large mammals and humans is the individual variation of skin thickness, as well as variation in skin thickness between different anatomical regions. For instance, skin thickness at the deltoid level in humans is approximately 2 millimeters ("mm"), while at the suprascapular level it is approximately 2.6 mm, at the waist it is approximately 1.7-1.9 mm and at the thigh it is approximately 1.6-1.7 mm. Skin is sensitive, thus electrodes have to also be adapted in gauge and configuration to create the least discomfort. While for therapeutic purposes a certain degree of discomfort is sometimes acceptable to patients during therapy, it has been suggested that only a relatively painless method can be used for prophylactic vaccination. Electrode array configuration and characteristics, and device pulse patterns, have to be adapted to this challenge. It is known that the maximum uniform electric field is generated during electroporation from approximately 2 mm beyond the tip of an electrode to a point one-third the electrode from its tip.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferentially 20 mm long and 21 gauge.

Broadly, electroporation is the use of a transmembrane electric field pulse to induce microscopic pathways (pores) in a bio-membrane. These pores are commonly called "electropores." Their presence allows biomolecules, ions, and water to pass from one side of the membrane to the other. Thus, electroporation has been used to introduce drugs, DNA or other molecules into multi-cellular tissues, and may prove to be effective for the treatment of certain diseases. However, the use of EP in living organisms has several problems, including cell death that results from generated heat and the inability of electropores to reseal. The beneficial effects of the drug or biomolecule are extremely limited in EP methods where excessive cell heating and cell death occurs.

To better understand the process of electroporation, it is important to look at some simple equations. When a potential difference (voltage) is applied across the electrodes implanted in a tissue, it generates an electric field ("E"), which is the applied voltage ("V") divided by the distance ("d") between the electrodes.

$$E=V/d$$

The electric field intensity E has been a very important value when formulating electroporation protocols for the delivery of a drug or biomolecule into the cell of the subject. The field intensity is inversely proportional to the distance between the electrodes in that given a voltage, the field strength increases as the distance between the electrodes is decreased. However, a caveat is that an electric field can be generated in a tissue with insulated electrodes (i.e. flow of ions is not necessary to create an electric field). Although not wanting to be bound by theory, it is believed that the flow of ions opens the electropores and allows movement of molecules into the cells of a subject during electroporation. The flow of electric charge in a conductor or medium between two points having a difference in potential is called the current. The current between electrodes is achieved by the ions or charged particles in the tissues, which can vary among tissues and patients. Furthermore, the flow of conducting ions in the tissue can change between electrodes from the beginning of the electric pulse to the end of the electric pulse.

When tissues have a small proportion of conducting ions, resistance is increased, heat is generated and cells are killed. Ohm's law expresses the relationship between current ("I"), voltage ("V"), and resistance ("R"):

$$R=V/I$$

The resistance in the tissue between two electrodes varies depending on the charged particles present therein. Thus, the resistance in the tissue changes from the beginning of the electric pulse to the end of the electric pulse.

Heating is the product of the inter-electrode impedance (i.e. combination of resistance and reactance and is measured in ohms), and is proportional to the product of the current, voltage and pulse duration. Heating can also be expressed as the square of the current, and pulse duration ("t", time). For example, during electroporation the heating or power ("W", watts) generated in the supporting tissue can be represented by the following equation:

$$W=I^2Rt$$

Broadly, metallic or dielectric electrodes are placed in contact with tissues and short pulses of predetermined voltages are imposed on the electrodes initiating the cells to transiently open membrane pores. The protocols currently described for electroporation are defined in terms of the resulting field intensities E, which are dependent on short pulses of voltage proportional to the distance between the electrodes, and regardless of current or tissue resistance. Accordingly, the resistance or heating cannot be determined for the electroporated tissue, which leads to varied success with different pulsed voltage electroporation protocols. Certainly, the difference in upper limit amplitudes of a voltage pulse between electroporation protocols that facilitate effective electroporation and electroporation protocols that cause the cells to die are very small. Additionally, a definite correlation has been observed between death of cells and the heating of cells caused by the upper limit amplitudes of the short voltage pulses. Thus, the overheating of cells between across electrodes serves as a principal cause for the ineffectiveness of any given electroporation voltage pulsing protocol. Furthermore, the current between electrodes serves as a primary determinant of the effectiveness of any given pulsing protocol, not the voltage across the electrodes.

When electricity is delivered to the cells of a subject, the dose of electricity can be accurately described in terms of charge ("Q"), which is the current ("I") and the time ("t"), according to the formula:

$$Q=It$$

If the current is not constant, Q represents the time integral of I. In this respect, charged particles, be they ions or molecules, behave in a similar fashion. For example, when silver ions are deposited on an electrode to define the standard unit of electrical charge (the coulomb), only the charge, as defined above, is of importance. A certain minimum voltage must be present to generate a current, but the quantity of ions deposited cannot be determined from a pre-determined voltage. Correspondingly, the quantity of charged particles delivered to cells in an electroporator cannot be derived from the voltage imposed on the electrodes.

The effectiveness of electroporation is limited by the fact that there is a threshold value for the pulse intensity below which electroporation does not occur, and an upper limit above which the cells are destroyed. Experimental evidence shows that the difference between the upper and lower limits is so small that it is very difficult to design effective pulsing protocols without undue experimentation. This makes use of the technique difficult, mostly when one targets tissues that inherently have a non-homogeneous cell composition, such as skin—cells in epidermis and dermis of different thickness and number of strata, fat, fascia, blood vessels of different dimensions from capillaries to small vessels; only a true software driven device capable of instantaneously analyzing the instant conditions variable from individual to individual and between locations on the skin surface of each individual and adapting the output to the specific conditions would fulfill these requirements. Also, the electrode should be adapted to the skin morphology and prevent tissue damage and bleeding.

References directed toward an electroporation apparatus illustrate the usefulness of both an electrode apparatus and an in vivo method of electroporation. Correspondingly there are many U.S. patents that claim either specific electrodes, or methods for electroporation. For example, U.S. Pat. No. 6,302,874 to Zhang, et al. describes a method and apparatus for electrically assisted topical delivery of agents for cosmetic applications. U.S. Pat. No. 5,676,646 to Hofmann, et al. teaches a flow through electroporation apparatus for implanting molecules into living blood cells of a patient. U.S. Pat. No. 6,241,701 to Hofmann, et al. and U.S. Pat. No. 6,233,482 to Hofmann, et al. describe a method and apparatus for electroporation mediated delivery of drugs and genes. More specifically, they describe a method and apparatus for electroporation therapy ("EPT") for treating tumors with a combination of electroporation and a chemotherapeutic agent to produce regression of tumors in vivo. U.S. Pat. No. 6,216,034 to Hofmann, et al. describes a method of programming an array of needle electrodes for electroporation therapy of tissue. U.S. Pat. No. 6,208,893 to Hofmann, et al. describes an electroporation apparatus with a connective electrode template. U.S. Pat. No. 6,192,270 to Hofmann, et al. describes an electrode assembly for an apparatus and a method of trans-surface molecular delivery. U.S. Pat. No. 6,181,964 to Hofmann, et al. describes a minimally invasive apparatus and method to electroporate drugs and genes into tissue. U.S. Pat. No. 6,150,148 to Nanda, et al. describes an electroporation apparatus for control of temperature during the process, by generating and applying an electric field according to a user-specified pulsing and temperature profile scheme. U.S. Pat. No. 6,120,493 to Hofmann, et al. describes a method for the introduction of therapeutic agents utilizing an electric field electroporation apparatus. U.S. Pat. No. 6,096,020 to Hofmann, et al. describes an electroporation method and apparatus for generating and applying an electric field according to a user-specified pulsing scheme. U.S. Pat. No. 6,068,650 to Hofmann, et al. describes a method of selectively applying needle array configurations for in vivo electroporation therapy, and U.S. Pat. No. 5,702,359 to Hofmann, et al. describes an electrode apparatus for the application of electroporation to a portion of the body of a patient with a sensing element for sensing a distance between the electrodes and generating a distance signal proportionate to the distance between said electrodes, and means responsive to said distance signal for applying pulses of high amplitude electric signal to the electrodes proportionate to the distance between said electrodes. U.S. patent Publication 2005/0070841 by Mathiesen, et al. discloses an electroporation device and injection apparatus. All of these cited patents are hereby incorporated by reference. Devices used in combination with the novel skin electrodes presented here, and used in the experiments described herein are claimed in U.S. patent Publication 2004/0167458 and U.S. Patent Pub. 2005/0052630, the entire content of each of which is hereby incorporated by reference.

Progress in the enhancement of plasmid expression in vivo and the achievement of physiological levels of a secreted protein has been recently reported using electroporation (Draghia-Akli, et al., Technology in Cancer Research & Treatment 1:365-371 (2002)). Studies show that injection of a plasmid that expresses growth hormone releasing hormone ("GHRH"), followed by electroporation, is scalable and represents an approach for stably producing secreted proteins for treating large mammals (Draghia-Akli, et al., Journal of Animal Science 81:2301-2310 (2003); Draghia-Akli, et al., FASEB J 17:526-528 (2003)). Still, additional improvements in electroporation techniques are needed, in particular for efficient skin electroporation for vaccination purposes and gene therapy, and electroporation with reduced invasiveness and pain.

Previous investigators have utilized electroporation devices for plasmid DNA transfer that are conceptually based on constant voltage systems, utilizing a predetermined voltage between the electrodes. Because the impedance between electrodes that are embedded in a tissue can vary from case-to-case, or tissue-to-tissue, a predetermined voltage does not produce a predetermined current. A predetermined voltage pulse causes an unregulated increase in the current flowing through a muscle tissue during the duration of the pulse in addition to the loss of the perfect square wave function. By contrast, a constant-current source actually maintains a square wave function constant current through muscle tissue. However, the existing commercial electroporation devices do not have the firmware designed to enable measurement of the exact amount of current to which the cells are exposed. The unregulated current generated with conventional electroporation devices may generate amounts of heat in tissues that can easily kill cells. For example, a typical electronic 50 milliseconds (ms) pulse with an average current of 5 Amperes ("A," or "Amp") across a typical load impedance of 25 ohms ("Ω") can theoretically raise the temperature in tissue 7.5° C., which is enough to kill cells. The physics of tissue injury caused by electrical shock is reviewed by Lee, et al. (Lee, et al., Annu. Rev. Biomed. Eng 2:477-509.:477-509 (2000)). Thus, there is a need to avoid the technological problems associated with constant voltage electroporation by providing a means to control effectively the amount of electricity delivered to the cells and thereby achieve proficient electroporation while limiting the destruction of cells.

The difficulties present in many electrodes stem from the fact that the pulse energy is concentrated in the center of the array, the point where the material to be transfected is deposited. As a result, the spatial distribution of energy delivery assumes a very non-uniform character. Therefore, only a fraction of the cells in the volume encompassed by the electrode assembly is electroporated. Thus, there is also a need for some applications to provide a means to effectively control the dosage of electricity delivered to the cells in the inter-electrode space by precisely controlling the ionic flux that impinges on the conduits in the cell membranes. Also, commercially existing electrodes for large animal applications and humans generally do not allow for ID or SQ targeting of dendritic cells, as they are typically too long, of an inappropriate gauge and improper bevel orientation. Thus, there is a need for certain applications for a skin electroporator, facilitating the in vivo delivery of a biomolecule, such as a plasmid, into skin tissue, e.g., ID or SQ spaces in an animal.

Furthermore, commercially available electroporation devices and needle arrays typically do not permit for control of inter and intra-individual variation of tissue resistance, thickness and local conditions. With these instruments, a predetermined voltage is delivered through the electrodes irrespective of the individual tissue resistance or thickness. Thus, there is also a need for an electroporation device and skin electrodes that permits adapted electroporation that accounts for the individual variation before and during the pulses.

In addition, electroporation devices which use skin and muscle invasive replaceable needle arrays as electrodes to deliver the electric current require maintenance of sterile conditions when the needle array replacement occurs. This is necessary from both a medical practice and regulatory compliance viewpoint. In the same time, a disposable skin electrode is needed to allow for lower production costs and usage in mass vaccination of both therapeutic and prophylactic purposes. Thus, there is also a need to provide a skin electrode disk that allows easy replacement of the needle skin array.

SUMMARY OF THE INVENTION

In one aspect of the present invention, provided are electroporation devices that effect electroporation in tissue of a mammal by delivering a constant current to the tissue, the tissue preferably being skin tissue. In some embodiments, the electroporation devices are configured to deliver to a desired tissue of a mammal a pulse of energy producing a constant current similar to a preset current input by a user. The electroporation device comprises an electroporation component and a skin electrode assembly. The electroporation component is capable of delivering the pulse of energy that produces the constant current in the desired tissue, and includes a feedback mechanism. The skin electrode assembly includes an electrode array having a plurality of skin electrodes in a spatial arrangement, wherein the skin electrode assembly receives the pulse of energy from the electroporation component and delivers same to the desired tissue through the skin electrodes. At least one of the plurality of skin electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In one aspect of the present invention, provided are electroporation handle assemblies configured to deliver a pulse of energy to a desired tissue of a mammal to produce a constant current in the desired tissue similar to a preset current input by a user. The handle assembly comprising a skin electrode array having a plurality of skin electrodes in a spatial arrangement, wherein at least one of the skin electrodes is neutral during delivery of the pulse of energy and measures impedance in the desired tissue; a controller in communication with the skin electrode array, the controller controlling delivery of the pulse of energy through the skin electrodes; and a means for performing a feedback mechanism, wherein the feedback mechanism is performed by software or hardware, which receives the measured impedance from the neutral skin electrode and adjusts the pulse of energy delivered, if needed, to maintain the constant current.

In one aspect of the present invention, provided are methods of using the electroporation devices of the present invention to deliver biomolecules to cells of a tissue of a mammal. In some embodiments, the methods comprise using the skin electroporation devices described herein to deliver the pulse of energy to the desired skin tissue to produce the constant current similar to a preset current input by a user. The methods include: inserting a plurality of needle skin electrodes into skin tissue without substantially penetrating a muscle tissue; and applying the pulse of energy to the plurality of needle skin electrodes to deliver a current equal to the preset current in the skin tissue; and measuring impedance of the skin tissue with a neutral one of the plurality of needle skin electrodes and using a feedback mechanism in the electroporation device to adjust the pulse of energy applied in response to the measured impedance to maintain the current delivered to the skin tissue constant.

In some embodiments of the present invention, provided are methods comprising the steps of: providing an skin electrode assembly having a plurality of needle skin electrodes, the skin electrode assembly in electrical communication with a current waveform generator; contacting skin tissue of a mammal with the plurality of needle skin electrodes without substantially penetrating a muscle tissue of the mammal; and applying an electrical pulse of energy from the current waveform generator to the plurality of needle skin electrodes for a time and under conditions effective to expose the contacted skin tissue to a substantially constant current.

BRIEF DESCRIPTION OF THE DRAWINGS

The numerous objects and advantages of the present invention may be better understood by those skilled in the art by reference to the accompanying figures, in which:

FIG. 2C shows an example of an actual pulse sequence recording downloaded at the end of the pulse sequence, using the skin EP device as a pulse generator, and the described skin electrode array to deliver the electric pulses after plasmid formulation injection into the ID and SQ layers of skin in a 25 kg pig: ("2.1") shows the file name that has been downloaded via the infrared port onto a personal computer or hand-held device; ("2.2") shows the subject number, as entered directly into the skin EP device through the numerical pad, as a prerequisite condition before the EP process could start; ("2.3") shows the characteristics of the electric pulses selected by the operator, including the number of pulses in the pulse sequence, wait time before and between pulses (in seconds, "s"), the pulse width (in milliseconds, "ms"), the pulse current amplitude (in amperes, "A"); ("2.4") shows the electrical charge of each electrode during each pulse—for each of the skin electrodes 1, 2, 3 any of the following positions is possible: positive, "pos"; negative, "neg"; or off "off"—the "off" electrode(s) are importing back information into the device before, during and after each pulse ("feed-back"); ("2.5") shows the actual amperage ("A"), voltage ("V") and skin tissue resistance, Z, at the injection area ("Ohms") during each pulse of the pulse sequence; as the feed-back arises every 0.1-0.2 ms (and in this case the pulses were 52 ms in length), only a small proportion of the feed-back file has been included, for example purposes;

FIG. 3 shows an example of the graphical display of downloaded data when using a skin electrode delivery of electric pulses by the skin EP device. The graph depicts both the voltage ("3.1.1") and current ("3.1.2") as measured by the skin EP device in Pulse 1 ("3.1") as well as the voltage ("3.2.1") and current ("3.2.2") as measured by the skin EP device in Pulse 2 ("3.2"). The tissue resistance (as measured during the electric pulses) is also displayed for Pulse 1 ("3.3") and Pulse 2 ("3.4");

FIG. 4 shows an example of the graphical display of downloaded data when using a large electrode array delivery of electric pulses by the skin EP device to the skin. The graph depicts both the voltage ("4.1.1") and current ("4.1.2") as measured by the skin EP device in Pulse 1 ("4.1"), the voltage ("4.2.1") and current ("4.2.2") as measured by the skin EP device in Pulse 2 ("4.2"), and the voltage ("4.3.1") and current ("4.3.2") as measured by the skin EP device in Pulse 3 ("4.3"). The tissue resistance (as measured during the electric pulses) is also displayed for Pulse 1 ("4.4"), Pulse 2 ("4.5") and Pulse 3 ("4.6");

FIG. 5 shows a schematic representation of a skin electrode array, including detailed characteristics: ("5.1") side view depicting length and angle of insertion end of a single needle-electrode; ("5.2") front view depicting angles and degrees for revere-trochar point; ("5.3") notes indicating needle-electrode specifications;

FIG. 6 shows a visual representation ("6.1") and schematics ("6.2") of the skin electrode handle: ("6.1.1") trigger used to activate the impedance check and then electroporation sequence; ("6.1.2") "LED" displays green or red when the skin EP device is ready to treat or during an error, respectively; ("6.1.3") skin electrode array locked into place; ("6.1.4") cord containing individual wires and signals between the skin electroporation handle and skin EP device unit; ("6.1.5") individual wires whose detail is depicted in electrical wiring diagram in FIG. 8; ("6.2.1") trigger schematic; ("6.2.2") LED schematic; ("6.2.3") schematic depicting the raised ridge on the skin electrode array used to facilitate ejection from the skin electrode handle following completion of electroporation pulse sequence; ("6.2.4") schematic of needle-electrodes of skin electrode array; ("6.2.5") side view schematic of skin electrode array locked into place on handle; ("6.2.6") schematic of locking arm and detent (on handle); ("6.2.7") schematic depicting sockets inside skin electrode handle used to receive and make contact for circuit connection; ("6.2.8") schematic depicting cord housing individual wires whose detail is shown in FIG. 8;

FIG. 10 shows the average expression levels of GFP in animals which were injected with different amounts of the plasmid pSP5-12-GFP and electroporated with the skin EP device using the skin electrodes array and skin specific EP conditions (MA), compared to electrodes and conditions usually employed for plasmid delivery to the skeletal muscle (LA).

FIG. 15 displays fluorescent images that represent green fluorescent protein expression after ID/SQ plasmid administration followed by electroporation (EP) in pig skin. Plasmids were delivered at different doses and volumes with either the larger EP array customary used for IM+EP (A), or the skin EP (B).

FIG. 17 illustrates non-human primate study design.

FIG. 18 displays a graph showing enhanced cellular immune responses to HIV-1 immunogens with ID/SQ co-injection of plasmid encoded IL-12 followed by EP. IFNγ ELISpots were performed two weeks after each immunization. Responses to env are depicted as white bars and gag are depicted as black bars with the data shown as stacked group mean responses±SEM.

FIG. 19 displays a graph showing enhanced memory responses to HIV-1 immunogens with ID/SQ EP. Ten weeks after the last immunization, ELISpot assays were performed to determine antigen-specific memory responses to gag and env in the ID/SQ and ID/SQ+EP groups. The data are shown as group mean responses±SEM.

ELISpot was performed at week 10 to assess the induction of a gag or env-specific $T_H2$ response. Responses to env are depicted as white bars and gag are depicted as black bars with the data shown as stacked group mean responses±SEM.

Figure 21:
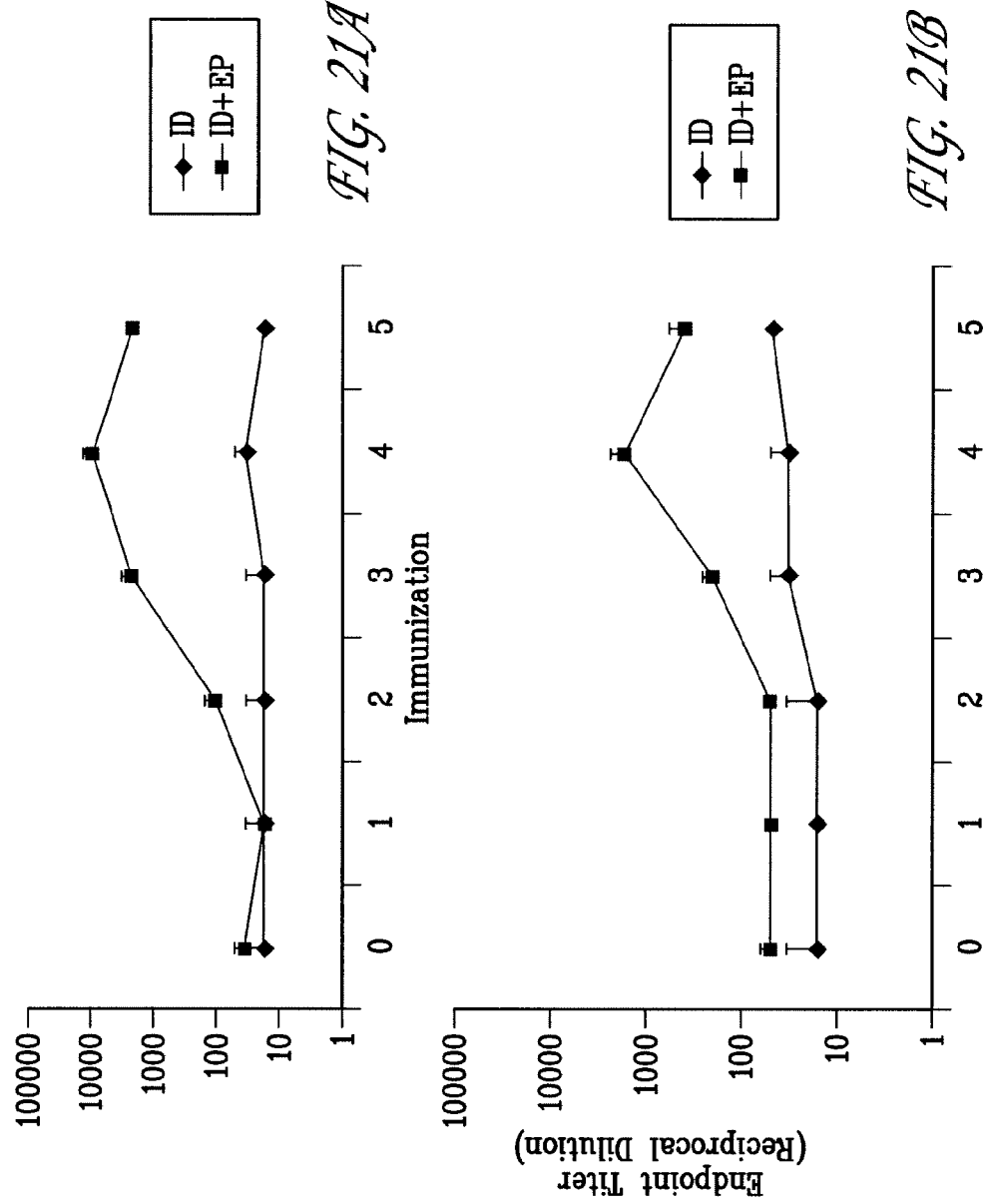

FIG. 21 displays a graph showing induction of p24 (21A) and gp160 (21B) antibodies. Serum was collected at weeks 0, 4, 8, 12, and 18. Gag and env antibody titers were determined by p24 and gp160 ELISA, respectively, in the ID/SQ and ID/SQ+EP immunized groups. The data are shown as group mean responses±SEM.

Figure 22:
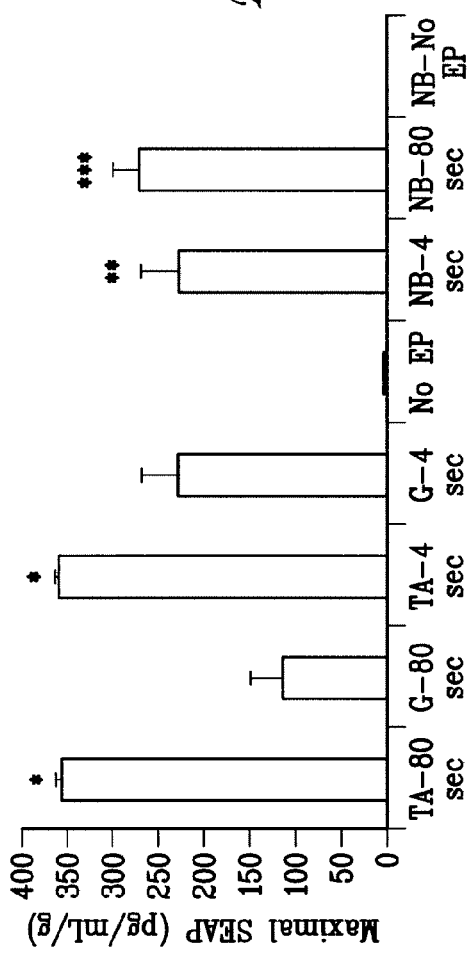

FIG. 22 displays bar graphs showing SEAP expression measured in different muscles in mice. Mice were injected with 10 μg C5-12-SEAP plasmid in the tibialis anterior (TA) muscle or gastrocnemius (G) muscle and EP after either 4 s or 80 s delay. Mice were also injected with 10 μg pf C5-12-SEAP plasmid without EP (no EP). Serum SEAP levels were higher in TA muscle and G muscle injected mice compared to control mice that received the plasmid without EP (*P<1.3 E−21). Mice injected with the expression cassette without the plasmid backbone (NB) and then electroporated had higher SEAP levels than NB group without EP. However, the NB groups were significantly lower than mice administered C5-12-SEAP in the identical muscle (NB 4 s compared to TA 4 s P<0.008; NB 80 s compared to TA 80 s P<0.004). Mice injected into the TA muscle yield higher expression than animals injected into the G muscle and lowering the delay between injection and EP in the TA muscle from 80 s to 4 s did not affect expression.

Figure 23:
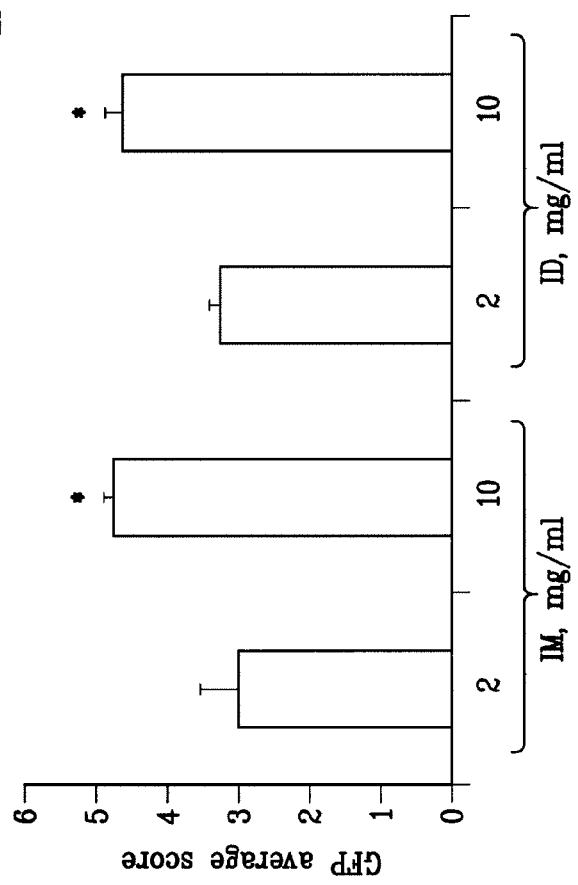

FIG. 23 displays bar graphs showing average GFP expression quantified in mice after intramuscular (IM) or intradermal (ID) injection of 50 μg of CMV-EGFP plasmid at concentrations of 2 mg/mL or 10 mg/mL in a total volume of 25 or 5 μL, respectively. GFP expression was highest in groups administered 10 mg/mL concentration as compared to animals administered 2 mg/mL concentration (ID and IM, *P=0.01), although ID and IM injection sites yielded similar overall scores when compared to each other.

Figure 24:
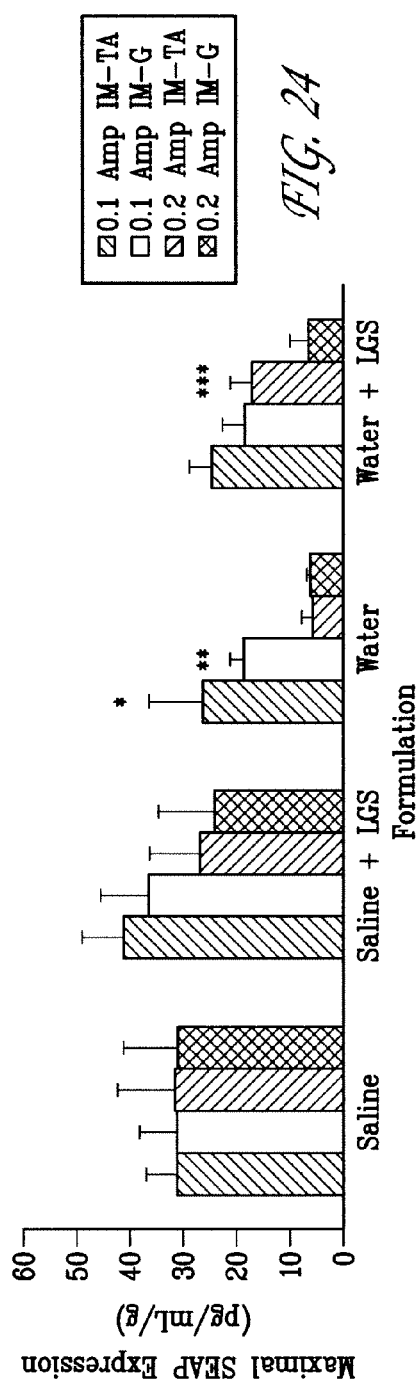

FIG. 24 displays bar graphs showing SEAP expression, which was driven by the ubiquitous CMV promoter, measured in different muscles in mice under various current settings. The plasmid formulation was tested: saline, saline+LGS, water, or water+LGS. Saline+LGS formulation at 0.1 A in the TA muscle yielded the highest expression. Animals receiving plasmid formulated into water and electroporation at 0.2 A yielded significantly lower SEAP levels than those receiving 0.1 A for the same muscle (*P<0.05 for TA and P<0.001 For G). When water+LGS was used as the plasmid formulation, the differences in serum SEAP levels were not significant for the TA muscle, but were for the G muscle (*P<0.04).

Figure 25:
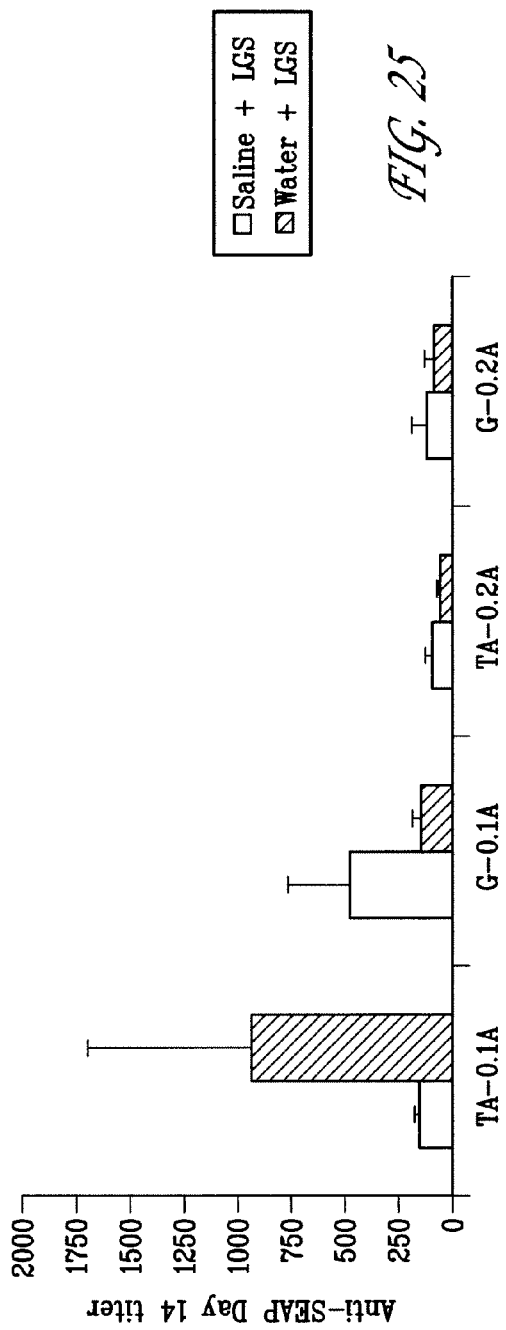

FIG. 25 displays titers for anti-SEAP antibodies measured 14 days post-treatment, which were highest in mice treated with 0.1 A of current in the G muscle when plasmid was formulated in (A) saline+LGS and in the TA muscle when formulated in (B) water+LGS.

Figure 26:
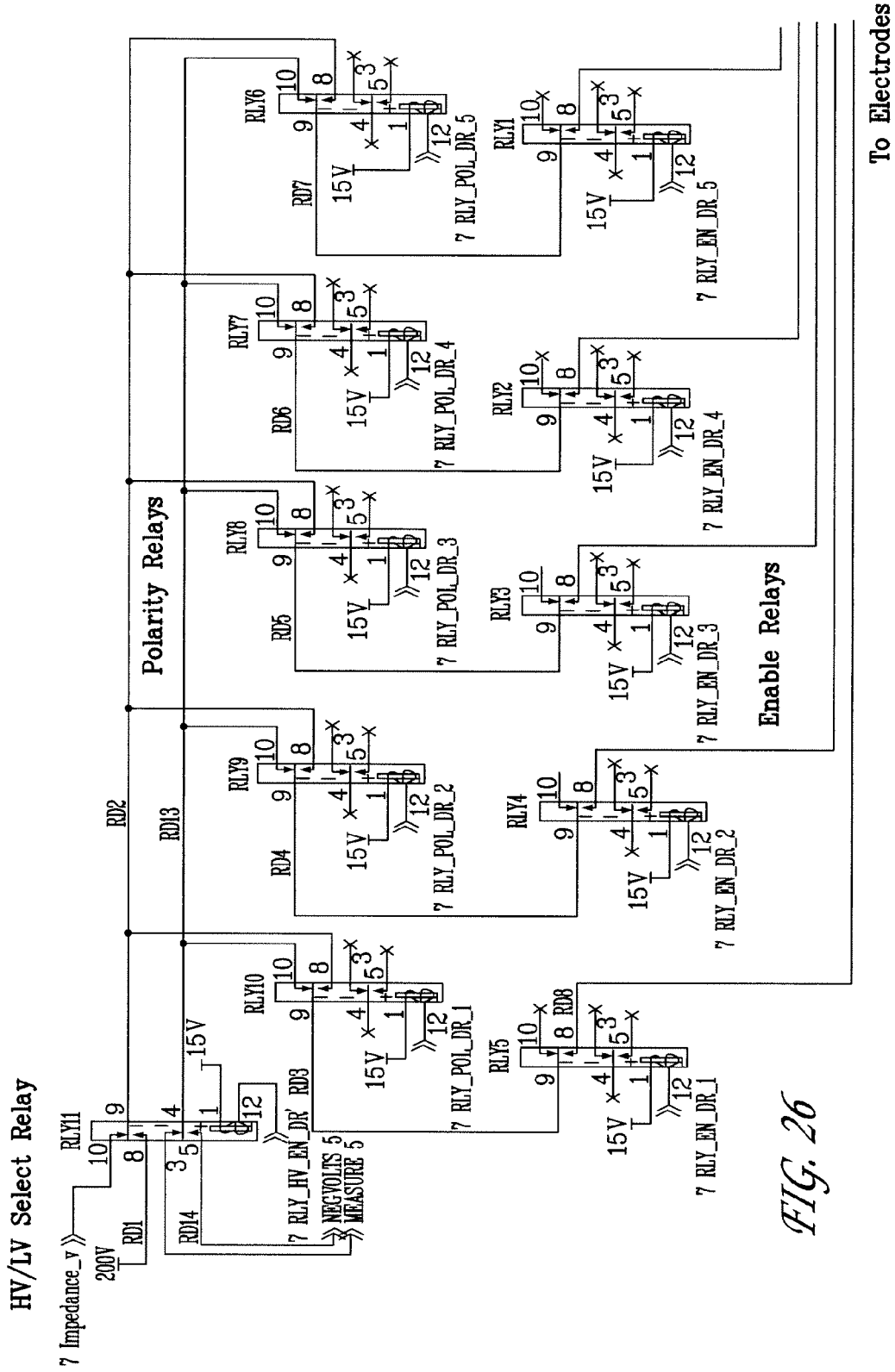

FIG. 26 displays a schematic of one embodiment of a relay contact matrix.

Figure 27A:
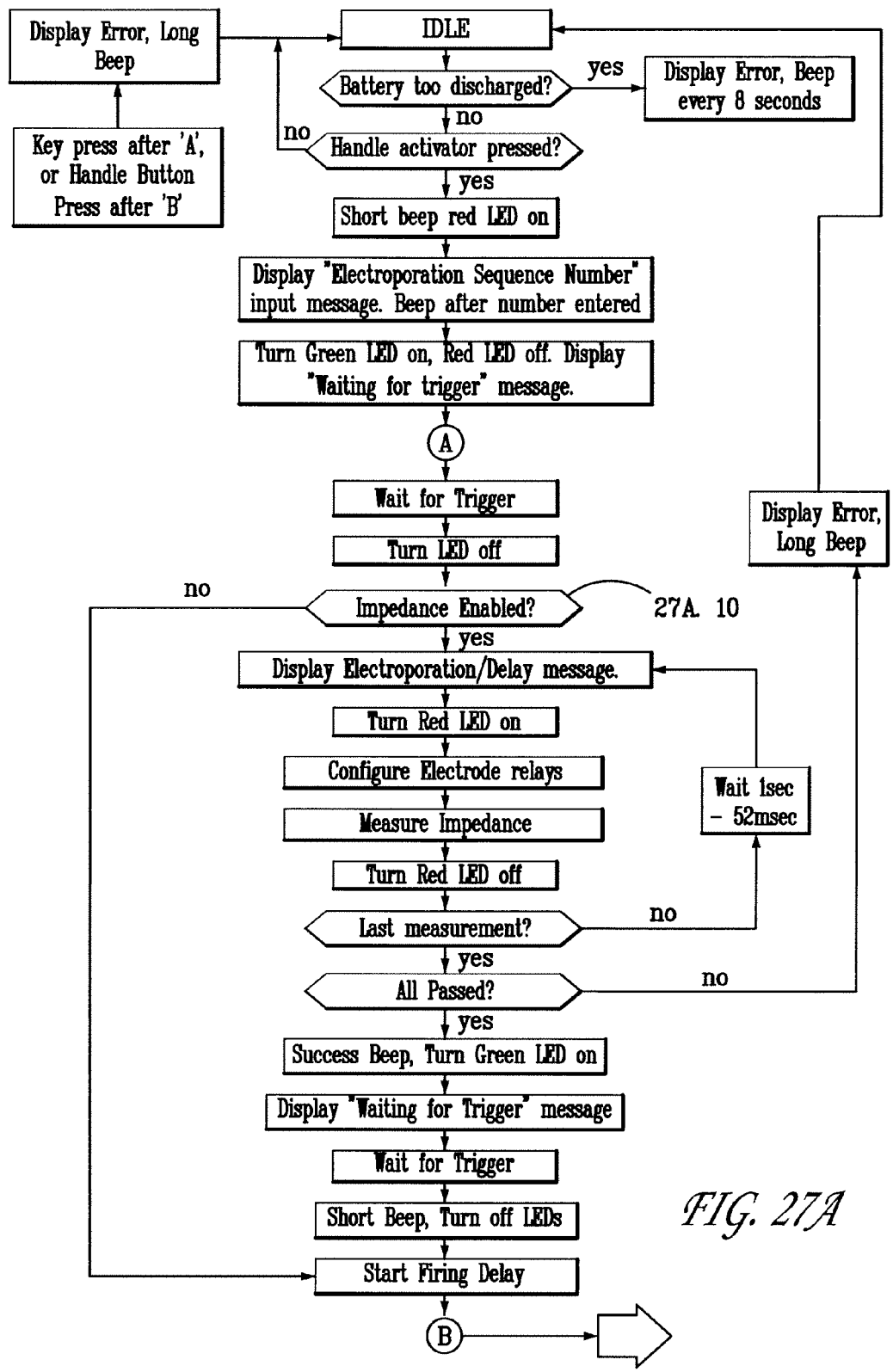

FIG. 27A displays a first part of a flowchart of the electroporation functional flow.

Figure 27B:
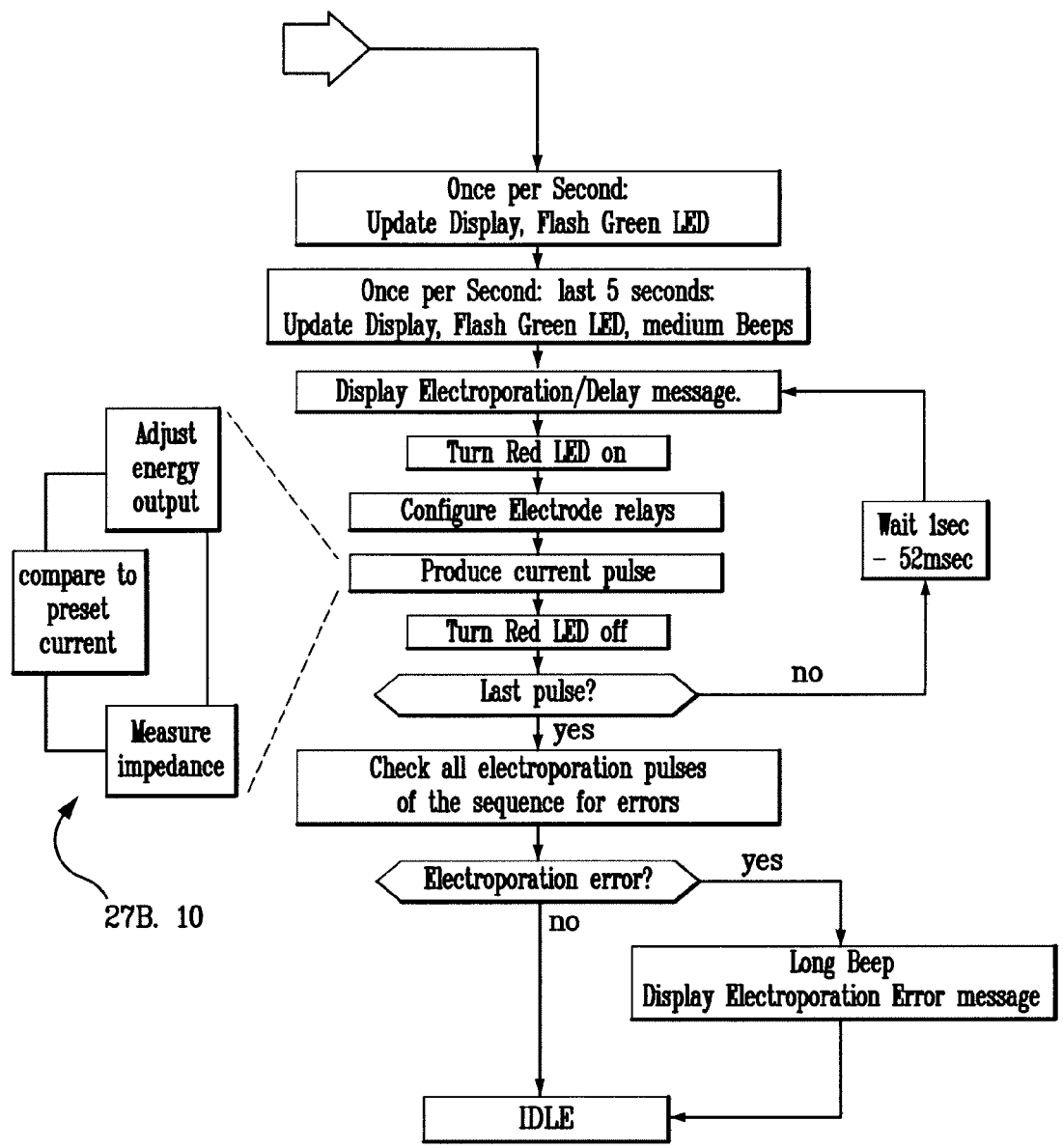

FIG. 27B displays a second part of the flowchart of the electroporation functional flow.

DETAILED DESCRIPTION OF PREFERRED EMBODIMENTS

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided skin EP devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the skin EP device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The term "biomolecule" as used herein refers to nucleic acid sequences, proteins, lipids, microbubbles (e.g. drug-loaded vesicles), and pharmaceuticals.

The terms "electroporation," "electro-permeabilization," or "electro-kinetic enhancement" ("EP") as used interchangeably herein refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "skin region" (or "skin tissue") as used herein refers to skin tissue, dermis, subdermis, and intradermic ("ID"), intracutaneous, subcutaneous ("SQ") layers or spaces. The skin region does not include muscle tissue.

The term "without substantially penetrating" as used herein refers to penetration of no more than about 1 mm to 2 mm by an object (e.g., needle) of interest, and preferably no more than about 5 mm.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

One aspect of the current invention is related to the electroporation devices of the present invention and their ability to deliver a pulse of energy to a desired tissue of a mammal and maintain a constant current therein, the tissue being preferably intradermic or a subcutaneous tissue. Preferably, electroporation devices are skin electroporation devices ("skin EP devices"). The skin EP devices can preferably penetrate the skin tissue without substantially penetrating a muscle tissue during EP. The devices deliver the pulse of energy through skin needle electrodes which can penetrate skin tissue, e.g., intradermic and subcutaneous tissue, and deliver the pulse of energy and maintain the constant current in the tissue over the duration of the pulse of energy and the entire electroporation process. The responsiveness of the presently described skin EP device that maintains the constant current in the treated tissue is accomplished through a feedback mechanism in the skin EP device, which prevents heating of a tissue, and reduces tissue damage, pain and contributes to the overall success of the skin electroporation technology provided. The feedback mechanism is a functionality of certain software or hardware (or firmware) described herein, and preferably is a functionality of the hardware. In embodiments where the feedback mechanism is a part of the software, such software is in digital communication with the controller that controls the operation of the skin EP device and performs the acts of receiving impedance from the neutral skin electrode and comparing the impedance to the preset current and adjusting the pulse of energy delivered to the desired tissue to maintain a constant current in the tissue.

In one embodiment of the present invention, provided are electroporation devices configured to deliver to a desired tissue of a mammal a pulse of energy producing a constant current similar to a preset current input by a user. The electroporation device comprises an electroporation component and a skin electrode assembly. The electroporation component can include and incorporate one or more of the various elements of the skin EP devices, including: controller, current waveform generator, impedance tester, waveform logger, input element, status reporting element, communication port, memory component, power source, and power switch. In some embodiments, the electroporation component can function as one element of the skin EP devices, and the other elements are separate elements (or components) in communication with the electroporation component. In some embodiments, the electroporation component can function as more than one element of the skin EP devices, which can be in communication with still other elements of the skin EP devices separate from the electroporation component. The present invention is not limited by the elements of the skin EP devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The skin electrode assembly includes an electrode array having a plurality of skin electrodes in a spatial arrangement, wherein the skin electrode assembly receives the pulse of energy from the electroporation component and delivers same to the desired tissue through the skin electrodes. At least one of the plurality of skin electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current. In some embodiments, the desired tissue is skin tissue, and preferably subcutaneous tissue or intradermic tissue.

Figure 1:
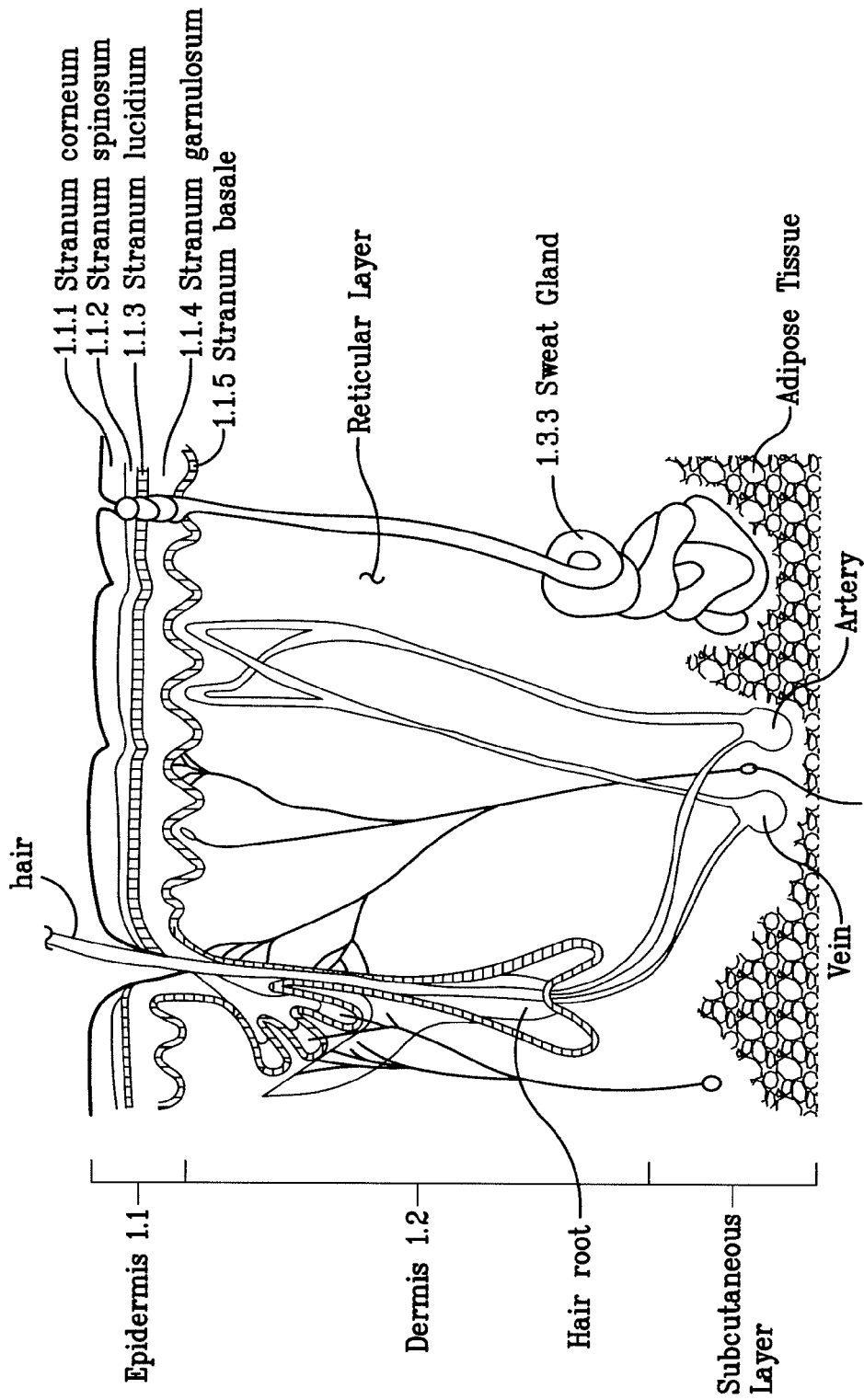
FIG. 1 shows a diagram of the structure of the skin. The most superficial region is the epidermis (1.1), which in turn can be divided into 5 sub-layers: stratum corneum (1.1.1), stratum spinosum (1.1.2), stratum lucidium (1.1.3), stratum granulosum (1.1.4), and stratum basale (1.1.5). The dermis (1.2) is situated just under the epidermis, and it is a very well vascularized region; also the hair roots and sweat glands are located in this layer. The subcutaneous layer is situated just underneath the dermis.
Figure 2A:
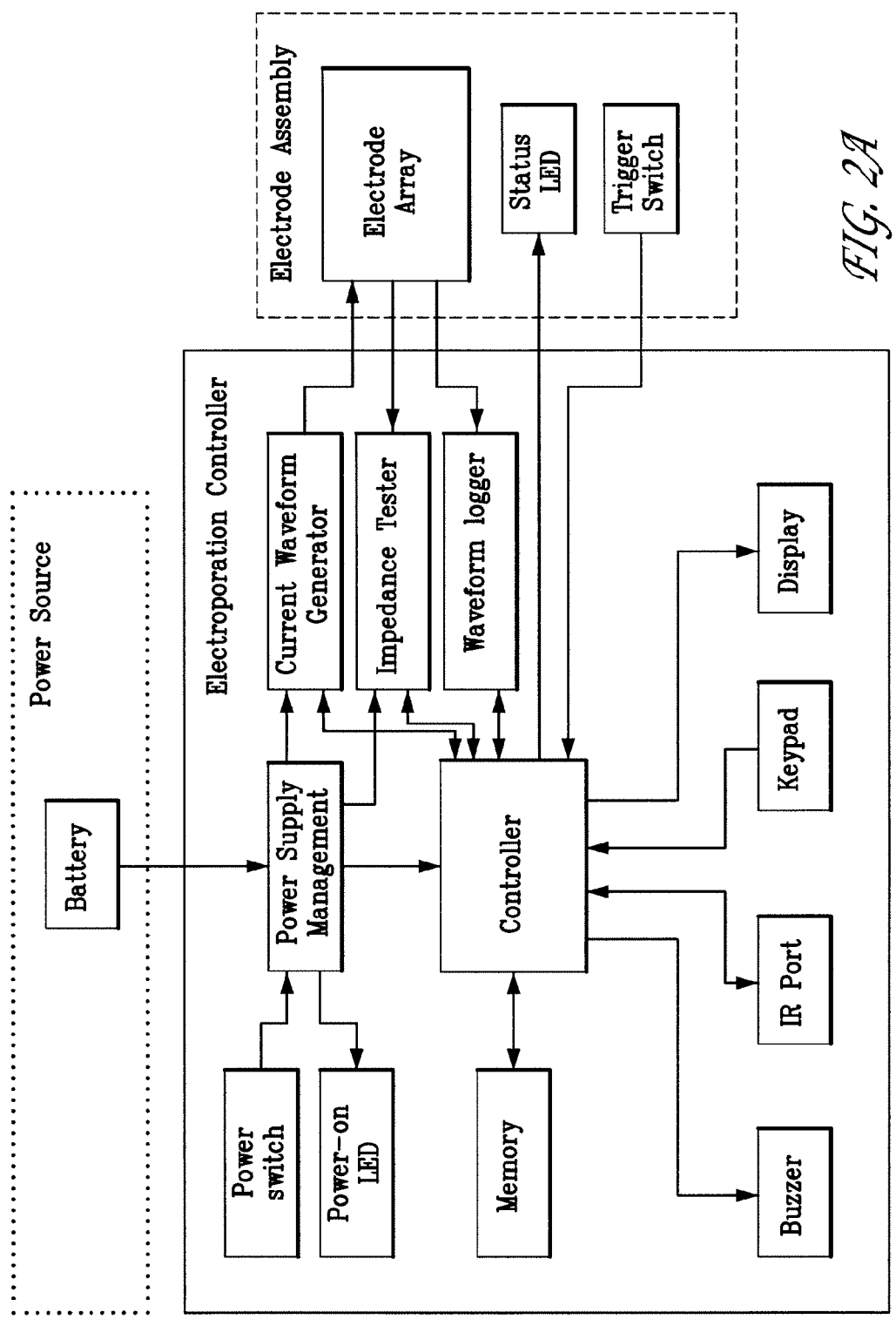
FIG. 2A shows a system diagram of a preferred embodiment of the EP devices described herein.
Figure 2B:
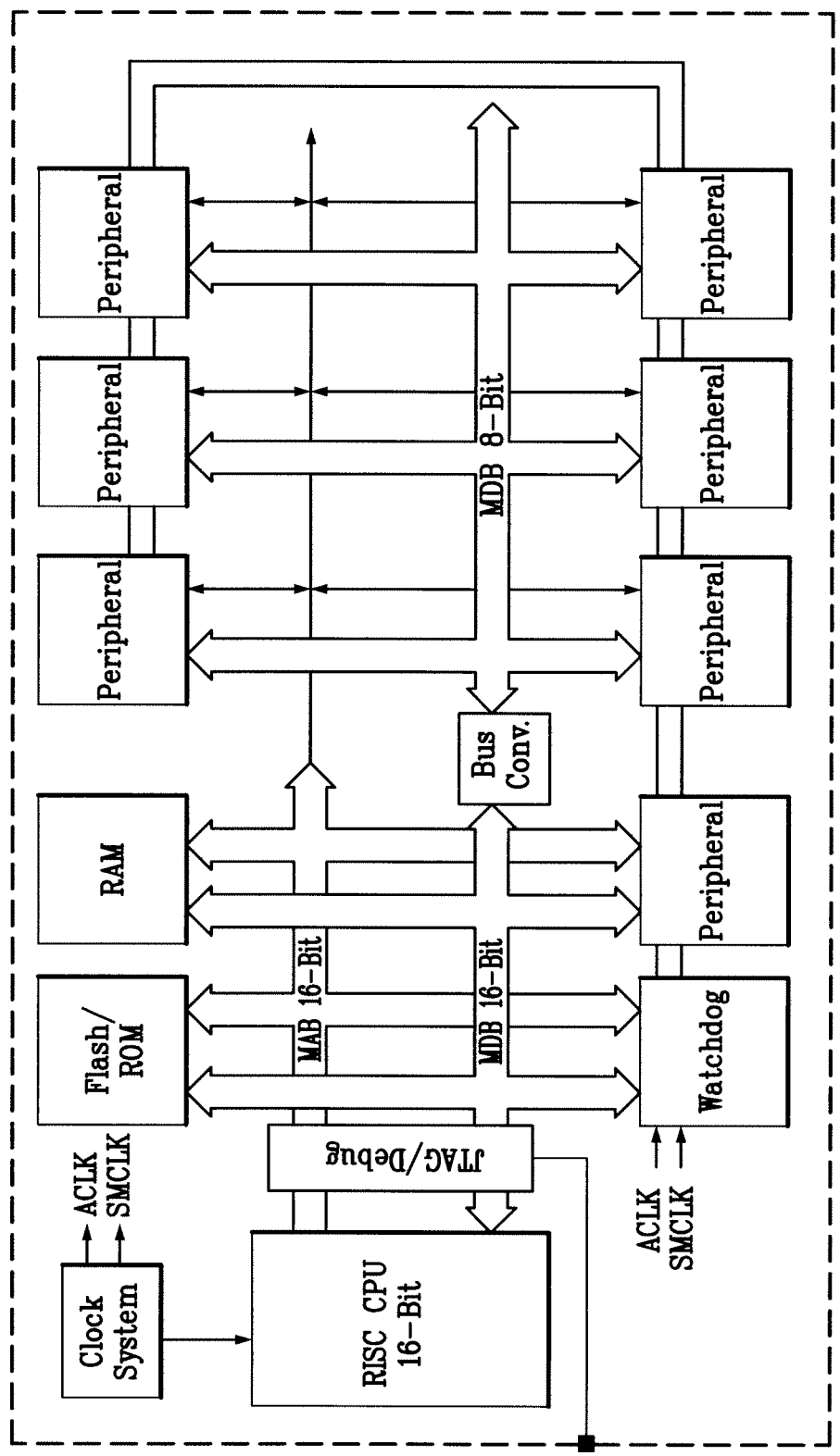
FIG. 2B shows an example of a controller with may be a part of the EP devices described herein.
Figure 7:
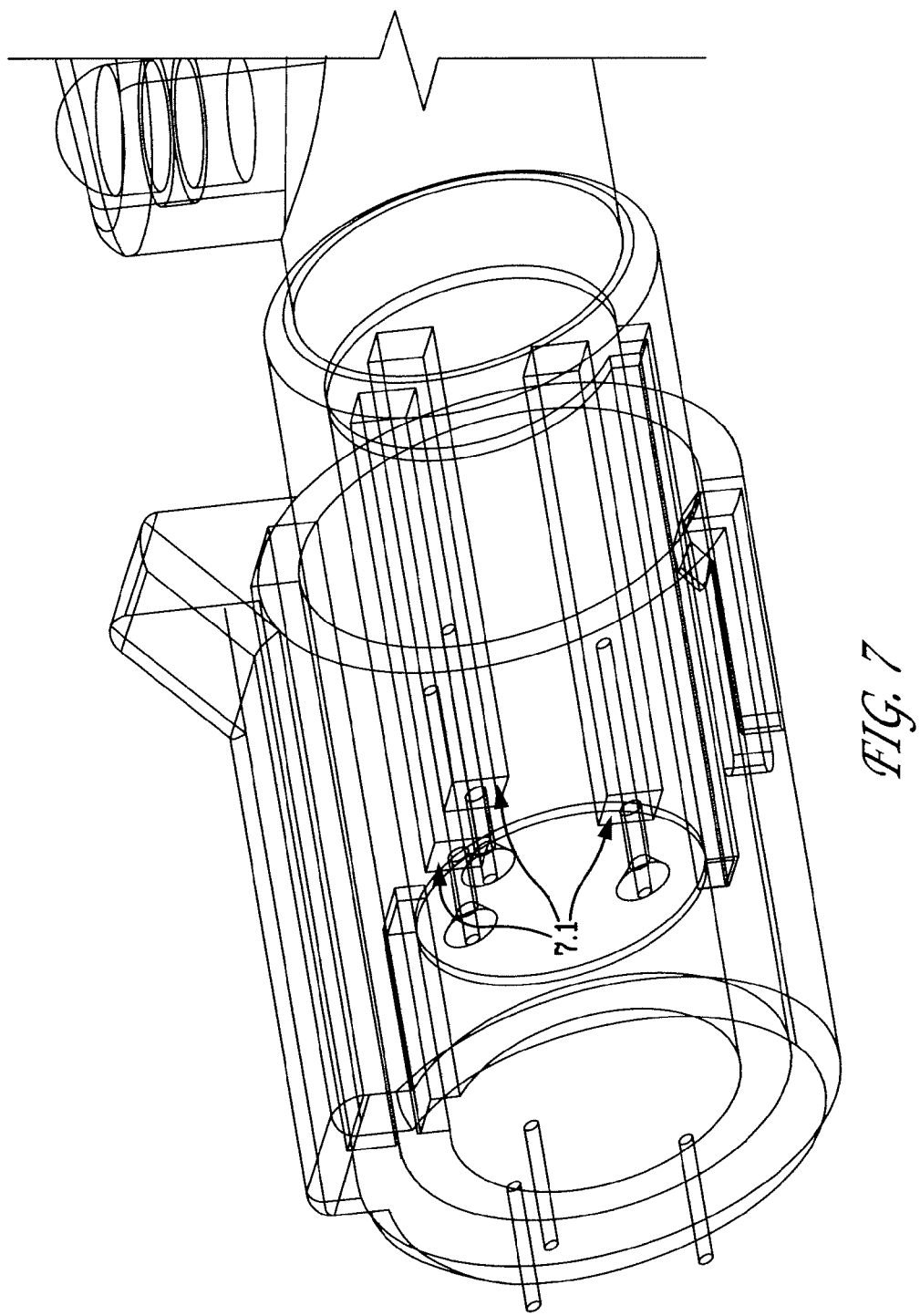
FIG. 7 shows the skin electrode array mounted on the handle: ("7.1") side view schematic of individual sockets for receiving and making electrical connection between the individual needle-electrodes in skin electrode array and skin electrode handle.
Figure 8:
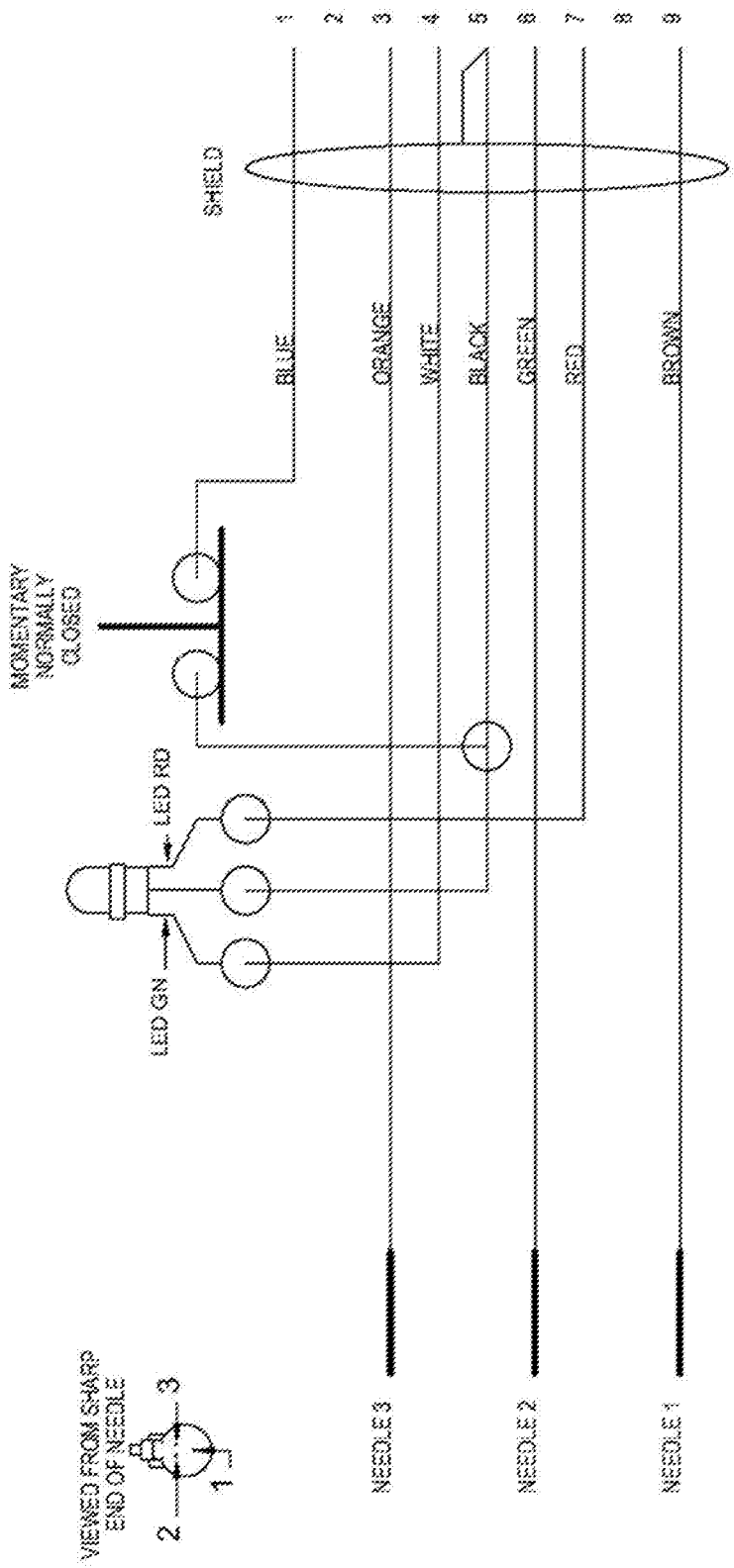
FIG. 8 shows electrical wiring diagram for array and handle assembly.

FIG. 2A shows a system diagram of one preferred embodiment of the EP devices provided herein. Major functional elements of the EP devices are shown in the diagram, but are for illustrative purposes only as not all functional elements are necessary for all embodiments. Each element is described in terms of the hardware functionality of each element. The sequences of events that are enabled by the hardware can be controlled by software, as described herein. The central element of the device is the controller in this example. One example of a controller can be seen in the schematic shown in FIG. 2B, which is a microcontroller, which in some embodiments is a Texas Instruments msp430F149 or Motorola 68HC908AZ60A. Other alternative controllers are known to those skilled in the art of electrical engineering and can readily replace the illustrative examples, above.

In some embodiments, the skin electrodes are needle electrodes, conductive rods, or conductive film areas, and preferably needle electrodes. Preferably, the needle electrodes are capable of contacting an intradermic or a subcutaneous tissue without substantially penetrating a muscle tissue. In some embodiments the skin electrodes can be mounted on a base, which can of plastic material, forming a replaceable, or exchangeable, skin electrode disk having an array of skin electrodes (or skin array or skin needle array) which can be used in association with the skin EP devices described herein. In some embodiments, the skin electrodes can be from about 1 mm to 20 mm; 1 mm to 12 mm; 2 mm to 10 mm; 2 mm to 7 mm in length; or about 5 mm in length. In some embodiments the skin electrode can be 22 to 28 gauge; 23 to 27 gauge; 24 to 27 gauge, or about 26 gauge. Preferably, the skin electrode is approximately 5 mm in length and 26 gauge. In some embodiments the skin electrode is the only part of the skin EP device that actually touches the skin of the patient (to prevent cross-contamination). A vaccine formulation can be delivered to the selected area, the area surrounded by the skin array, and the skin electrodes inserted into the skin. The skin array preferably creates a uniform pressure around the skin electrodes inserted into the skin, and thereby helps to generate a uniform electric field during the EP process in the target area.

In some embodiments, the skin electrode assembly further comprises: an activator switch, and a status indicator for reporting activation of the skin electrode assembly. In some embodiments, the electrode array comprises at least three skin electrodes, and preferably the three skin electrodes have a spatial arrangement that is a triangle. Preferably, the triangle is an isosceles triangle. In some embodiments, the electrode array comprises three skin electrodes spatially arranged as an isosceles triangle having sides of 5 mm in length and a base of 3 mm in length. In some embodiments, the electrode array is disposable and removably connected to the skin electrode assembly. Preferably, the disposable electrode array is a skin electrode disk, and more preferably, the skin electrode disk is sterilizable.

In some embodiments, the plurality of skin electrodes can deliver the pulse of energy in a decentralized pattern. In some embodiments, the plurality of skin electrodes can deliver the pulse of energy in the decentralized pattern through the control of the skin electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active skin electrodes with one neutral electrode that measures impedance, and wherein a subsequent pulse of the plurality of pulses is delivered by a different one of at least two active skin electrodes with one neutral skin electrode that measures impedance.

In some embodiments, the feedback mechanism is performed by either hardware or software. Preferably, the feedback mechanism is performed by an analog closed-loop circuit. Preferably, this feedback occurs every 50 µs, 20 µs, 10 µs or 1 µs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

In some embodiments, the skin electroporation device also includes a controller that receives the inputs from the user and controls the electroporation component to deliver the pulse of energy according to the inputs. In some embodiments, the controller can receive the inputs from the user and control the electroporation component to deliver the pulse of energy according to the inputs. Preferably, the controller is a single chip microcontroller.

In some embodiments, an element of the skin EP device is the controller, which can be responsible for controlling various peripheral devices connected to it or associated therewith. The controller is responsible for managing the electroporation procedure, which includes operations such as: (1) generating the electroporation firing sequence or constant-current pulse pattern for the electrode assembly by controlling the current waveform generator; (2) performing impedance testing to determine if electroporation should be performed; (3) sensing and processing user commands; (4) providing the user with status information; (5) transmitting electroporation data to an external electronic device via the communications port; and (6) saving and retrieving electroporation data (e.g. voltage and current curves) to and from memory. The controller can operate via software or firmware application, which allows a user to input desired pulse parameters and programmed sequence (including electrode firing sequence) and control the operation of the skin EP device.

In some embodiments, the controller includes or is programmed using software that efficiently processes information from both a user and tissue that is undergoing skin EP and controls electrical energy output to deliver to the tissue a constant-current. Programmed can include any one of a number of pulse parameters that are preselected before electroporation, including preset current, programmed sequence (of electrode firing sequence), pulse duration, pulse number (in train of pulses), allowable error around the preset current. This process of receiving and processing inputs and factoring same in order to decide electrical output can occur within the duration of an electrical pulse, and can occur, preferably, within 1 millisecond (ms), more preferably 100 microseconds (µs), and more preferably within 10 µs, and even more preferably within 1 µs. In some embodiments, this process occurs in real-time or instantaneously.

In an example of operation of the skin EP devices described herein, the controller can deliver pulses of energy according to a programmed sequence by at least setting the desired constant current to that of the preset current. In one embodiment, an analog closed-loop feedback circuit continuously maintains the desired constant current by adjusting the voltage applied across the electrodes as the target tissue resistance changes, preferably skin. The controller can end the pulse when the pulse time length has been met by setting the desired output current to zero. When the sequence of pulses is over, the controller can review the waveform data and alert the user if the current in the desired tissue was outside a window of error around the preset current during the electroporation sequence.

The controller can be a single-chip microcontroller, preferably a processor that has one or more of the following properties: abundant I/O, on-board peripherals, low power consumption, and extensive memory capability. In some embodiments, the controller comprises a Texas Instruments processor msp430F149. Software can direct the steps of the electroporation procedure, and can direct the steps in conjunction with the hardware, and is preferably firmware because it resides permanently within and runs from the single-chip microcontroller. In some embodiments, the software performs an algorithm that includes receiving a device user's input, receiving information from the needle electrodes on resistance in pulse receiving tissue, or current therein, and adjusting electrical output based on received inputs within the duration of each electrical pulse.

In some embodiments, the skin electroporation device also includes a current waveform generator in communication with the electroporation component and in electrical communication with the skin electrode assembly; the current waveform generator generating a current pulse train waveform for delivery through the skin electrode assembly. In some embodiments, the user inputs a programmed sequence to the electroporation component, which communicates the programmed sequence to the current waveform generator; wherein the current waveform generator is capable of generating the current pulse train waveform according to the provided programmed sequence. Preferably, the current waveform generator is a power-transistor analog circuit. The current waveform generator can generate a current pulse train waveform that passes through the electrodes of the electrode array in accordance with the programmed sequence. The pulse train is preferably square in shape and the number of pulses is limited by the software or firmware, and preferably from 1 to 10 pulses, and more preferably from 2 to 5 pulses, and more preferably 2 to 3 pulses. One pulse is applied to each electrode set. In some embodiments, a pulse is from 20 ms to 52 ms in duration and occurs at a rate of 1 Hz. The amplitude of the pulse train is programmable by the operator and ranges from 0.1 Amperes (A or Amp) to 1.5 A in increments of 0.1 A. In one embodiment for the present invention, the pulse amplitude is below 0.4 A, and preferably between 0.1 and 0.2 A (see FIGS. 2 and 3). The amplitude of the pulse train can be adapted as a function of the individual tissue resistance, both between individuals and in targeting different areas of the body, preferably skin tissue, of the same individual. The current waveform generator can comprise a general power-transistor analog circuit, which can function under the direction of the controller.

In some embodiments, the skin electroporation device also includes an impedance tester capable of testing for establishment of an electrical connection between the skin electrodes and the desired tissue. The impedance tester can be used to determine whether the skin EP devices' circuitry has established proper electrical connection to the tissue. This test verifies that the inserted skin electrodes have established a good connection to the handle, and that the skin electrodes also have a good connection to the tissue. EP treatment can be preceded by an impedance test. If any of the impedance measurements fall outside a programmable range of resistance (measured in Ohms, Ω), the impedance test fails and the electroporation sequence is not initiated. See the electroporation functional flow in FIG. 27A, particularly the decision box 27A.10, which can lead to a delay of firing if the impedance is not enabled (in other words, an electrical contact is not made between the electrodes and the desired tissue).

The impedance test is an operator programmable feature, controlled by software or firmware that can be disabled during the operation. The impedance tester may be composed of general operational amplifier analog circuits which function as directed by the controller.

The impedance tester can function as a safety feature in the skin EP device. It can indicate, for example, whether all of the electrodes have penetrated the same tissue and a circuit can be established. Electrodes in contact with air, especially dry air, have an extremely high resistance. If electroporation starts and one or more electrodes have not penetrated the tissue (a real possibility when dealing with skin electrodes and skin EP procedures), the resulting electrode voltages can be thousands of volts, which might have lethal or damaging consequences for the subject and also damage the skin EP device. For this reason, overload voltage protection may be implemented to prevent excessive voltages on the electrodes. In some embodiments, the electroporation device includes a safety feature, the safety feature being a voltage cap that prevents the device from delivering the pulse of energy to the tissue when adjustment to the pulse of energy would yield a voltage above the voltage cap. Regardless of the electrical load (e.g. air, skin or muscle tissue), the over-voltage protection may be engaged (or safety cap may be triggered) if $V_{ij}$ exceeds 200V for a period of no more than 1 ms. $V_{ij}$ is the voltage across electrode i and j where i, j=1 to 5. If the over-voltage protection engages (or safety cap is triggered), $V_{ij}$ goes to approximately 0 V until the next electroporation pulse is fired. While the skin EP device is in the off state, the voltage across any electrode pair preferably does not exceed 10V.

In some embodiments, the skin electroporation device also includes a waveform logger in communication with the electroporation component. Preferably, the waveform logger is capable of recording electroporation voltage and current waveforms continuously during the delivery of the pulse of energy. More preferably, the waveform logger is capable of recording electroporation voltage and current waveforms at a rate of 2000 samples per second. The waveform logger, by sampling and monitoring the parameters of the electroporation procedure, enables the user to receive and process possible problems and adjust the settings in the event that an electroporation procedure fails or does not achieve desirable results. An exemplary sample rate is 2000 samples per second, about 104 samples for each of the 2-3 current pulses of 52 milliseconds (ms). An exemplary total sample period is 2208 ms with sampling starting approximately 50 ms before the first pulse is fired and stopping about 50 ms following the last pulse in a 2-pulse pattern. The voltage and current waveforms may be quantified into a 12-bit digital representation with +1 least significant bit ("LSB") linearity. The current waveform resolution should preferably be at least 10 milliamperes (mA) and the voltage waveform resolution should preferably be at least 1.0 V. The waveform logger may be composed of general operational amplifier analog circuits and an analog to digital ("A/D") converter suitable for use with the controller. An example of the waveform logger characteristic for skin delivery of DNA formulations is tabulated in FIG. 2C (please refer to "2.5").

In some embodiments, the skin electroporation device also includes an input device in direct communication with the user and the electroporation component, the input device capable of receiving input commands and communicating the input commands to the electroporation component. Preferably, the input device is a numeric keypad or a touch screen. In one example, the skin EP devices operating parameters may be entered by an operator via a numeric keypad (such as, Grayhill 88AB2). In a preferred embodiment, the numbers input into the keypad are displayed on a liquid crystal display ("LCD"). Typical parameters that can be programmed are the electroporation pulse current, impedance test enable/disable, and electroporation firing delay. The features related to the keypad can also be directed by the controller. An example of the information that is useful for electroporation using one of the described skin EP devices includes: subject identification number, number of pulse in sequence, pre-wait time (seconds, s, sec), pulse width (ms), pulse current (Amp), and the switching pattern for the needle electrodes of the skin electrode array (subject identification number, as well as all the electroporation conditions are automatically recorded and available for analysis). One example of the information that is useful for electroporation using one of the described skin EP devices is given in FIG. 2C (note that subject identification number, as well as all the electroporation conditions are automatically recorded and available for analysis).

In some embodiments, the skin EP devices can further include a status reporting element for displaying or otherwise notifying the operator as to the status of the system. In some embodiments, the skin electroporation device also includes a status reporting element in communication with the electroporation component. Preferably, the status reporting element is an information display panel, an audible notification, a light-emitting diode, or a combination thereof. The status reporting element can report confirmation of the generation of the pulse of energy and delivery of the constant current. These status reporting elements may include an information display panel, such as a liquid crystal display ("LCD") (such as, Lumex LCM-S02004DSF). The LCD is preferably of the character display type and is preferably capable of displaying 4 lines of 20 characters each. The LCD is also preferably equipped with a back-light that can be switched on and off by means of a toggle switch. Status information may also be provided by audible notification, such as a buzzer (such as, CUI CEP-2202AS) sounding at various pitches. Each pitch preferably has a different meaning, as controlled by the software or firmware. For example, the volume of the buzzer may have 3 programmable settings and range roughly from 60 to 80 dB at a distance of 1 meter from the buzzer. The sound pressure level range is only given as reference. The sound level is deemed acceptable if it is audible in a noisy environment (e.g. a farm, or a military compound) if set to its highest level and it is not too loud in a quite environment (e.g. an office) if set to its lowest level. In addition, the SKIN EP DEVICE may be equipped with a light emitting diode ("LED") (such as, Lumex SSI-LXR16121D, or any panel-mount red LED) to designate whether the unit is turned on or off.

Preferably, the status reporting elements include a visual confirmation of the successful generation of an electric field on the LCD following the completion of the electric pulse sequence. In one embodiment, following each electroporation process (or electroporation sequence), the LCD will exhibit a list of three or five numerals, either "1" or "0", one for each of the pulses of the electroporation sequence. A "0" indicates that the pulse was normal and a "1" indicates that the pulse was abnormal. More specifically, each pulse must achieve at least 90% of the set current to be described as normal or a "0" will be displayed in the LCD. If a certain pulse achieved less than 90% of the set current, the pulse is abnormal and a "1" will be displayed. Furthermore, the lowest and average current of the abnormal pulses are displayed. For example, for a five pulse electroporation sequence set at current of 0.5 Amps, if pulses 3 and 5 achieve only 0.4 Amps and 0.3 Amps, respectively, "0 0 1 0 1" will be displayed as well as "Low: 60% Average 80%".

In some embodiments, the skin electroporation device also includes a communication port in communication with the electroporation component. In some embodiments, the communications port that can be used to upload electroporation waveform data to an external electronic device, such as a handheld personal computer (e.g., "Pocket PC"), personal digital assistant ("PDA") or personal computer ("PC"), for viewing purposes. Preferably, the communications port is an optical serial communications port, such as an infrared ("IR") port (such as, Transceiver: ACTiSYS ACT-IR220LN115, or Zilog ZHX1201; Encoder: Microchip MCP2120, or TI TIR1000).

In some embodiments, the skin electroporation device also includes a memory component in communication with the electroporation component. The memory component can store electroporation waveform data and operating parameters. Preferably, the memory component (such as, Atmel AT45 DB321B or AT45 DB321C-TU) is nonvolatile, meaning it retains its data even if the skin EP device is off. To conserve memory, electroporation waveform data only can be saved to memory during the active periods of the electroporation pulse train. During the inactive periods, sampled data only can be stored to memory if either one of the waveforms exceeds a specified threshold. For example, these thresholds may be a voltage threshold of 2 V and a current threshold of 10 mA. Data stored to memory during the inactive periods of the current pulse train may be time stamped so that the time index of the data is known once the waveforms are reconstructed. Provision may be made for the storage of up to 40 samples (20 ms) of data that occur during the inactive periods of the pulse train. Storage can be limited to 20 ms because the software can specify that the remainder of the electroporation sequence will be aborted if anyone of the thresholds is exceeded for a cumulative period of more than 20 ms. An electroporation waveform data set requires about 2 kB of memory when the above compression technique is implemented. The memory component of the skin EP devices preferably contains sufficient memory to save at least 8000 pulses (each pulse is stored separately).

In some embodiments, the skin electroporation device also includes a power source in communication with the electroporation component. Preferably, the power source is a battery, and more preferably, a battery such as a lithium ion, nickel metal hydride, lead acid, or nickel cadmium battery. In some embodiments, the power source is preferably a battery (such as, two 6V Panasonic LC-R064R5P 4.5 Ah, two 6V genesis NP7-6 6V 7.0 Ah) and is responsible for providing power to each of the skin EP devices' circuits. These circuits include a low voltage/low power capacity power supply for the controller and its peripherals, a low voltage and low power capacity power supply for the impedance tester, and a high power capacity power supply for the current waveform generator. The power switch (such as, E-Switch R5CBLKBLKEF0, or any DPDT 10A panel-mount rocker switch) controls power to the skin EP devices and can be either on or off. In the off position, all electrical connections to the electrode assembly are electrically neutral within 5 seconds after power is turned off.

In one aspect of the present invention, provided are electroporation handle assemblies (or "handle assembly") configured to deliver a pulse of energy to a desired tissue of a mammal to produce a constant current in the desired tissue similar to a preset current input by a user. The handle assembly comprising a skin electrode array having a plurality of skin electrodes in a spatial arrangement, wherein at least one of the skin electrodes is neutral during delivery of the pulse of energy and measures impedance in the desired tissue; a controller in communication with the skin electrode array, the controller controlling delivery of the pulse of energy through the skin electrodes; and a means for performing a feedback mechanism, wherein the feedback mechanism is performed by software or hardware, which receives the measured impedance from the neutral skin electrode and adjusts the pulse of energy delivered, if needed, to maintain the constant current.

In some embodiments, the skin EP devices also include a skin electrode handle assembly. Preferably, the handle assembly includes three elements: a skin electrode array (preferably, a skin needle electrode array), a status indicator for reporting the status of the skin EP device, and an activator switch. The array can include any number of needle electrodes in one or more different spatial arrangements, and preferably include odd number of electrodes and also preferably a lower number of electrodes, preferably 7 electrodes or less. In a preferred embodiment, the needle skin electrode array is circular and comprises three needle skin electrodes placed in an isosceles formation, with the large sides of 5 mm and the small base of 3 mm; this placement is believed to be important for the pulse pattern and electric field generation, and consequently quality of the skin EP. The status of the skin EP device is preferably indicated on the handle assembly through the use of status indicators, such as one or more LED's, which can be in varying colors and programmed to flash intermittently to signify various steps of the electrode firing sequence. The handle assembly activator switch is preferably used to initiate various steps of the electrode firing sequence ("6.1.1").

In some embodiments, the handle assembly is wireless and can be operated remotely from the electroporation component (or controller). The wireless handle assembly can receive information from the electroporation component (or controller), including the programmed sequence and pulse parameters, and deliver a pulse of energy to the desired tissue and maintain the constant current in same tissue. The wireless handle assembly can include an internal battery or a capacitor that holds an electrical charge for its operation. Preferably, the wireless handle assembly will include the feedback mechanism, preferably the analog closed-loop circuit. The wireless handle assembly can dock with the electroporation component and exchange information and provide one or more of the functionalities of the skin EP devices described herein.

In some embodiments, the electrode array is disposable and removably connected to the skin electrode assembly. Preferably, the disposable electrode array is a skin electrode disk, and more preferably, the skin electrode disk is sterilizable.

In one embodiment of the present invention, the skin EP devices include a replaceable skin electrode disk which can be removably mounted in the handle assembly. In a preferred embodiment, the replaceable skin electrode disk is mounted on the handle assembly of the skin EP device. FIGS. 6.1 and 6.2 depict the side view of the electrode array ("6.2.3" and "6.2.5"). In FIGS. 6.1 and 6.2, the electrode disk has a plurality of needle skin electrodes mounted on a support structure in a spatial arrangement for penetrating the selected tissue, in particular skin. In a preferred embodiment, the spatial arrangement is a circular skin array. Individual skin electrodes in the needle array on the handle side of the skin electrode disk are blunt-ended and deburred for insertion into the complementary electrical contact fittings in the handle. The handle preferably houses an electrical connector from the needle skin electrodes to the pulse generator or skin EP device.

In a preferred embodiment, the needle skin electrodes in the skin EP device skin electrode assembly as well as in the replaceable skin electrode disk are in a circular array. In a further preferred embodiment, the plurality of needle skin electrodes consists of three needle skin electrodes. In an additional preferred embodiment, the center of the three needle skin electrodes fall in a circular array in the shape of a formation inscribed by 2 sides of 5 mm and a small base of 3 mm.

Figure 9:
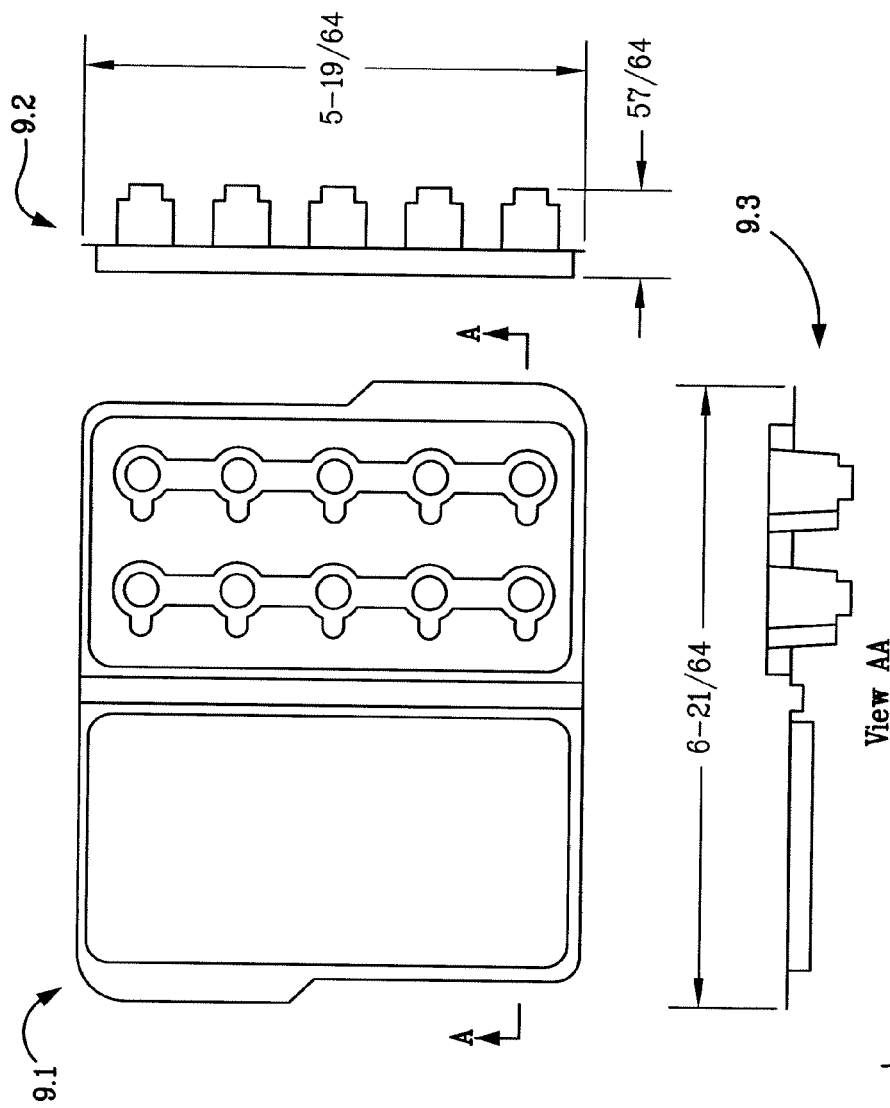
FIG. 9 shows the schematic representation of the multi skin electrode array clamshell folding packaging container that allows for sterile loading of the handle between treatment subjects: ("9.1") lid; ("9.2") base, including individual wells custom-designed to house arrays; ("9.3") side-view of wells.

In a preferred embodiment, the needle skin electrodes are stored sterile in a specific packaging system (FIG. 9) that allows for rapid change of the skin electrode array between treated subjects, while maintaining each skin electrode array sterile.

In some embodiments, a programmed sequence is provided for the operation of the skin EP devices, which controls whether each electrode of the skin needle array can function as a positive, negative, or neutral electrode. For example, as shown in FIG. 2C, in a programmed sequence each electrode can function as a positive, negative or off position. The entire sequence in FIG. 2C is depicted in which electrodes 1 through 3 become the positive electrode successively, with two negatively charge electrodes at opposite vertices of the skin array ("2.4"—second column), or one electrode off, one positive and one negative ("2.4"—forth column).

In some embodiments, the electroporation component comprises a controller; a waveform generator in electronic communication with the controller; a waveform logger in electronic communication with the controller; and a battery electrically connected to the waveform generator. The controller can receive an input from the user, instruct the waveform generator to deliver the pulse of energy to the desired tissue according to the input, and communicate data to the waveform logger according to the pulse of energy delivered; and wherein the battery sends an electrical charge to the waveform generator, the battery being a lithium ion, nickel metal hydride, lead acid, or nickel cadmium battery. Preferably, the device is portable. The portable device an be operated via a battery pack, and suitable for mass vaccination for therapeutic or vaccination purposes.

In some embodiments of the present invention, provided are methods of using the skin electroporation devices described herein to deliver the pulse of energy to the desired skin tissue to produce the constant current similar to a preset current input by a user. The methods include: inserting a plurality of needle skin electrodes into skin tissue without substantially penetrating a muscle tissue; and applying the pulse of energy to the plurality of needle skin electrodes to deliver a current equal to the preset current in the skin tissue; and measuring impedance of the skin tissue with a neutral one of the plurality of needle skin electrodes and using a feedback mechanism in the electroporation device to adjust the pulse of energy applied in response to the measured impedance to maintain the current delivered to the skin tissue constant. In one example of a preferred embodiment, the methods of using the skin EP devices include progressing through an electroporation functional sequence such as that depicted in the flow chart provided in FIGS. 27A and 27B. In particular, 27B.10 in FIG. 27B shows a blow-up of the "produce current pulse" step and depicts the feedback mechanism, which preferably is performed by an analog closed-loop circuit and operates in real-time (or instantaneously).

In some embodiments, the methods further include measuring impedance prior to applying the pulse of energy to determine whether electrical contact is made between the desired skin tissue and needle skin electrodes. In some embodiments, the methods of the invention are used to place at least one DNA vaccine in contact with said intradermic or subcutaneous tissue.

In some embodiments, the methods of the present invention include recording data compiled by the electroporation device from the delivery of the pulse of energy to the desired skin tissue.

In some embodiments of the present invention, provided are methods comprising the steps of: providing an skin electrode assembly having a plurality of needle skin electrodes, the skin electrode assembly in electrical communication with a current waveform generator; contacting skin tissue of a mammal with the plurality of needle skin electrodes without substantially penetrating a muscle tissue of the mammal; and applying an electrical pulse of energy from the current waveform generator to the plurality of needle skin electrodes for a time and under conditions effective to expose the contacted skin tissue to a substantially constant current.

In some embodiments, the applying the electrical pulse of energy step comprises: measuring impedance in the contacted skin tissue with a neutral one of the plurality of needle skin electrodes; and communicating the measured impedance to a feedback mechanism in electrical communication with the current waveform generator, wherein the feedback mechanism adjusts the pulse of energy delivered from the current waveform generator in response to the measured impedance to maintain the substantially constant current. In some embodiments, the feedback mechanism is performed by an analog closed-loop circuit that is part of the electroporation device, and the measuring and communicating steps are performed instantaneously throughout the duration of the pulse of energy.

One aspect of the present invention pertains to the skin EP devices, which enable in vivo electroporation of biomolecules, for example DNA plasmids, into desired skin tissue or skin cells. In some embodiments the skin EP devices provide a constant-current electric field to a skin tissue of interest through a skin electrode needle array and facilitate the introduction of a biomolecule into cells of selected skin tissue, preferably subcutaneous (SQ) and/or intradermal (ID) tissue. The skin EP devices produce a current pulse train waveform that passes through the electrodes of the skin electrode needle array in accordance with a programmed sequence and can be monitored and recorded during the procedure. The needle electrodes are capable of contacting skin tissue, such as SQ or ID tissue, without substantially penetrating a muscle tissue. The skin EP devices produce a current pulse train waveform that passes through the skin electrodes of the skin array in accordance with a programmed sequence and can be monitored and recorded during the procedure (see FIG. 2C). The needle skin electrodes are capable of contacting intradermic or subcutaneous tissue without substantially penetrating a muscle tissue.

U.S. Pat. No. 7,245,963 and U.S. Patent Pub. 2005/0052630 discloses system diagrams of certain electroporation components that can be used in accordance with the present invention, where they are adaptable into or as part of the skin EP devices. Each element is described therein in terms of the hardware functionality of such element. The entire content of each of these publications is hereby incorporated by reference in their entirety. The sequences of events that are enabled by the hardware are controlled by software or firmware or combination of both, as described herein.

In some embodiments, the electroporation component of the skin EP device comprises an electrode-connect relay matrix, which can facilitate the programmed sequence and operate the firing of the electrodes in the skin electrode assembly. The relay matrix can control each of the electrodes, preferably needle electrodes, so that each electrode is in one of five states: off, positive low voltage, impedance-measuring input, positive high voltage, and negative (regulating) high voltage. In one embodiment, the relay matrix includes 11 double pole, double throw (DPDT) relays that create a switch matrix. 10 of those relays are driven using a set of shift registers connected to the serial peripheral interface (SPI) port as an SPI-to-parallel port. The SPI slave in, master out (SIMO) is connected to the Data-In pin of both 74VHC595 (or approved equivalent) shift registers. The 74VHC595 has 2 clock inputs. The universal serial synchronous/asynchronous communication interface claock (UCLK) signal is connected to the shift register clock input (SCK) pins of the registers used to shift data into the register. Separate general purpose input/output (GPIO) pins go to the storage register clock (RCK) clock inputs used to clock data from the shift register, in parallel, into the output register. The result is the same serial data is shifted into both shift registers, but then the data is only clocked into the output register of the one to change.

To drive the actual relay coils, the outputs of the SPI port circuit feed 2 ULN2003A (or approved equivalent) 8-channel relay coil drivers. This chip is basically an array of open-collector bipolar junction transistors (BJTs). Each channel output also has an internal kickback diode across it—eliminating the need for external diodes. The positive side of the relay coils is tied to 15 volts, while the negative side of the coils is pulled to ground through the ULN2003A parts.

There are 3 sets of relays in the contact matrix. An example of a relay contact matrix can be seen in FIG. 26. The first set is actually 1 DPDT relay. One set of contacts switches the positive rail from the low-voltage, impedance-measuring voltage, to the output of the 200V supply. The other set of contacts in the same relay switch the negative rail between the impedance-measuring circuit and the pulse-current regulating circuit. Thus, the position of this relay sets both the positive and negative rails to either do a current pulse, or to make an impedance measurement. The next set of relays is the 5-relay set of polarity relays. These relays, one for each electrode, switch the polarity for that electrode to either the positive or negative rail. The last set of relays is just an inline set of contacts to allow each contact to be isolated as neither positive nor negative. To improve the life of the relay contacts, the matrix is meant only to connect the load to the appropriate electrodes in the desired way. The pulse or impedance circuits then pass voltage or current to the load. The voltage or current is then removed before any contacts are opened. Since the contacts do not actually switch when current is being applied, the life of the contacts can be greatly extended.

One example of a current pulse produced by the skin EP devices is shown in FIGS. 3.1 and 3.2. FIGS. 3.1 and 3.2 shows the waveform of each current pulse. The waveform parameters are:

Period ($t_p$): 1000 ms±250 µs.
Rise time ($t_r$): 20 µs maximum.
Settling time ($t_s$): 20 µs maximum.
Pulse width ($t_w$): 52 ms±100 µs.
Fall time ($t_f$): 20 µs maximum.
Nominal current ($I_n$): $I_n \in$(0.1 A, 0.2 A, 0.3 A ... 1.5 A)±10% of $I_n$ during $t_h$, and with $R_l \leq 100\Omega$. $R_l$ is the load resistance between anyone of the 3 electrode sets shown in FIGS. 3.3 and 3.4. Only the current waveform is specified in FIGS. 3.1 and 3.2. The shape of the voltage waveform depends on the impedance seen by the electrodes while the current pulse is firing (during $t_h$). The voltage waveform is not specified during $t_h$ since the impedance is unknown during this period. The voltage across any electrode set during $t_l$ is 0V.

Although not wanting to be bound by theory, it is believed that electroporation makes use of the same structures and forces a high ionic flux through these structures and opening or enlarging the conduits. Metallic or dielectric electrodes are placed in contact with tissues and predetermined voltages, proportional to the distance between the electrodes are imposed on them. The protocols used for electroporation are defined in terms of the resulting field intensities, according to the formula E=V/d, where ("E") is the field, ("V") is the imposed voltage and ("d") is the distance between the electrodes.

The electric field intensity E has been an important value when formulating electroporation protocols for the delivery of a drug or biomolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful EP, not electric field per se. The activation of the skin EP device's current waveform generator will distribute a constant-current electrical pulse to the plurality of needle skin electrodes such that a decentralized EP event occurs in an area where no congruent EP overlap points develop. The permeability of the cells in the area of decentralized EP increases and the biomolecule are delivered into the cell of the subject without overheating and damaging the cell or tissue.

One aspect of the present invention pertains to skin EP devices for introducing biomolecules into one or more cells of an animal, in particular skin, for ID or SQ vaccination purposes. Preferably, the skin EP devices introduce the biomolecules to skin tissue, such as SQ or ID tissue, by delivering and maintaining a constant current in same tissue throughout the duration of the electrical pulse delivered. In some embodiments, the handle of the skin electrode handle assembly is non-conductive and designed to provide a user an easy means for implanting the needle skin electrode assembly into a selected tissue, in particular skin. The utilization of disposable needle skin electrode disks with snap-on mounts on the handle allows a user to quickly attach and detach the needle skin electrode disks, and allowing for rapid (and sterile) change between treated subjects. The power source of the skin EP devices can utilize battery packs for use in the field where access and use of an electrical outlet or other power source is dangerous or inconvenient, as for instance in a mass vaccination during a bioterrorism attack.

Biomolecules for delivery into cells of skin tissue, such as SQ and ID tissue, include DNA plasmids, DNA vaccines (the DNA vaccines and DNA plasmids not being mutually exclusive), genes, therapeutic drugs, or other agents, whether complementary or enhancing agents. Preferably the biomolecules are DNA plasmids that can be expressed in the cells of the targeted skin tissue, and the biomolecules for skin EP delivery can include more than one biomolecule.

The DNA plasmids used with the present invention can be those useful for gene therapy, i.e., the transfer of selected genes into a host for purposes of preventing, ameliorating, or curing an injury or disease state. The DNA plasmids can express the gene of interest in the mammal using the skin EP devices to ameliorate symptoms of a disease, to reduce the pathogenesis of the disease, to eliminate the root cause of the disease, or to prevent the occurrence of the disease. The encoding gene in the DNA plasmid can be a heterologous gene obtained from an exogenous source. Gene therapy can be provided for genetically caused diseases, such as cystic fibrosis or muscular dystrophy. Gene therapy can also be applied for the treatment of tumors. Preferably, the genes of the DNA plasmids encode a growth hormone releasing hormone or insulin growth factor-I, whether synthetic or natural forms or full-length or functional fragments thereof.

In some embodiments, the DNA plasmids used with the present invention can be introduced to cells of the mammal for vaccination purposes, or inoculation against infectious diseases, such as hepatitis, influenza, dengue, Japanese encephalitis, and HIV, for example. In some examples, the DNA plasmids can express polypeptides that are immunogenic fragments of viral protein.

Examples of drugs that can be used as biomolecules for delivery to the skin tissue by skin EP include chemotherapeutic agents having an antitumor or cytotoxic effect, including bleomycin, neocarcinostatin, suramin, doxorubicin, carboplatin, taxol, mitomycin C and cisplatin. Other chemotherapeutic agents are known to those skilled in the art, and can be found in references including The Merck Index. In addition, agents that assist transmembrance delivery ("delivery agents") are also contemplated as biomolecules for delivery and can include: N-alkylmelamide and para-chloro mercury benzoate. In embodiments where the biomolecules are DNA plasmids or DNA vaccines, a further biomolecule for delivery along with, prior to, or subsequent to the DNA plasmids or DNA vaccines, is an additional one or more DNA plasmids or DNA vaccines. In embodiments where the biomolecules are DNA plasmids or DNA vaccines that are intended to express target proteins that elicit an immune response, a further biomolecule for delivery along with, prior to, or subsequent to the DNA plasmids or DNA vaccines, is one or more genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1☐, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

Figure 11:
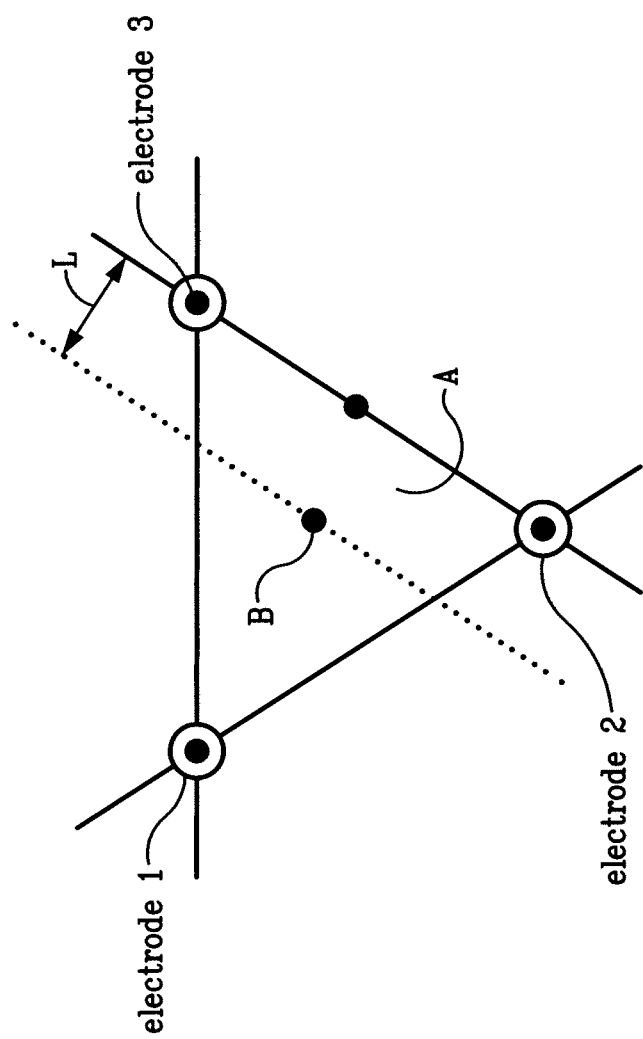
FIG. 11 shows a three-electrode needle array where distance L=k×n, where n represents the number of electrodes and k represents a proportionality constant.

One of ordinary skill understands that numerous changes and modifications of the skin EP devices can be made without departing from the spirit and the scope of the present invention. The skin EP devices can include any number of electrodes, such as a three-electrode array arranged in a different pattern, which can be seen in FIG. 11. The distance L is chosen so that the energy intensity at point B is one third of that at point A. After three pulses, (1 to 2, 2 to 3 and 3 to 1), point B has received a cumulative dose equal to that of point A. As the number of electrodes in the array is increased, the distance L necessary to yield a uniform energy distribution becomes proportionately longer. $L = k \times n$ where n is the number of electrodes, and k is a proportionality constant. Thus, by selecting a greater number of electrodes a greater volume of tissue can be encompassed. The optimal number of skin electrodes chosen may depend on the volume of the material to be transfected and how far it is dispersed between injection and electroporation.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Preferably the DNA formulations for use with the skin EP devices described herein have high DNA concentrations, preferably concentrations that include gram quantities of DNA in small volumes that are optimal for delivery to the skin, preferably small injection volume, ideally 25-200 microliters (μL). In some embodiments, the DNA formulations have high DNA concentrations, such as 1 mg/ml or greater (mg DNA/volume of formulation). More preferably, the DNA formulation has a DNA concentration that provides for gram quantities of DNA in 200 μL of formula, and more preferably gram quantities of DNA in 100 μL of formula.

The DNA plasmids for use with the skin EP devices of the present invention can be formulated or manufactured using a combination of known devices and techniques, but preferably they are manufactured using an optimized plasmid manufacturing technique that is described in a commonly owned, copending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a commonly owned patent, U.S. Pat. No. 7,238,522, which issued on Jul. 3, 2007. The high concentrations of plasmids used with the skin EP devices and delivery techniques described herein allow for administration of plasmids into the ID/SC space in a reasonably low volume and aids in enhancing expression and immunization effects. The commonly owned application and patent, U.S. Ser. No. 60/939,792 and U.S. Pat. No. 7,238,522, respectively, are hereby incorporated in their entirety.

Example 1

Operation of the Electro-Kinetic Device ("Skin EP Device") for Skin Electroporation First, the power to the skin EP device is turned on. The firmware remains in the idle state until input is received from the user. To start an electroporation sequence, a password is entered to obtain an introductory prompt on the LCD. At this point, the handle assembly activator switch is pressed. The user then enters a number, preferably a subject identification number, which is logged with the data of every pulse stored for later download. The number is preferably entered using a numeric keypad. The biomolecule formulation is than administered as an ID or SQ injection in a reasonably small injection volume, ideally 25-200 skin liters and the skin electrode array is inserted into the skin to completely surround the injection area which is easily visualized. The user is then prompted, via a "beep" from the buzzer, to press the activation switch to continue the electroporation sequence. After the activation switch is pressed, the firmware establishes whether or not the impedance tester is enabled. If the impedance tester is enabled, the software immediately performs a series of impedance measurements. The firmware tests the impedance between electrodes with a low DC voltage.

After the electrodes have been inserted into the target tissue, and during the impedance check, the processor checks the conductivity of the tissue at the electrode level. This is done to ensure that electrodes are making electrical contact with the target tissue in the patient. These measurements are performed in a matter of seconds with enough time to achieve accurate readings, often less than 2 seconds. During the impedance testing, a red LED on the handle assembly is lit. If any of the impedance measurements fail, a long error "beep" will sound, the handle LED will stay red, the LCD will display the error, and the firmware will return to the idle state.

If all measurements pass, a short "beep" is emitted, a green LED on the handle assembly is lit, and the display prompts the user to press the activation switch to continue.

The firmware waits for the handle activation switch to be pushed again to continue the sequence. If any key on the keypad is pressed at this time, a long error "beep" will be sounded and the unit will return to the idle state.

The firmware implements the firing sequence as proscribed by the pulsing program selected. During the delivery of each electric pulse or pulse of energy, the EP device continuously adjusts its output based on the resistance measured in the target tissue, for instance skin, to maintain the desired current. In essence, the processor begins the pulse sequence by setting the desired output current level to that of a preset current value entered by a user. A hardware feedback loop (i.e., an analog closed-loop circuit) continuously maintains the desired output current by adjusting the voltage applied across the electrodes as the target tissue resistance changes. During the delivery of the pulse of energy, the processor records the pulse waveform. The processor ends the pulse when the pulse time length has been met by setting the desired output current to zero at such time. When the sequence of pulses is over, the processor reviews the waveform data and alerts the operator if the current was not within the set parameters during the electroporation sequence; thereby, informing the user of whether the electroporation sequence or treatment was faulty or not.

When the EP sequence is completed successfully, the skin EP device returns to the idle state. There is further visual confirmation of the successful generation of an electric field on the LCD following the completion of the electric pulse sequence. Following each sequence, the LCD will exhibit a list of three or five numerals, either "1" or "0", one for each of the pulses of the electroporation sequence. A "0" indicates that the pulse was normal and a "1" indicates that the pulse was abnormal. More specifically, each pulse must achieve at least 90% of the set current to be described as normal or a "0" will be displayed in the LCD. If a certain pulse achieved less than 90% of the set current, the pulse is abnormal and a "1" will be displayed. Furthermore, the lowest and average current of the abnormal pulses are displayed. For example, for a five pulse electroporation sequence set at current of 0.5 Amps, if pulses 3 and 5 achieve only 0.4 Amps and 0.3 Amps, respectively, "0 0 1 0 1" will be displayed as well as "Low: 60% Average 80%". This control mechanism is essential when delivering vaccines for therapeutic or prophylactic applications. Should the vaccine delivery be inadequate, there is a high probability that the antibody or cellular responses needed for treatment or protection will not be achieved, and the subject at risk to developing the disease (Roth et al., 2005).

Example 2

Data Acquisition and Storage

The skin EP device software or firmware enables real time data acquisition and storage in non-volatile memory. FIG. 2C illustrates a first portion of data that may be collected during the electroporation process. The first section of the file header contains the file name ("2.1") and the animal number ("2.2"). The columnar data ("2.3") describes the pulse in sequence, the wait time before pulsing, the pulse width, and the pulse current for each of the three electrodes. FIG. 2.4 illustrates a second portion of data, which identifies the configuration of each electrode during a given pulse sequence. FIG. 2.5 illustrates a formatted version of a third portion of raw data for the same electroporation. The file is downloaded from the skin EP device as a Microsoft Excel CSV file. The data are copied and pasted into a template Microsoft Excel Spreadsheet file. Columns in the spreadsheet represent measured voltage (V) and current (Amps) during the electroporation pulse as well as the calculated tissue resistance (Ohms). Data downloaded after smaller electrodes were used in pigs' skin yielded almost double the skin resistance than after using larger electrodes (700Ω to 2200Ω).

Example 3

Plasmid Design, Delivery Methods, and Experimental Study in Pigs

Plasmid Construction.

pEGFP-N1 (Clontech, Mountain View, Calif.) used in the experiments described herein, encodes a red-shifted variant of wild-type GFP which has been optimized for brighter fluorescence and higher expression in mammalian cells (excitation maximum=488 nm; emission maximum=507 nm.) pEGFP-N1 encodes the GFPmut1 variant which contains the double-amino-acid substitution of Phe-64 to Leu and Ser-65 to Thr. The coding sequence of the EGFP gene contains more than 190 silent base changes which correspond to human codon-usage preferences. Sequences flanking EGFP have been converted to a Kozak consensus translation initiation site to further increase the translation efficiency in eukaryotic cells. SV40 polyadenylation signals downstream of the EGFP gene direct proper processing of the 3' end of the EGFP mRNA. The vector backbone also contains an SV40 origin for replication in mammalian cells expressing the SV40 T-antigen. A neomycin-resistance cassette (neor), consisting of the SV40 early promoter, the neomycin/kanamycin resistance gene of Tn5, and polyadenylation signals from the Herpes simplex thymidine kinase gene, allows stably transfected eukaryotic cells to be selected using G418. A bacterial promoter upstream of this cassette expresses kanamycin resistance in $E.\ coli$. The pEGFP-N1 backbone also provides a pUC19 origin of replication for propagation in $E.\ coli$ and an f1 origin for single-stranded DNA production.

Electroporation Conditions.

Square wave pulses were used in all experiments. Electroporation conditions are stated individually for each experiment. In all cases, constant current was used at 0.1-0.4 Amps, with 2 or 3 pulses, for 20 or 52 milliseconds/pulse, and with one second between pulses. The control skin EP device electroporation device (previously used to deliver biomolecules to the skeletal muscle) contained a circular array (1 cm diameter) of five equally spaced 21-gauge solid stainless steel needle electrodes, mounted on a non-conductive material. The skin electroporation skin electrodes consist of three 26-gauge solid stainless steel needle electrodes in an isosceles triangle formation (two long sides are 5 mm in length, and the short side is 3 mm in length), mounted on non-conductive material.

Intramuscular Injection of Plasmid DNA in Pigs.

Young hybrid pigs of mixed gender, three to six weeks of age, with weights between 15-40 kg, were used in the GFP studies. Animals were housed in individual pens with ad libitum access to food and water. Endotoxin-free plasmid preparations were diluted in sterile water and formulated at 1% weight/weight with HPLC purified low molecular weight poly-L-glutamate (average MW 10,900). On Day 0 of the experiment, the animals were manually restrained and the GFP plasmid solution was directly injected ID and/or SQ as described. A tattoo was placed at 2 cm from the center in the left upper corner of a square where the injection site was placed in the middle of the square, such that each injection site could be easily identified and dissected. All major surface blood vessels were avoided when finding an appropriate injection site.

Skin Collection.

The pigs were exsanguinated and the injection sites identified. A 2.5 cm square area of the skin, subcutaneous tissue and a small amount of underlying muscle were immediately dissected at each injection site. The dissected area was observed in a darkened room using a UV light at 365 nm wavelength.

Photographic Analysis of the Expression Area.

Samples that demonstrated sufficient fluorescence were photographed using a digital camera. Samples with no or very minor fluorescence were not photographed. The fluorescence was scored on a 0 to 5 scale by three observers blinded to the treatment. Zero assigned to those with no fluorescence, 1 to those that were noted as having very minor fluorescence observed but not photographed, and 3 to 5 assessed from the fluorescence photographed. Samples were saved for histological examination.

Example 4

Comparative Study

Data from all tested condition was tabulated. FIG. 10 presents only the conditions were average scores were above or equal to 2, while the maximum possible scoring is 5. As the data shows, the best overall results have been achieved using the skin-specific skin array (first row, FIG. 10). While the next group (second row, FIG. 10) has the same numerical score, it is to be noted that for the skin array ("MA") only 50 μg of plasmid formulated in 50 μL was used, while with the large array ("LA"), a double quantity was used, 100 μg of plasmid formulated in 100 μL. Furthermore, using the optimized conditions for the skin electrode array, the procedure time was substantially reduced: the observed procedure time between injection and EP is 4 seconds (see forth column, FIG. 10) when using the MA, and 80 seconds when using the LA. Many other conditions for plasmid dose, formulation volume, lag time, current amplitude and pulse length were assayed and are presented in FIG. 10. As a general rule, a smaller volume (more concentrated solutions), with an adequate plasmid dose was found to yield better results.

Example 5

Intradermal Delivery Comparisons with Intramuscular Delivery in Pigs

The delivery and expression of concentrated doses of CMV-GHRH and CMV-SLAP plasmid delivered intradermally (ID) or intramuscularly (IM) in pigs were compared. The results demonstrated which delivery method yields the highest expression in pigs using both secreted proteins (SLAP, GHRH) as well as testing SLAP immunogenicity in pigs for the first time.

Animals were housed individually and acclimated for 7 days. On Study Day 0, animals were weighed and bled, then anesthetized. Pigs (n=4/group) were injected with 1 mg of CMV-SELAP and CMV-GHRH+0.1% poly-L-glutamate sodium salt at varying concentrations and current intensities (Table 1). After 4 sec, animals were electroporated using CELLELCTRA™ electroporation device (VGX Pharmaceuticals, Inc., Blue Bell, Pa. 19422) ((5 needles, 52 millisecond pulses, 1 second between pulses, 3 total pulses) with varying current (0.1 to 0.5 Amp). Pigs were allowed to recover from anesthesia and monitored for 24 hours to ensure full recovery. Any animal that did not fully recover within 2 to 3 hours post-treatment were noted. Pigs were weighed and bled on Day 2, 4, 7, 9 and 11. Food and water was available ad libitum for the length of the study. Blood was collected for SLAP, SLAP antibody LLISAs, GHRH, and IGF-1.

TABLE 1

Experimental group summary.

| Group | Plasmid | Dose | Injection Volume | IM or ID | EP current | n= |
|---|---|---|---|---|---|---|
| 1 | CMV-SEAP CMV-GHRH | 10 mg/mL | 100 µL | ID | 0.2 Amp | 4 |
| 2 | CMV-SEAP CMV-GHRH | 2 mg/mL | 500 µL | ID | 0.2 Amp | 4 |
| 3 | CMV-SEAP CMV-GHRH | 10 mg/mL | 100 µL | IM | 0.5 Amp | 4 |
| 4 | CMV-SEAP CMV-GHRH | 2 mg/mL | 500 µL | IM | 0.5 Amp | 4 |
| 5 | CMV-SEAP CMV-GHRH | 2 mg/mL | 500 µL | IM | 0.4 Amp | 4 |
| 6 | CMV-SEAP CMV-GHRH | 2 mg/mL | 500 µL | IM | 0.3 Amp | 4 |
| 7 | CMV-SEAP CMV-GHRH | 10 mg/mL | 100 µL | IM | 0.1 Amp | 4 |

Figure 12:
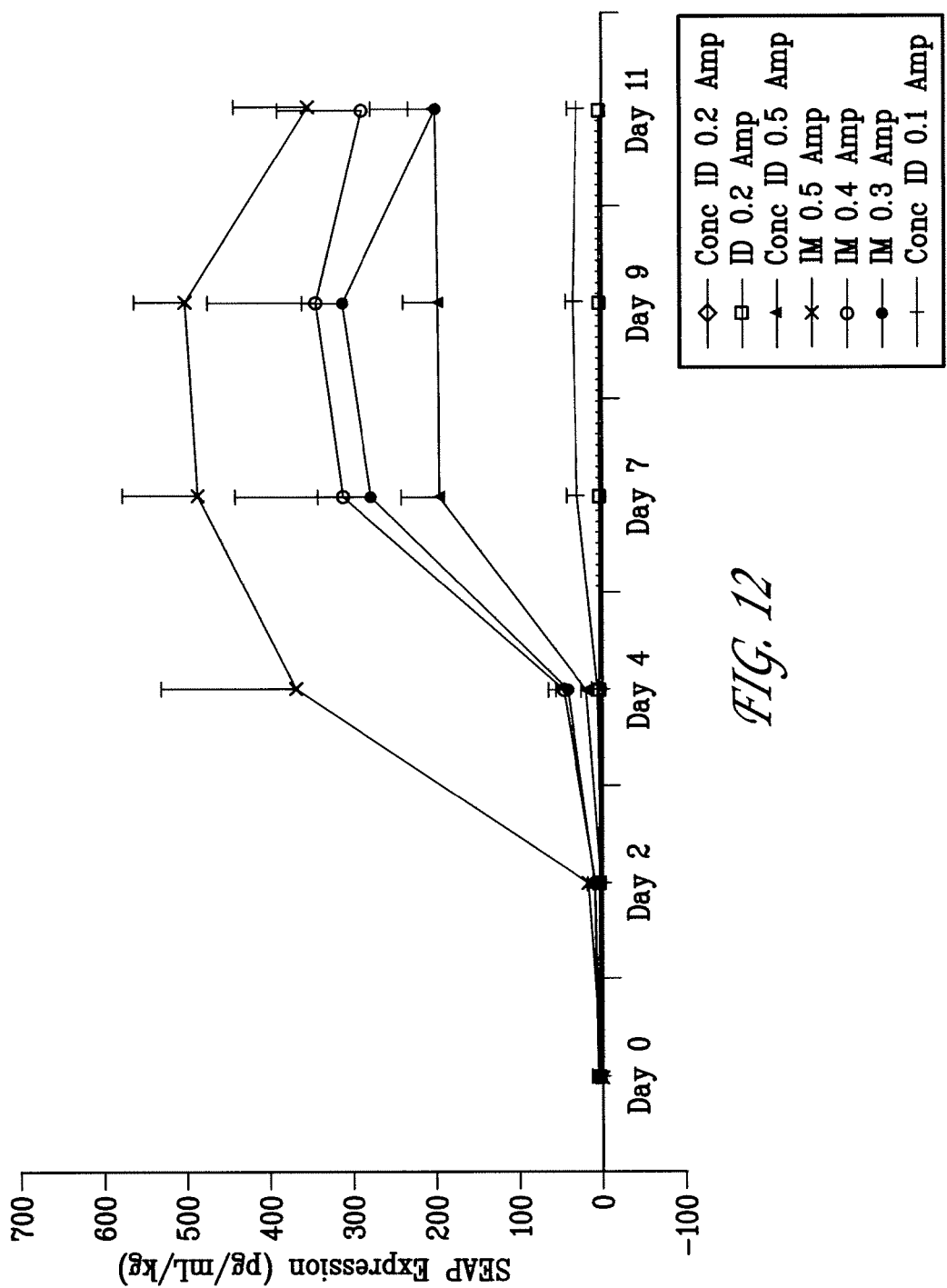
FIG. 12 shows a graph of SEAP expression levels (pg/mL/kg) over 11 days from the time of electroporation using the respective SEAP expressing plasmids.

SLAP expression was measured in serum samples using a chemilumiscent kit Phospha-Light Chemiluminescent Reporter Assay Kit (Applied Biosystems, Bedford, Mass.), per manufacturer instructions, as seen in FIG. 12. The lower limit of detection for the assay is 3 pg/mL. SEAP levels were higher in groups that were administered dilute plasmid versus the concentrated plasmid in IM injected animals electroporated at 0.5 Amp (43% higher, *P=0.024). Very low levels of detectable SEAP protein were found in serum from animals injected ID.

Figure 13:
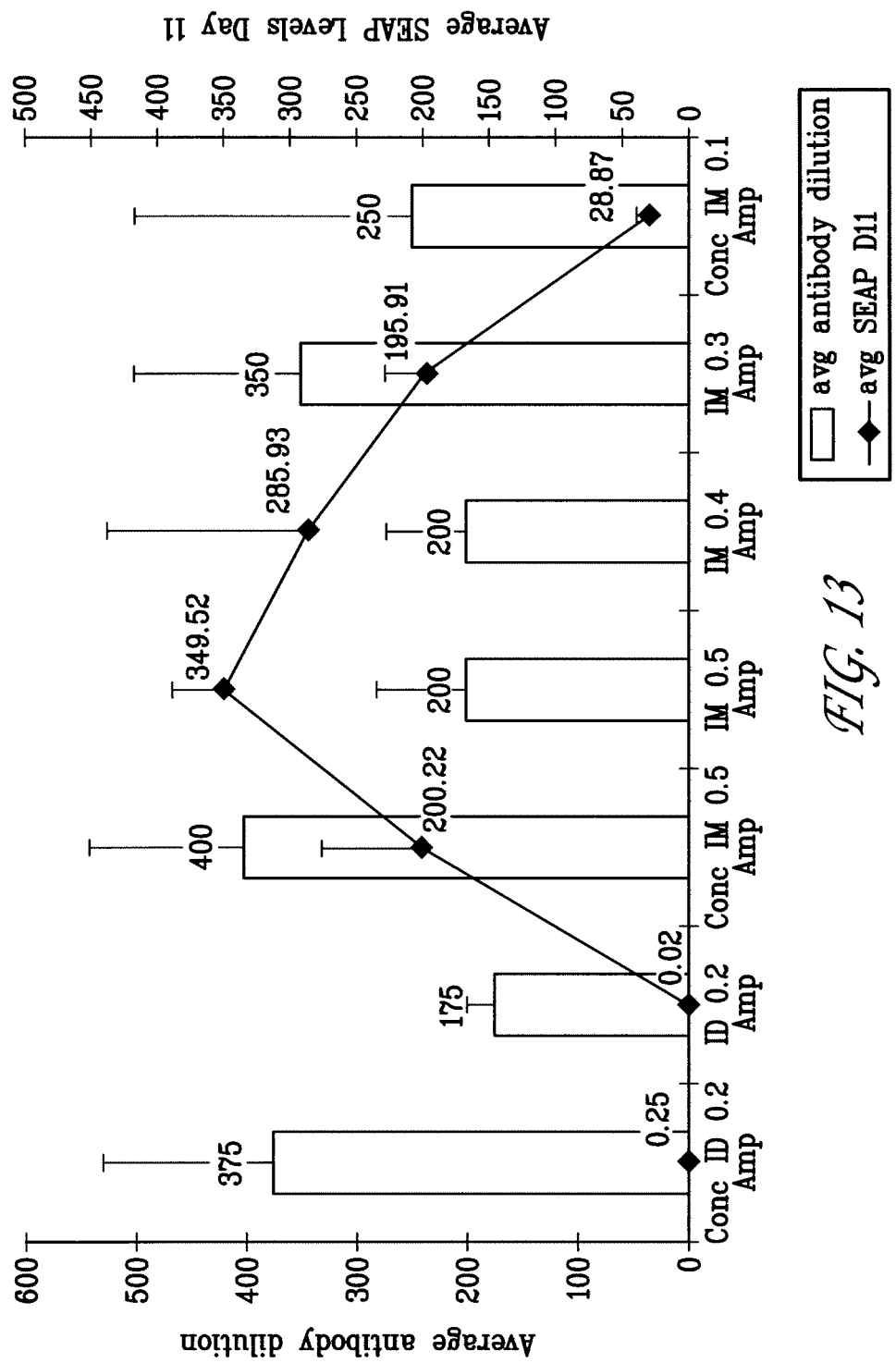
FIG. 13 shows a graph of the SEAP expression levels at day 11 for various samples along with related ELISA results (in average antibody dilution).

SEAP used in this study is a human protein and, thus, it elicits an immune response in pigs. The measurement of the antibody response using an ELISA was performed, and the results can be seen in the graph shown in FIG. 13. The antibody response in serum samples at Day 11 was graphed with the serum SEAP results at Day 11. The concentrated plasmid samples yielded among the highest mean antibody titers.

Figure 14:
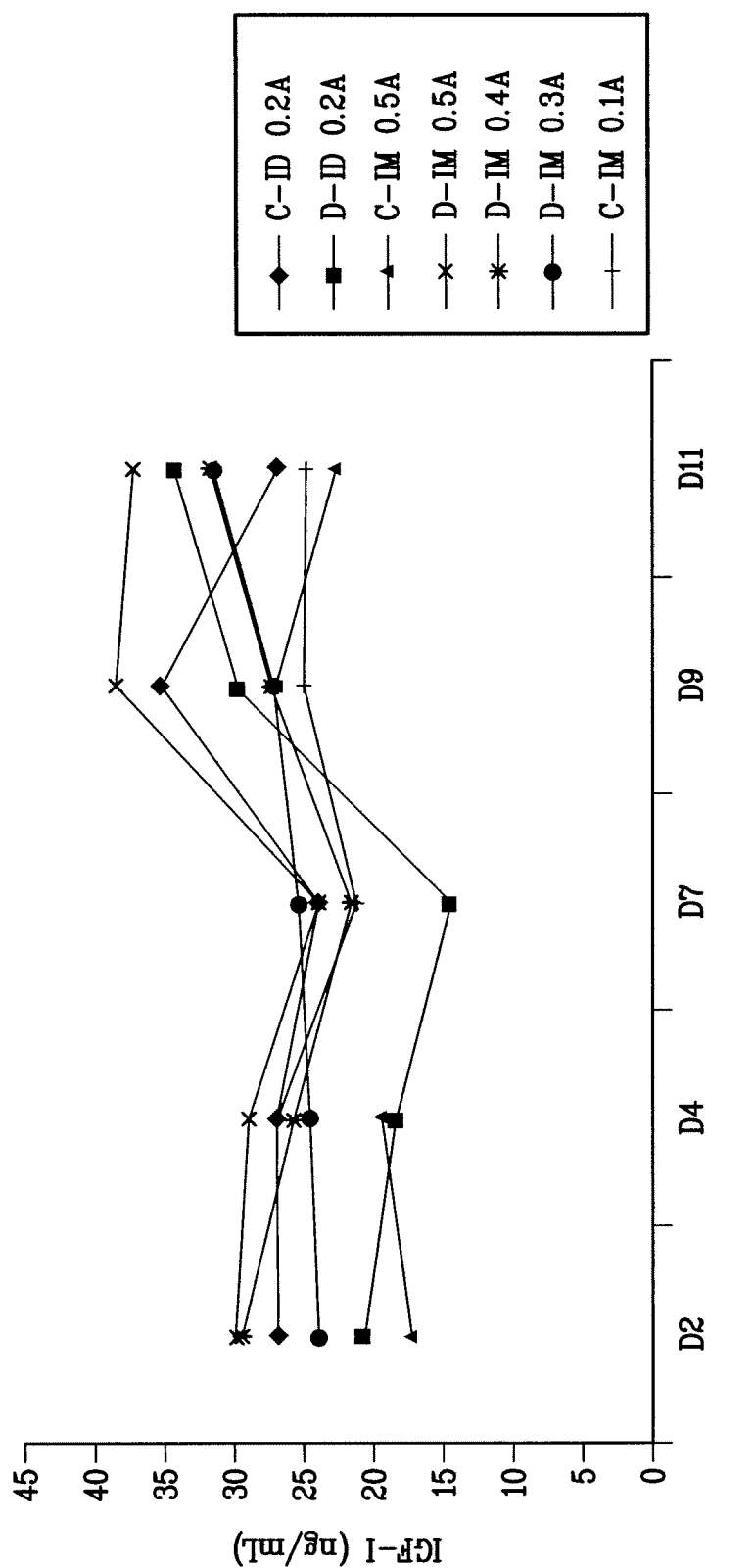
FIG. 14 shows a graph of IGF-I expression levels (mg/mL) over 11 days from the time of electroporation using the respective IGF-I expressing plasmids.

GHRH expression was measured using a downstream hormone in the GHRH axis, insulin-like growth factor I or IGF-I. The results can be seen in the graph shown in FIG. 14. IGF-I is more stable protein in the serum and readily measurable using and IGF-I RIA kit. Serum IGF-I levels at Day 11 post-injection were higher in the group administered non-concentrated plasmid IM (D-IM-0.5 A) as compared to the group administered concentrated plasmid IM (C-IM-0.5 A).

The results indicate that the volume and route of injection play a very important role in expression of expressed and secreted proteins and immunogenicity against those proteins. There was a significant difference between concentrated and non-concentrated DNA as far as expression versus immunogenicity.

IGF-I expression was higher in animals injected IM and electroporated with 0.5 Amps current intensity. Lower current intensities gave lower expression levels, but the small number of animals made the difference non-statistically different.

Example 6

Skin EP Studies in Pigs

Materials and Methods

Animals

Young hybrid pigs of mixed gender, three to six weeks of age, with weights between 25 and 40 kg, were used in the preliminary studies (n=5/group). Animals were housed at Stillmeadow, Inc., Sugarland, Tex., in accordance with the standards of the American Association for Accreditation of Laboratory Animal Care. Animals were group housed in pens with ad libitum access to food and water. Animals were acclimated for 5 days prior to the start of experiments.

Plasmids pEGFP-N1 or pSEAP-2 Basic Vector (Clontech Laboratories, Inc., Palo Alto, Calif.) were used in experiments 1 and 2, respectively. pEGFP-N1, used in experiment 1 (Exp. 1), encodes a red-shifted variant of wild-type green fluorescent protein (GFP) which has been optimized for brighter fluorescence and higher expression in mammalian cells (excitation maximum=488 nm; emission maximum=507 nm). A ubiquitous cytomegalovirus promoter (CMV) was driving the expression of a secreted embryonic alkaline phosphatase (SEAP) in the pSEAP-2 Basic Vector; this plasmid was used in pig experiment 2 (Exp. 2). Plasmids were obtained using a commercially available kit (Qiagen Inc., Chatsworth, Calif., USA). Endotoxin levels were at less than 0.01 EU/µg, as measured by Kinetic Chromagenic LAL (Endosafe, Charleston, S.C.). Plasmid preparations were diluted in sterile water and formulated 1% weight/weight with poly-L-glutamate sodium salt (MW=10.5 kDa average) (Sigma, St. Louis, Mo.), further HPLC purified at VGX Pharmaceuticals, Immune Therapeutics Division (The Woodlands, Tex.).

Intradermic/Subcutaneous (ID/SQ) Plasmid Administration and Electroporation (EP)

At Day 0 of Exp. 1, animals were weighed and anesthetized with isoflurane (5% induction, 2-3% maintenance). Two 3"×3" sites on each flank were shaved and cleaned carefully. One inch blocks were marked off using tattoo ink for later identification. Each plasmid injection was delivered in the center of the block. Animals received ID/SQ injections; at various EP conditions (see below), injection volumes and doses: plasmid dose, injection volume (50 µg/50 µL, 50 µg/100 µL, 100 µg/100 µL, and 200 µg/100 µL), current amplitude and pulse length were varied and biopsies of the treated area were scored by an independent observer blind to the identities of the treatment groups. Photographs of dissected skin sections were taken and fluorescence was measured 5 days post-injection. A numerical score was calculated based on the area of distribution and fluorescence intensity, as compared to the sample with the highest expression (0=no fluorescence, no distribution; 5=brightest fluorescence, greatest distribution). Square wave pulses were used in all experiments, and administered using a skin EP device, the CELLECTRA™ device (VGX Pharmaceuticals, Immune Therapeutics Division, The Woodlands, Tex.), which can deliver an adaptive constant current (constant current as experience by the underlying tissue). In all cases, adaptive constant-current parameters were between 0.1 and 0.4 Amps, with 2 or 3 pulses, for 20 milliseconds/pulse or 52 milliseconds/pulse, and with one second between pulses.

Figure 17A:
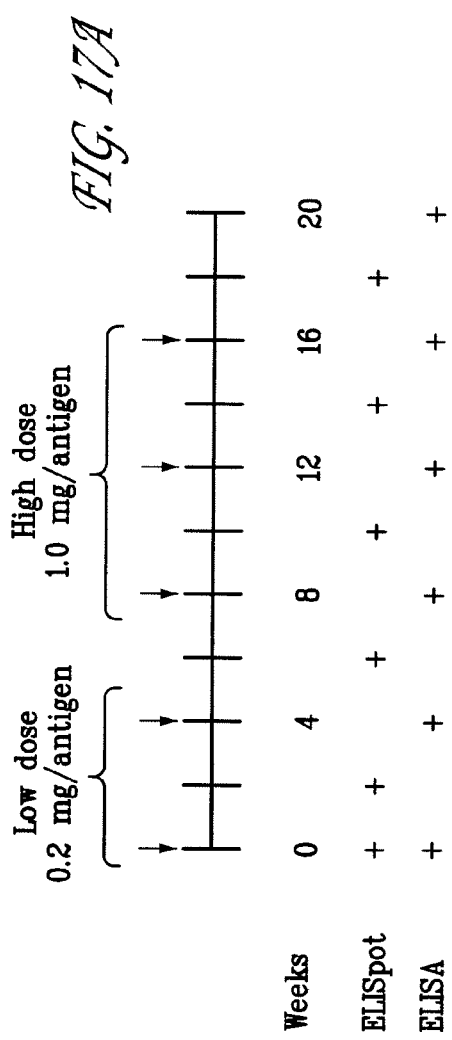
FIG. 17A shows that Rhesus macaques were immunized twice with a low dose (0.2 mg per antigen) of HIV-1 immunogens and plasmid-encoded rhesus IL-12 at weeks 0 and 4; and then immunized twice with a higher dose (1.0 mg per antigen) at weeks 8 and 12. Blood samples were collected approximately every two weeks for immune assays. ELISpots were performed two weeks following each immunization and ELISAs were performed at weeks 0, 4, 8, 12, 18.
Figure 17B:
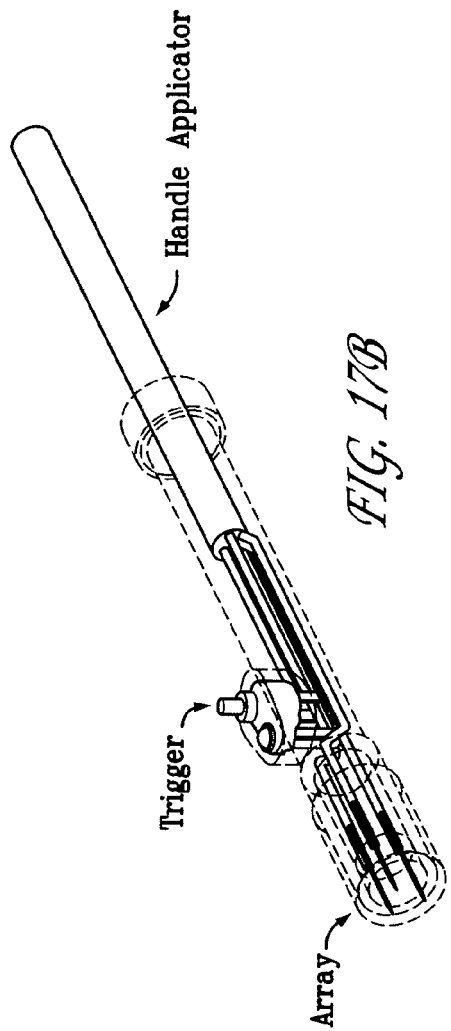
FIG. 17B displays a diagram of the skin electrode array and handle. The skin EP consists of a single-use array that has 3 stainless steel, 26 gauge electrodes, 3-5 mm in length. The array is attached to the handle applicator of the device; the EP procedure can be initiated by pressing the trigger button on the handle applicator.

Two types of arrays were used in Exp. 1: the electrode array previously used for intramuscular (IM) EP which is a circular array (1 cm diameter) of five equally spaced 21-gauge solid stainless steel needle electrodes, mounted on a non-conductive material; the ID/SC skin needle electrodes consisting of three 26-gauge solid stainless steel needle electrodes, 3 mm in length, placed in an isosceles triangle formation (two long sides are 5 mm in length, and the short side is 3 mm in length), mounted on non-conductive material (see also FIG. 17B).

In Exp. 2, the animals were injected ID/SQ and skin EP with 1 mg pSEAP, as either a standard plasmid preparation at 2 mg/mL (500 µL, similar to an IM injection), or as a concentrated plasmid preparation at 10 mg/mL (100 µL), and SEAP expression measured up to 11 days after plasmid administration.

Blood Collection and SEAP Assay

On days 0, 4, 7, and 11 of Exp. 2, animals were weighed at 8:30 AM and blood was collected by jugular vein puncture into MICROTAINER serum separator tubes. Blood was allowed to clot for 10 to 15 min at room temperature and subsequently centrifuged at 3000×g for 10 min and the serum stored at −80° C. until further analysis.

Serum samples were thawed and 50 µL was assayed for SEAP activity using the Phospha-Light Chemiluminescent Reporter Assay Kit (Applied Biosystems, Bedford, Mass.), per manufacturer instructions. The lower limit of detection for the assay is 3 pg/mL. More concentrated serum samples were diluted 1:10 in mouse serum before assaying for SEAP activity. All samples were read using LUMIstar Galaxy luminometer (BMG Labtechnologies, Offenburg, Germany).

Results

Exp. 1.

The highest GFP scores were achieved using both the skin needle electrode array and the IM electrode. However, the optimal results with the IM electrode required using double the plasmid dose at the identical concentration, 100 µg of plasmid formulated in 100 µL as compared to only 50 µg of plasmid formulated in 50 µL with the skin needle electrode array (FIG. 15). Furthermore, using the 0.2 Amps, 2 pulses, 52 ms/pulse, 1 sec between pulses, which we determined to be the optimized conditions for the skin EP, the procedure time was substantially reduced: the procedure time is only 4-5 seconds when using the skin EP device, and 80 seconds when using the IM array. As a general rule, a smaller volume (more concentrated solutions), with an adequate plasmid dose was found to yield better results.

Exp. 2

Figure 16:
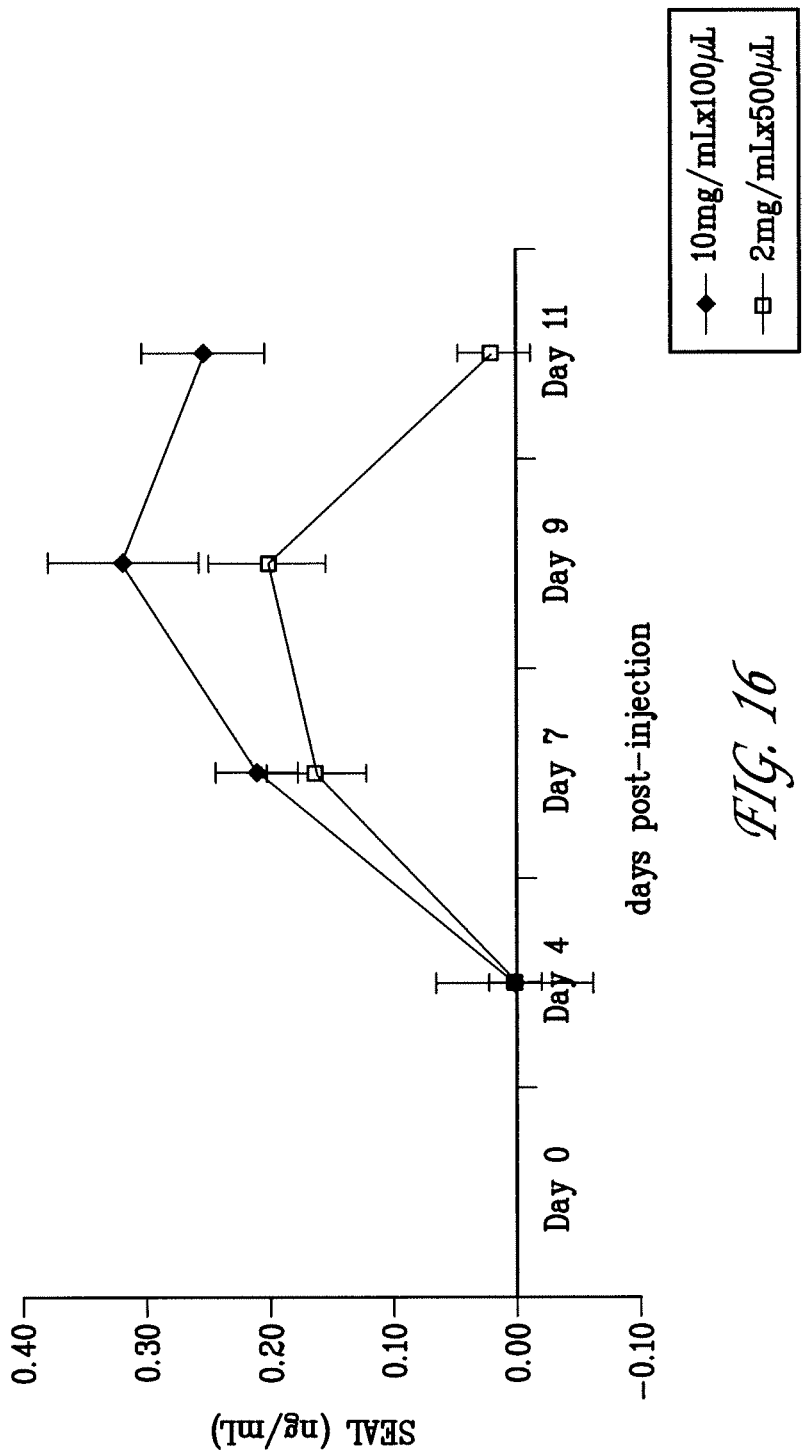
FIG. 16 displays a graph showing levels of secreted embryonic alkaline phosphatase (SEAP) detected in pig serum at 4-11 days after pSEAP administration. Animals received the same plasmid dose (1 mg), in either a concentrated formulation (at 10 mg/mL) or a regular formulation (at 2 mg/mL) (n=5/group). The data are shown as group mean responses±SEM.

Pigs were treated using the conditions determined in the previous experiment to be optimum for the ID/SQ plasmid delivery in conjunction with skin EP, i.e. 0.2 Amps, 2 pulses, 52 ms/pulse, 1 sec between pulses. Animals were administered the same plasmid quantity, 1 mg of pSEAP, using the small volume formulation, or a volume customary for IM+EP injections. Higher SEAP values were obtained using the concentrated plasmid preparation, and lower injection volumes (FIG. 16), P<0.05. These conditions were further validated in the non-human primate experiments.

Example 7

Primate Experiments

Rhesus macaques were immunized twice with a low dose of DNA (0.2 mg/antigen) and then immunized three times with a high dose of DNA (1.0 mg/antigen) by ID/SQ injection followed by skin EP. The two low dose immunizations resulted in weak cellular immune responses as determined by IFNγ ELISpot in both ID/SQ alone and ID/SQ injection followed by skin EP (ID/SQ+EP) groups. However, an increase in DNA dose boosted responses to 1,000 SFU/$10^6$ PBMCs in the ID/SQ group after 3 immunizations. The ID+EP group had 50% more IFNγ-producing cells than the ID/SQ group. The enhancement of immunogenicity in the ID/SQ+EP group was also seen in memory T cell responses with the ID/SQ+EP group having twice as many antigen-specific IFNγ-producing cells than the ID/SQ group. ID/SQ immunization alone did not result in a significant production of gag or env antibody titers (<50 endpoint titer). However, plasmid delivery with EP resulted in peak gag endpoint titers of 8800 and env endpoint titers of 1600. Finally, the co-immunization of plasmid-encoded rhIL-12 also resulted in a $T_H1$ polarized immune response as determined by an IL-4 ELISpot assay.

Materials and Methods

Animals

Rhesus macaques (*Macaca mulatta*), were individually housed at BIOQUAL, Inc. (Rockville, Md.), in accordance with the standards of the American Association for Accreditation of Laboratory Animal Care, with ad libitum access to food and water. Animals were allowed to acclimate for at least 30 days in quarantine prior to any experimentation.

Plasmids pGag4Y, pEY2E1-B, and WLV104 plasmids were used in this study. pGag4Y contains an expression cassette encoding for a gag protein of HIV. The Gag4Y gene was subcloned into the expression vector, pVax (Invitrogen, Carlsbad, Calif.), for further study. pEY-2E1-B contains an expression cassette encoding for the envelope of HIV clade B. WLV104M is a plasmid encoding a rhesus IL-12 gene. Plasmids were obtained using a commercially available kit (Qiagen Inc., Chatsworth, Calif., USA). Endotoxin levels were at less than 0.01 EU/µg, as measured by Kinetic Chromagenic LAL (Endosafe, Charleston, S.C.). Plasmid preparations were diluted in sterile water and formulated 1% weight/weight with poly-L-glutamate sodium salt (MW=10.5 kDa average) (Sigma, St. Louis, Mo.), further HPLC purified at VGX Pharmaceuticals, Immune Therapeutics Division, The Woodlands, Tex.

Immunization

HIV DNA vaccines were delivered ID/SQ in non-human primates with (n=3/group) and without (n=3/group) EP, using CELLECTRA™ adaptive constant current EP device (as in Example 3, above) and skin needle electrode arrays. Immunizations were performed four weeks apart, and animal were bled every two weeks to measure antibody and T-cell responses. The first two immunizations delivered 0.2 mg of each of two HIV antigens (gag and env) and IL-12 expressing plasmid as an adjuvant, in a volume of 200 µL, split into 2 ID/SQ injection sites per animal. The subsequent two immunizations were performed using 1 mg of each HIV vaccine and IL-12 plasmids (3 mg total) at the higher plasmid concentration (10 mg/mL) to achieve the higher plasmid dose in the identical volume as the previous two immunizations. Electroporation conditions were 0.2 Amps constant current, 2 pulses, 52 ms pulse length with 1 sec between pulses.

Blood Collection

Animals were bled every two weeks for the duration of the study. 10 mL of blood were collected in EDTA tubes. PBMCs were isolated by standard Ficoll-hypaque centrifugation and then resuspended in complete culture medium (RPMI 1640 with 2 mM/L L-glutamine supplemented with 10% heat-inactivated fetal bovine serum, 100 IU/mL penicillin, 100 µg/mL streptomycin, and 55 µM/L β-mercaptoethanol.) RBCs were lysed with ACK lysis buffer (Cambrex Bio Science, East Rutherford, N.J.).

Enzyme Linked Immunosorbant Assay (ELISA)

Ninety-six well plates were coated overnight with 100 ng/well of recombinant HIV-1 IIIB p24 or gp120 (ImmunoDiagnostics, Woburn, Mass.) to determine HIV gag and env responses respectively. Plates coated with 100 ng/well of bovine serum albumin served as a negative control. Plates were blocked with 3% BSA-PBST for 1 hour at 37° C. Plates were then incubated with four-fold serial serum dilutions for 1 hour at 37° C. Goat anti-monkey IgG horseradish peroxidase conjugated antibody was then added at a 1:10,000 dilution (MP Biomedicals, Aurora, Ohio) to the plates and incubated for 1 hour at 37° C. Tetramethylbenzidine (R&D systems, Minneapolis, Minn.) was used to develop the plates and reactions were stopped with $2NH_2SO_4$. Optical densities (OD) were then measured.

IgG end-point titers were defined as the reciprocal serum dilution that resulted in OD values that were greater than twice the average OD value of the BSA wells.

Enzyme Linked Immunospot Assay (ELISpot)

ELISpot were performed by using IFNγ or IL-4 capture and detection antibodies (MabTech, Sweden). Antigen specific responses were determined by subtracting the number of spots in the negative control wells from the wells containing peptides. Results are shown as the mean value (spots/million splenocytes) obtained for triplicate wells.

Statistical Analysis

Data are analyzed using Prism Graphpad software, and expressed as means±SEM.

Non-Human Primate Study Design

Rhesus macaques were immunized with optimized HIV-1 gag and env constructs and plasmid-encoded rhesus IL-12 per designed specified in FIG. 17A; the device used in the pigs experiments were also used in the non-human primates (FIG. 17B). Three animals were immunized by ID/SQ injection and three animals were immunized with ID/SQ injection followed by skin electroporation (ID/SQ+EP). The animals were immunized five times at weeks 0, 4, 8, 12, 16. Blood was collected every two weeks and ELISpot assays were performed two weeks after each immunization, while ELISA assays were performed four weeks after each immunization.

ELISpot Analysis

The induction of the cellular immune response after each immunization was determined by IFNγ ELISpot (FIG. 18). After one low dose immunization of 0.2 mg per antigen, both the ID/SQ and the ID/SQ+EP groups had very weak responses (72±11 SFU/$10^6$ PBMCs and 85±34 SFU/$10^6$ PBMCs, respectively). A second low dose immunization doubled the number of IFNγ-producing cells in the ID/SQ group (173±77 SFU/10 PBMCs) and tripled the response in the ID/SQ+EP group (287±34 SFU/106 PBMCs). Having observed a very weak cellular response following the two low dose immunizations we used a higher dose (1 mg per antigen) of DNA for the next three immunizations. The immune response did not increase significantly with the third immunization in the ID/SQ group (176±72 SFU/$10^6$ PBMCs). However the ID/SQ+EP group did boost with the higher dose to double the amount of antigen-specific IFNγ-producing cells (383±162 SFU/$10^6$ PBMCs). The animals were immunized for a fourth time with the 1 mg dose of DNA. A three-fold increase in IFNγ response was observed in the ID/SQ group compared to the previous immunization (376±210 SFU/$10^6$ PBMCs). As with the third immunization, delivery of the high dose of DNA with skin EP resulted in a doubling of the IFNγ response (1466±762 SFU/$10^6$ PBMCs). These high levels of antigen-specific responses were maintained through the final immunization (1453±873 SFU/$10^6$ PBMCs). The last immunization further doubled the amount of IFNγ-producing cells in the ID/SQ group (927±191 SFU/$10^6$ PBMCs).

Memory T cell Responses

The induction of a robust memory T cell response is an important aspect of a successful vaccine. To evaluate the memory T cell population induced by the ID/SQ DNA immunizations, ELISpot analysis was performed 10 weeks after the last DNA vaccination (FIG. 19). The ID/SQ+EP group had a memory IFNγ response that was twice the magnitude of the ID/SQ group (998±290 and 449±108 SFU/106 PBMCs, respectively).

$T_H2$ T Cell Responses

Figure 20:
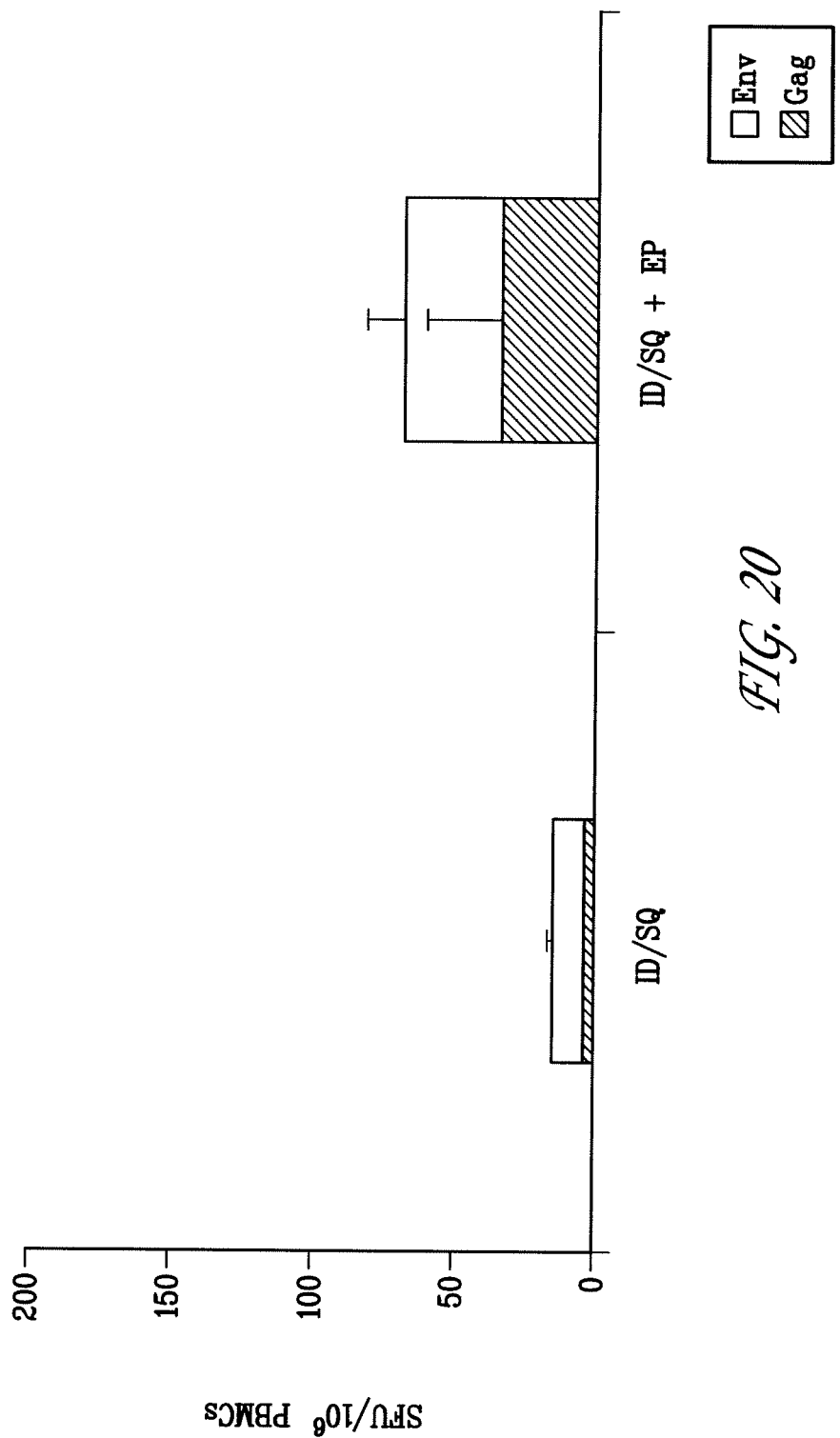
FIG. 20 displays a graph showing induction of $T_H1$ and not $T_H2$ mediated cellular response following ID/SQ immunization of HIV-1 gag, env and plasmid rhIL-12. An IL-4

Studies using gene gun for skin immunizations have demonstrated the induction of $T_H2$ biased T cell responses. However it has been shown that this bias could be reversed to a $T_H1$ response if IL-12 protein was also delivered. The co-delivery of rhesus IL-12 in an ID DNA immunization was performed to determine whether its co-delivery would lead to an induction of $T_H1$ biased response (FIG. 20). The induction of antigen-specific $T_H2$ responses was determined by an IL-4 ELISpot assay 10 weeks after the final immunization. All animals in the ID/SQ only group had a negative IL-4 response (>50 SFU/$10^6$ PBMCs) and only one animal in the ID/SQ+EP group had a positive IL-4 response (136 SFU/$10^6$ PBMCs), suggesting a predominant $T_H1$ response.

Humoral Responses

A weakness of DNA immunizations lies in its inability to induce antibody responses in non-human primates and in human clinical studies. Each group's ability to induce both HIV-1 gag and env specific antibody titers to recombinant p24 and gp160 antigens was determined by an ELISA assay (FIG. 21). For both antigens, the ID/SQ group did not show significant antibody titers (<50 endpoint titer). The ID/SQ+ EP group developed a low level of antibodies after the second low dose immunization (endpoint titer: 100±50). However, a greater induction of antibodies was seen after the dose of DNA delivered was increased in the third immunization with the high dose of DNA (2220±1000). Antibody titers were boosted through the fourth immunization (8800±4000). The env antibody responses also reflected the results we observed with the gag antigen with the ID/SQ group having low titers (<50 endpoint titer) and the ID/SQ+ EP group reaching a maximum endpoint titer of 1600±800.

IM vs ID/SQ Electroporation

Rhesus macaques were immunized three times with the same HIV gag, env and rhIL-12 constructs (as discussed, above) at 1.0 mg/mL by IM immunization. Comparing the induction of cellular immune responses, both the IM and the ID/SQ routes had similar levels of IFNγ-producing cells after the first two immunizations. In contrast, immunization by ID/SQ+EP resulted in high levels of HIV gag antibody titers after one high dose immunization compared to IM+EP. After two immunizations, the ID/SQ+EP group had HIV gag endpoint titers that were twice that of the IM+EP group.

In these experiments, we used skin needle electrodes for delivery into the ID/SQ compartment, and compare the resulting immune response to those achieved after IM+EP (see Table 1).

TABLE 1

Comparison of immune responses induced by electroporation via IM or ID/SQ route. IFNγ ELISpot and HIV gag ELISA results taken after 3 high dose (1.0 mg/antigen) immunizations are shown.

|  | IM | ID | IM + EP | ID + EP |
|---|---|---|---|---|
| ELISpot Total gag and env responses (SFU/10^6 PBMCs) | | | | |
| 1 | 136 ± 51 | 95 ± 38 | 482 ± 181 | 635 ± 171 |
| 2 | 223 ± 76 | 376 ± 210 | 1924 ± 417 | 1466 ± 762 |
| 3 | 2042 ± 311 | 927 ± 191 | 6300 ± 378 | 1465 ± 762 |
| ELISA Gag Endpoint Titer | | | | |
| 1 | <50 | <50 | 150 | 2200 |
| 2 | <50 | <50 | 4800 | 8800 |
| 3 | <50 | <50 | 12800 | 2150 |

Example 8

DNA Vaccination in Mice using Skin EP

A. Plasmid Constructs

A ubiquitous cytomegalovirus (CMV) promoter or a muscle specific synthetic promoter (SPc5-12) drives the expression of human secreted embryonic alkaline phosphatase (SEAP) in the pSEAP-2 Basic Vector used in mouse experiments 1 and 3 (Exp. 1 and Exp. 3). A red-shifted variant of wild-type green fluorescent protein (GFP)-expressing plasmid, pEGFP-N1, which has been optimized for brighter fluorescence and higher expression in mammalian cells (excitation maximum=488 nm; emission maximum=507 nm) has also been used in the reporter gene experiments (Exp. 2). Plasmids were obtained using a commercially available kit (Qiagen Inc., Chatsworth, Calif.). Endotoxin levels were at less than 0.01 EU/µg, as measured by Kinetic Chromagenic LAL (Endosafe, Charleston, S.C.). Consensus HA and NA constructs were generated by analyzing primary virus sequences from 16H5 viruses that have proven fatal to humans in recent years, and over 40 human N1 viruses. These sequences were downloaded from the Los Alamos National Laboratory's Influenza Sequence Database. After generating the consensus sequences, the constructs were optimized for mammalian expression, including the addition of a Kozak sequence, codon optimization, and RNA optimization. These constructs were then subcloned into the pVAX vector (Invitrogen, Carlsbad, Calif.). Unless indicated otherwise, plasmid preparations were diluted in sterile water and formulated 1% weight/weight with poly-L-glutamate sodium salt (LGS) (MW=10.5 kDa average) (Sigma, St. Louis, Mo.), further HPLC purified at VGX Pharmaceuticals, Immune Therapeutics Division (The Woodlands, Tex.).

B. Reporter Gene Experiments in Mice

This study tested the delivery and expression of SEAP or EGFP-expressing plasmids to determine which electroporation parameters (lowest effective current), lag time (time between injection and onset of electroporation), formulation and target muscle impact expression and antibody levels. Animals were electroporated using the CELLECTRA™ skin EP device (including use of 3×26 gauge electrodes) with varying current and lag time for either IM or ID injection.

In a first experiment (Exp. 1), groups of C57/Bl6 mice (n=10/group) were injected with 10 μg of a plasmid expressing SEAP under the control of a muscle-specific synthetic promoter (pSPc5-12-SEAP) into the tibialis anterior (TA) or gastrocnemius (G) muscle at a lag time of 4 or 80 seconds and 0.1 A constant current. A control group received the plasmid in the TA without EP (No EP). Additional groups of animals received in equimolar concentration an expression cassette with no plasmid backbone (NB), but identical promoter, transgene and 3' polyadenylation signal, in TA and G muscles with and without EP.

In the second experiment (Exp. 2), groups were mice (n=4) were injected with 50 μg of pCMV-EGFP, in a total volume of 5 or 25 μL, respectively, for a final plasmid concentration of 10 mg/mL or 2 mg/mL, either IM or ID. Photographs of dissected skin and muscle sections were taken and fluorescence was measured 5 days post-injection. Treated area was scored by an independent observer blind to the identities of the treatment groups. A numerical score was calculated based on the area of distribution and fluorescence intensity, as compared to the sample with the highest expression (0=no fluorescence, no distribution; 5=brightest fluorescence, greatest distribution).

In the third mouse experiment (Exp. 3), 16 groups×5 mice per group for a total of 80 mice were used (TABLE 2). Mice (n=5/group) were injected with 50 μg of CMV-SEAP (at 10 mg/mL) at varying formulations (saline, saline+1% LGS, water, water+1% LGS) and current intensities. Animals were electroporated with 4 seconds lag time with varying current (0.1 A to 0.2 A) for IM injection in the TA or G muscle.

TABLE 2

| Groups for the CMV-SEAP formulation experiment in mice (Exp. 3) | | | | | |
|---|---|---|---|---|---|
| Group | Formulation | Conc (mg/mL) | Total Dose (μg/animal) | EP | n |
| 1 | Saline | 10 | 50 | 0.2 | 5 |
| 2 | Saline | 10 | 50 | 0.1 | 5 |
| 3 | Saline | 10 | 50 | 0.2 | 5 |
| 4 | Saline | 10 | 50 | 0.1 | 5 |
| 5 | Saline + LGS | 10 | 50 | 0.2 | 5 |
| 6 | Saline + LGS | 10 | 50 | 0.1 | 5 |
| 7 | Saline + LGS | 10 | 50 | 0.2 | 5 |
| 8 | Saline + LGS | 10 | 50 | 0.1 | 5 |
| 9 | Water | 10 | 50 | 0.2 | 5 |
| 10 | Water | 10 | 50 | 0.1 | 5 |
| 11 | Water | 10 | 50 | 0.2 | 5 |
| 12 | Water | 10 | 50 | 0.1 | 5 |
| 13 | Water + LGS | 10 | 50 | 0.2 | 5 |
| 14 | Water + LGS | 10 | 50 | 0.1 | 5 |
| 15 | Water + LGS | 10 | 50 | 0.2 | 5 |
| 16 | Water + LGS | 10 | 50 | 0.1 | 5 |

In all cases, animals were acclimated for 3 days, weighed and ear-tagged. Food and water were available ad libitum for the length of the experiment. On Study Day 0 animals were weighed, bled and anesthetized using the combination anesthetic for rodents—xylazine (37.5 mg/mL; 0.05 mL/30 grams body weight), ketamine (1.9 mg/mL; 0.016 mL/10 grams body weight), acepromazine (0.37 mg/mL; 0.025 mL/15 grams body weight), plasmid was administered per design and electroporated. For Exp. 1 and 3, blood was collected via retro-orbital bleed and allowed to clot. All collected blood was centrifuged to isolate serum and plasma and then aliquoted into tubes on ice for SEAP assays and anti-SEAP ELISA, as performed previously with minor modifications. After Day 14, all animals were exsanguinated under surgical plane of anesthesia.

C. Analysis

Blood Collection

On days 0, 4, 7, and 11, mice were weighed and blood collected via retro-orbital bleed into microfuge tubes, respectively. Blood was allowed to clot for 10 to 15 min at room temperature and subsequently centrifuged at 3000×g for 10 min and the serum stored at −80° C. until further analysis.

SEAP Assay

Serum samples were thawed and 50 μL was assayed for SEAP activity as previously described using the Phospha-Light Chemiluminescent Reporter Assay Kit (Applied Biosystems, Bedford, Mass.), per manufacturers' instructions. The lower limit of detection for the assay is 3 pg/mL. More concentrated serum samples were diluted 1:10 in control species-specific serum before assaying for SEAP activity. All samples were read using LUMIstar Galaxy luminometer (BMG Labtechnologies, Offenburg, Germany).

SEAP Indirect ELISA

Immunogenicity to the human SEAP protein was measured in mice using the following modified procedure. Nunc Maxisorb (Rochester, N.Y.) plates were coated with purified human placental alkaline phosphatase in PBS (100 μl containing 100 nanograms/well of human placental alkaline phosphatase (Sigma)) overnight at 4° C. Plates were decanted and washed three times. Plates blocked using 1% BSA (Sigma) in 0.05% Tween 20 in PBS (blocking solution) and incubated for 2 hours room temperature. Serum samples were diluted 1:100 followed by serial dilutions of 1:4 in 1% BSA (Sigma) in 0.05% Tween 20 in PBS in separate dilution plates. The block solution was decanted from plates. 100 μl of diluted test serum was added to each well and incubated at room temperature for 2 h. Serum dilutions were decanted and washed three times. Secondary antibody was diluted (rabbit anti-mouse conjugated with horseradish peroxidase) 1:1000 in 1% BSA in 0.05% Tween 20 in PBS and incubated 1 h at room temperature. Plates were decanted and washed. 100 μl of o-phenylenediamine (OPD) substrate per well was added (0.67 mg/mL) in 0.1M citric acid buffer and incubated 8 min; 100 μl of 1 M $H_2SO_4$ was added to stop the reaction. Absorbance was measured at 490 nm on Spectramax Plus 384 plate reader (Molecular Devices, Sunnyvale, Calif.).

D. Results on Mice

SEAP Expression is Dependent on the Target Muscle

Expression was increased if the SEAP-expressing plasmid injection is administered into the TA (FIG. 22) versus the G muscle, at both 80 s and 4 s lag time between injection and EP using the skin EP device. When the SPc5-12-SEAP plasmid was injected into the TA muscle, serum SEAP levels were 285 fold higher than in control animals that received the plasmid in the absence of EP (P<1.3 E−21); no difference was observed between the 80 s and 4 s lag time for the TA muscle (357±6 vs. 357±6.2 pg/mL/g); the injection under identical conditions into the G muscle resulted in SEAP levels of 90 to 182 fold higher than controls (G 80 s vs. no EP controls, P<0.003; G 4 s vs. no EP controls, P<7.7 E−06). When plasmid fragments containing the expression cassettes only were injected in the TA and G (no backbone (NB), but identical promoter, transgene and 3' polyadenylation signal) in an equimolar formulation, the expression levels were 210-250 fold higher than controls that did not receive IM+EP (80 s vs. no EP, P<1.8 E−08; 4 s vs. no EP, P<3.8 E−05). SEAP expression in the TA 80 s was 24% higher than the NB 80 s group (P<0.008), while TA 4 s was 37% higher than the NB 4 s group (P<0.004). Both groups administered C5-12-SEAP and NB without EP (No EP) demonstrated negligible SEAP expression.

GFP Expression

GFP expression was visualized after careful dissection of the injection site and scored by an observer blinded to the treatment groups. GFP scores were higher in groups administered concentrated plasmid in both ID (4.63±0.24 vs. 3.25±0.14, P=0.01) and IM (4.75±0.14 vs. 3±0.54, P=0.01) injected animals versus non-concentrated plasmid (FIG. 23). In these studies concentrated formulations (up to 10 mg/mL) were associated with higher overall expression. Based on the results from this experiment, plasmids were used at a concentration of 10 mg/mL in Exp. 3.

SEAP Expression is Dependent on Formulation and Current Intensity

The differences in SEAP levels were assessed when SEAP transgene is under control of a ubiquitous promoter (versus a muscle-specific promoter as used in Exp. 1). Consistent with the previous experiments, expression increased if the plasmid injection-EP procedure is performed in the TA (FIG. 24) versus the G muscle (P=0.05). In this particular experiment, saline+LGS formulation resulted in higher serum SEAP levels as compared to saline formulation (41.1±7.9 pg/mL/g vs. 31.0±5.9 pg/mL/g, respectively), although this did not attain statistical significance due to high intra-group variability. In general, animals that were electroporated at 0.1 A current setting yielded slightly higher SEAP expression than animals that received identical LGS plasmid formulation, delivered at 0.2 A constant current. Nevertheless, the animals that received 0.2 A plasmid formulated into water yielded significant lower SEAP levels than those receiving 0.1 A for the same muscle (P<0.05 for TA and P<0.001 For G). When LGS was added to the water formulation, the differences were not significant for the TA muscle, but were still maintained for the G muscle (P<0.04).

Induction of Anti-SEAP Antibodies

Formulation of SEAP plasmid with saline+LGS yielded higher protein expression, however, the titers of anti-SEAP antibodies were lower when compared with animals injected with SEAP plasmid formulated in water+LGS (FIG. 25), although this did not attain statistical significance due to high intra-group variability.

Example 9

Intradermal Delivery Comparisons with Intramuscular Delivery in Primates

PRIMATE sera

A/Vietnam/2003/04 HI Titers on 1% Horse RBC

| Group | PRIMATE ID | Study Group | HI titer wk 6 |
|---|---|---|---|
| H5 + M2 | 4497 | C | 80 |
| IM CELLECTRA™ | 4498 | C | 80 |
| 1 mg per plasmid | 4499 | C | 40 |
| | 4500 | C | 80 |
| | 4501 | C | <20 |

-continued

| | | | |
|---|---|---|---|
| H5 + M2 | 4520 | D | 160 |
| ID CELLECTRA ™ | 4521 | D | 80 |
| 1 mg per plasmid | 4522 | D | 160 |
| | 4523 | D | 40 |
| | 4534 | D | 160 |
| H5 + env + 2 HPV | 4508 | G | 160 |
| IM alone | 4510 | G | <20 |
| 1 mg per plasmid | 4511 | G | <20 |
| | 4512 | G | <20 |
| | 4513 | G | <20 |
| negative control | 4529 | H | <20 |
| | 4530 | H | <20 |
| | 4531 | H | <20 |
| | 4532 | H | <20 |
| | 4533 | H | <20 |
| H5 ref. sera | | | 1,600 |

| DNA Constructs | |
|---|---|
| 1 | HIV Env Clade A |
| 2 | HIV Env Clade C |
| 3 | HIV Env Clade D |
| 4 | HIV Gag |
| 5 | HIV Pol |
| 6 | Flu H5 |
| 7 | Flu NA |
| 8 | Flu M2 NP |
| 9 | HPV 16 E6/E7 |
| 10 | HPV 18 E6/E7 |
| 11 | IL12 |

| Study Group | DNA Constructs | No of Animals | Route of Admin | Dose | Total DNA (mg)/Animal |
|---|---|---|---|---|---|
| A | DNA 1 + 2 + 3 + 4 + 5 + 11 | 5 | IM CELLECTRA ™ | 1 mg/Const | 6 |
| B | DNA 1 + 2 + 3 + 4 + 5 + 11 | 5 | ID CELLECTRA ™ | 1 mg/Const | 6 |
| C | DNA 6 + 9 | 5 | IM CELLECTRA ™ | 1 mg/Const | 2 |
| D | DNA 6 + 9 | 5 | ID CELLECTRA ™ | 1 mg/Const | 2 |
| E | DNA 7 + 8 + 10 | 5 | IM CELLECTRA ™ | 1 mg/Const | 3 |
| F | DNA 7 + 8 + 10 | 5 | ID CELLECTRA ™ | 1 mg/Const | 3 |
| G | DNA 1 + 6 + 9 + 10 | 5 | IM Syringe | 1 mg/Const | 4 |
| H | Negative Control | 5 | N/A | | 0 |
| | TOTAL | 40 | | | |

Rhesus macaques were immunized in these studies. Animals were acclimated for 2 months prior to the start of experiments. The study progressed as follows: Week O-performed 1st immunization (plasmid dose administration) and baseline bleed; Week 2 performed bleed; Week 3 performed 2nd immunization (plasmid dose administration); Week 5 performed bleed; Week 6 performed 3rd immunization (plasmid dose administration) and bleed; Week 8 performed bleed.

All plasmids were formulated at 10 mg/mL in water for injection+1% LGS, as described in previous examples, above, and mixed into a single solution PER STUDY GROUP(S) (Groups A-H, in above table). The correct injection volume for each group designated IM CELLECTRA™ ID CELLECTRA™ and 1M Syringe was calculated. For the ID administration, if the required injection volume surpassed 100 μL per site, the formulation was split into a number of injection sites (2, 3, or 6 depending on how many total mg of vaccine were administered). The animals that received IM injection(s) were given the entire formulation in one single site.

The CELLECTRA™ adaptive constant current device used in the pigs experiments and nonhuman experiments described in the Examples, above, were also used in these non-human primate experiments. The electroporation conditions were as following: for the IM injection and electroporation groups, the conditions were: 0.5 Amps, 52 msec/pulse, three pulses, 4 sec delay between plasmid injection and electroporation. For the ID injection and electroporation groups, the conditions were: 0.2 Amps, 52 msec/pulse, three pulses, 4 sec delay between plasmid injection and electroporation.

Hemagglutination Inhibition (HI) Assay— monkey sera were treated with receptor destroying enzyme (RDE) by diluting one part serum with three parts enzyme and incubated overnight in 37° C. water bath. The enzyme was inactivated by 30 min incubation at 56° C. followed by addition of six parts PBS for a final dilution of ⅒. HI assays were performed in V-bottom 96-well microtiter plates, using four HA units of virus and 1% horse red blood cells. The data presented herein are the results after the second immunization (bleed collected before the third immunization).

What is claimed is:

1. An electroporation device configured to deliver to a desired tissue of a mammal a pulse of energy producing a constant current similar to a preset current input by a user, wherein the desired tissue is subcutaneous tissue or intradermic tissue, the electroporation device comprising:
   an electroporation component capable of delivering the pulse of energy that produces the constant current in the desired tissue, the electroporation component having a feedback mechanism; and
   a skin electrode assembly including an electrode array having a plurality of skin electrodes in a spatial arrangement, wherein the electrode array comprises at least three skin electrodes, wherein the skin electrodes are needle electrodes, and wherein the skin electrode assembly receives the pulse of energy from the electroporation component and delivers same to the desired tissue through the skin electrodes,
   wherein at least one of the plurality of skin electrodes is neutral during delivery of the pulse of energy and measures impedance in the desired tissue and communicates said impedance to the electroporation component,
   wherein the feedback mechanism can receive the measured impedance and can adjust the pulse of energy delivered by the electroporation component to maintain the constant current,
   wherein the feedback mechanism is performed by an analog closed-loop circuit,
   wherein the neutral electrode measures the impedance in the desired tissue and communicates the impedance to the feedback mechanism, and the feedback mechanism responds to the impedance and adjusts the pulse of energy to maintain the constant current at a value similar to the preset current, and
   wherein the feedback mechanism maintains the constant current continuously and instantaneously during the delivery of the pulse of energy.

2. The device of claim 1, wherein the three skin electrodes have a spatial arrangement that is a triangle.

3. The device of claim 2, wherein the triangle is an isosceles triangle.

4. The device of claim 3, wherein the isosceles triangle has sides of 5 mm in length and a base of 3 mm in length.

5. The device of claim 1, wherein the plurality of skin electrodes can deliver the pulse of energy in a decentralized pattern.

6. The device of claim 5, wherein the plurality of skin electrodes can deliver the pulse of energy in the decentralized pattern through the control of the skin electrodes under a programmed sequence, the programmed sequence being input by a user to the electroporation component.

7. The device of claim 6, wherein the programmed sequence comprises a plurality of pulses delivered in sequence, wherein each pulse of the plurality of pulses is delivered by at least two active skin electrodes with one neutral skin electrode that measures impedance, and wherein a subsequent pulse of the plurality of pulses is delivered by a different one of at least two active skin electrodes with one neutral skin electrode that measures impedance.

8. The device of claim 1, wherein the feedback mechanism is performed by either hardware or software.

9. The device of claim 1, wherein the electroporation device includes a safety feature, the safety feature being a voltage cap that prevents the device from delivering the pulse of energy to the tissue when adjustment to the pulse of energy would yield a voltage above the voltage cap.

10. The device of claim 1, further comprising:
    a controller that receives the inputs from the user and controls the electroporation component to deliver the pulse of energy according to the inputs.

11. The device of claim 10, wherein the controller is a single chip microcontroller.

12. The device of claim 1, further comprising:
    a current waveform generator in communication with the electroporation component and in electrical communication with the skin electrode assembly; the current waveform generator generating a current pulse train waveform for delivery through the skin electrode assembly.

13. The device of claim 12, wherein the user inputs a programmed sequence to the electroporation component, which communicates the programmed sequence to the current waveform generator; wherein the current waveform generator is capable of generating the current pulse train waveform according to the provided programmed sequence.

14. The device of claim 12, wherein the current waveform generator is a power-transistor analog circuit.

15. The device of claim 1, further comprising:
    an impedance tester capable of testing for establishment of an electrical connection between the skin electrodes and the desired tissue.

16. The device of claim 1, further comprising a waveform logger in communication with the electroporation component.

17. The device of claim 16, wherein the waveform logger is capable of recording electroporation voltage and current waveforms continuously during the delivery of the pulse of energy.

18. The device of claim 16, wherein the waveform logger is capable of recording electroporation voltage and current waveforms at a rate of 2000 samples per second.

19. The device of claim 1, further comprising an input device in direct communication with the user and the electroporation component, the input device capable of receiving input commands and communicating the input commands to the electroporation component.

20. The device of claim 19, wherein the input device is a numeric keypad or a touch screen.

21. The device of claim 1, further comprising a status reporting element in communication with the electroporation component.

22. The device of claim 21, wherein the status reporting element is an information display panel, an audible notification, a light-emitting diode, or a combination thereof.

23. The device of claim 22, wherein the status reporting element reports confirmation of generation of pulse of energy and delivery of the constant current.

24. The device of claim 1, further comprising a communication port in communication with the electroporation component.

25. The device of claim 1, further comprising a memory component in communication with the electroporation component.

26. The device of claim 1, further comprising a power source in communication with the electroporation component.

27. The device of claim 26, wherein the power source is a battery.

28. The device of claim 1, wherein the electrode array is disposable and removably connected to the skin electrode assembly.

29. The device of claim 28, wherein the disposable electrode array is a skin electrode disk.

30. The device of claim 29, wherein the skin electrode disk is sterilizable.

31. The device of claim 1, wherein the electroporation component comprises:
a controller;
a waveform generator in electronic communication with the controller;
a waveform logger in electronic communication with the controller; and
a battery electrically connected to the waveform generator, wherein the controller receives an input from the user, instructs the waveform generator to deliver the pulse of energy to the desired tissue according to the input, and communicates data to the waveform logger according to the pulse of energy delivered, and wherein the battery sends an electrical charge to the waveform generator, the battery being a lithium ion, nickel metal hydride, lead acid, or nickel cadmium battery.

32. The device of claim 31, wherein the device is portable.

33. An electroporation handle assembly configured to deliver a pulse of energy to a desired tissue of a mammal to produce a constant current in the desired tissue similar to a preset current input by a user, comprising:
a skin electrode array including an electrode array having a plurality of skin electrodes in a spatial arrangement, wherein the electrode array is disposable and removably attached to the skin electrode assembly, and wherein at least one of the skin electrodes is neutral during delivery of the pulse of energy and measures impedance in the desired tissue;
a controller in communication with the skin electrode array, the controller controlling delivery of the pulse of energy through the skin electrodes; and
a means for performing a feedback mechanism, wherein the feedback mechanism is performed by software or hardware, which receives the measured impedance from the neutral skin electrode and adjusts the pulse of energy delivered, if needed, to maintain the constant current;
wherein the feedback mechanism is performed by an analog closed-loop circuit,
wherein the neutral electrode measures the impedance in the desired tissue and communicates the impedance to the feedback mechanism, and the feedback mechanism responds to the impedance and adjusts the pulse of energy to maintain the constant current at a value similar to the preset current, and
wherein the feedback mechanism maintains the constant current continuously and instantaneously during the delivery of the pulse of energy.

34. The handle assembly of claim 33, wherein the skin electrode array comprises three skin electrodes spatially arranged in a triangle.

35. The handle assembly of claim 33, wherein the skin electrodes are 5 mm in length and 26 gauge.

36. The handle assembly of claim 33, wherein during delivery of a pulse of energy at least two of the plurality of skin electrodes are active and one of the plurality of skin electrodes is neutral.

37. The handle assembly of claim 33, further comprising a safety feature, the safety feature being a voltage cap that prevents the skin electrodes from delivering the pulse of energy to the tissue when adjustment to the pulse of energy would yield a voltage above the voltage cap.

38. A method of delivering a pulse of energy to desired skin tissue in a mammal to cause electroporation to occur in cells of said desired tissue using an electroporation device configured to deliver the pulse of energy, producing a constant current similar to a preset current input by a user, wherein the desired skin tissue is subcutaneous or intradermic tissue, the method comprising:
inserting a plurality of needle skin electrodes into skin tissue without substantially penetrating a muscle tissue;
applying the pulse of energy to the plurality of needle skin electrodes to deliver a current equal to the preset current in the skin tissue; and
measuring impedance of the skin tissue with a neutral one of the plurality of needle skin electrodes and using a feedback mechanism in the electroporation device to adjust the pulse of energy applied in response to the measured impedance to maintain the current delivered to the skin tissue constant;
wherein the feedback mechanism is performed by an analog closed-loop circuit,
wherein the neutral electrode measures the impedance in the desired tissue and communicates the impedance to the feedback mechanism, and the feedback mechanism responds to the impedance and adjusts the pulse of energy to maintain the constant current at a value similar to the preset current, and
wherein the feedback mechanism maintains the constant current continuously and instantaneously during the delivery of the pulse of energy.

39. The method of claim 38, further comprising:
measuring impedance prior to applying the pulse of energy to determine whether electrical contact is made between the desired skin tissue and needle skin electrodes.

40. The method of claim 38, wherein at least one DNA vaccine is in contact with said intradermic or subcutaneous tissue.

41. The method of claim 38, further comprising recording data compiled by the electroporation device from the delivery of the pulse of energy to the desired skin tissue.

42. A method comprising the steps of:
providing an skin electrode assembly having a plurality of needle skin electrodes, the skin electrode assembly in electrical communication with a current waveform generator;
contacting skin tissue of a mammal with the plurality of needle skin electrodes without substantially penetrating a muscle tissue of the mammal; and
applying an electrical pulse of energy from the current waveform generator to the plurality of needle skin electrodes for a time and under conditions effective to expose the contacted skin tissue to a substantially constant current, wherein the applying the electrical pulse of energy step comprises:
measuring impedance in the contacted skin tissue with a neutral one of the plurality of needle skin electrodes; and
communicating the measured impedance to a feedback mechanism in electrical communication with the current waveform generator, wherein the feedback mechanism adjusts the pulse of energy delivered from the current waveform generator in response to the measured impedance to maintain the substantially constant current;
wherein the feedback mechanism is performed by an analog closed-loop circuit,
wherein the neutral electrode measures the impedance in the contacted skin tissue and communicates the impedance to the feedback mechanism, and the feedback mechanism responds to the impedance and adjusts the pulse of energy to maintain the constant current at a value similar to the preset current, and wherein the feedback mechanism maintains the constant current continuously and instantaneously during the delivery of the pulse of energy.

43. The method of claim 42, wherein the analog closed-loop circuit is part of the electroporation device.

44. The method of claim 42, further comprising setting a safety feature, the safety feature being a voltage cap that prevents the skin electrodes from delivering the pulse of energy to the tissue when adjustment to the pulse of energy would yield a voltage above the voltage cap.

* * * * *